(12) United States Patent
Macdonald et al.

(10) Patent No.: US 10,045,516 B2
(45) Date of Patent: Aug. 14, 2018

(54) GENETICALLY MODIFIED MAJOR HISTOCOMPATIBILITY COMPLEX ANIMALS

(71) Applicant: Regeneron Pharmaceuticals, Inc., Tarrytown, NY (US)

(72) Inventors: Lynn Macdonald, Harrison, NY (US); Andrew J. Murphy, Croton-on-Hudson, NY (US); Cagan Gurer, Chappaqua, NY (US); John McWhirter, Tarrytown, NY (US); Vera Voronina, Sleepy Hollow, NY (US); Faith Harris, Mamaroneck, NY (US); Sean Stevens, Del Mar, CA (US); Yingzi Xue, Ardsley, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/415,544

(22) Filed: Jan. 25, 2017

(65) Prior Publication Data
US 2017/0142944 A1  May 25, 2017

Related U.S. Application Data

(60) Division of application No. 13/793,812, filed on Mar. 11, 2013, now Pat. No. 9,591,835, which is a continuation-in-part of application No. 13/661,159, filed on Oct. 26, 2012, now Pat. No. 9,615,550.

(60) Provisional application No. 61/700,908, filed on Sep. 14, 2012, provisional application No. 61/552,582, filed on Oct. 28, 2011, provisional application No. 61/552,587, filed on Oct. 28, 2011.

(51) Int. Cl.
*A01K 67/027* (2006.01)

(52) U.S. Cl.
CPC ...... *A01K 67/0278* (2013.01); *A01K 2207/15* (2013.01); *A01K 2217/072* (2013.01); *A01K 2227/105* (2013.01); *A01K 2267/0387* (2013.01)

(58) Field of Classification Search
USPC .......................................................... 800/8
See application file for complete search history.

(56) References Cited

U.S. PATENT DOCUMENTS

| | | | |
|---|---|---|---|
| 5,413,923 A | 5/1995 | Kucherlapati et al. | |
| 5,416,260 A | 5/1995 | Koller et al. | |
| 5,574,205 A | 11/1996 | Kucherlapati et al. | |
| 5,644,065 A | 7/1997 | Benoist et al. | |
| 5,859,312 A | 1/1999 | Littman et al. | |
| 5,965,787 A | 10/1999 | Luthra et al. | |
| 6,002,066 A | 12/1999 | Leung et al. | |
| 6,139,835 A | 10/2000 | Kucherlapati et al. | |
| 6,150,584 A | 11/2000 | Kucherlapati et al. | |
| 6,270,772 B1 | 8/2001 | Burrows et al. | |
| 6,372,955 B1 | 4/2002 | Karlsson et al. | |
| 6,514,752 B1 | 2/2003 | Kucherlapati et al. | |
| 6,586,251 B2 | 7/2003 | Economides et al. | |
| 6,596,541 B2 | 7/2003 | Murphy et al. | |
| 6,815,171 B2 | 11/2004 | Burrows et al. | |
| 7,105,348 B2 | 9/2006 | Murphy et al. | |
| 7,265,218 B2 | 9/2007 | Burrows et al. | |
| 7,294,754 B2 | 11/2007 | Poueymirou et al. | |
| 7,339,089 B2 | 3/2008 | Gotch | |
| 7,663,017 B2 | 2/2010 | Lone et al. | |
| 7,745,690 B2 | 6/2010 | Kanazawa et al. | |
| 2002/0164721 A1 | 11/2002 | Firat et al. | |
| 2003/0093818 A1 | 5/2003 | Belmont et al. | |
| 2005/0050580 A1 | 3/2005 | Gotch et al. | |
| 2005/0066375 A1 | 3/2005 | Thiam et al. | |
| 2005/0114910 A1 | 5/2005 | Lone et al. | |
| 2006/0107339 A1 | 5/2006 | Gotch et al. | |
| 2007/0209083 A1 | 9/2007 | Thiam et al. | |
| 2009/0328240 A1 | 12/2009 | Sing et al. | |
| 2010/0011450 A1 | 1/2010 | Garcia et al. | |
| 2010/0138938 A1 | 6/2010 | Garcia et al. | |
| 2011/0067121 A1 | 3/2011 | Lone et al. | |
| 2014/0245466 A1 | 8/2014 | Macdonald et al. | |
| 2014/0245467 A1 | 8/2014 | Macdonald et al. | |
| 2015/0342163 A1 | 12/2015 | Voronina et al. | |

FOREIGN PATENT DOCUMENTS

| | | |
|---|---|---|
| EA | 0950707 B1 | 2/2009 |
| EP | 0437576 B1 | 7/2002 |
| EP | 1878342 A1 | 1/2008 |
| EP | 1878798 A1 | 1/2008 |
| EP | 1017721 B1 | 2/2009 |
| EP | 1409646 B1 | 6/2012 |

(Continued)

OTHER PUBLICATIONS

Allen et al. (1986) "B2-Microglobulin is not required for Cell surface expression of the murine class I histocompatibility antigen H-2Db or of a truncated H-2Db," PNAS, 83:7447-7451.
Altmann et al. (1995) "The T Cell Response to HLA-DR Transgenic Mice to Human Myelin Basic Protein and other Antigens in the Presence and Absence of Human CD4," J. Exp. Med., 181:867-875.
Arnold and Hammerling (1991) "MHC Class-1 Transgenic Mice," Annu. Rev. Immunol., 9:297-322.
Auerbach et al. (2000) "Establishment and Chimera Analysis of 129/SvEV- and C57BL/6-Derived Mouse Embryonic Stem Cell Lines," BioTechniques, 29:1024-1032.
Basha et al.(2008) "MHC Class I Endosomal and Lysosomal Trafficking Coincides with Exogenous Antigen Loading in Dendritic cells," PLoS ONE, 3:e3247, 11 pages.

(Continued)

*Primary Examiner* — Maria G Leavitt
(74) *Attorney, Agent, or Firm* — Rita S. Wu; Margarita Zippin; FisherBroyles, LLP

(57) ABSTRACT

The invention provides genetically modified non-human animals that express chimeric human/non-human MHC I polypeptide and/or human or humanized β2 microglobulin polypeptide, as well as embryos, cells, and tissues comprising the same. Also provided are constructs for making said genetically modified animals and methods of making the same. Methods of using the genetically modified animals to study various aspects of human immune system are provided.

8 Claims, 13 Drawing Sheets

(56) References Cited

FOREIGN PATENT DOCUMENTS

| WO | 199101140 A1 | 2/1991 |
|---|---|---|
| WO | 199211753 A1 | 7/1992 |
| WO | 199305817 A1 | 4/1993 |
| WO | 199503331 A1 | 2/1995 |
| WO | 1997032603 A1 | 9/1997 |
| WO | 1998024893 A2 | 6/1998 |
| WO | 2002059263 A2 | 8/2002 |
| WO | 2003006639 A1 | 1/2003 |
| WO | 2005004592 A2 | 1/2005 |
| WO | 2008010099 A2 | 1/2008 |
| WO | 2008010100 A2 | 1/2008 |
| WO | 2009114400 A1 | 9/2009 |
| WO | 2011004192 A1 | 1/2011 |
| WO | 2012039779 A1 | 3/2012 |
| WO | 2014130667 A1 | 8/2014 |
| WO | 2014130671 A1 | 8/2014 |

OTHER PUBLICATIONS

Benmohamed et al. (2000)"Induction of CTL Response by a Minimal Epitope Vaccine in HLA-A*0201/DR1 Transgenic Mice: Dependence on HLA Class II Restricted TH Response," Hum. Immunol., 61:764-779. Bernabeu et al. (1984) "B2-Microglobulin from serum associates with MHC class I antigens on the surface of cultured cells," Nature, 308:642-645.

Betser-Cohen et al. (2010) "The Association of MHC Class I Proteins with the 2B4 Receptor Inhibits Self-Killing of Human NK cells," J. Immunol., 184:2761-2768.

Chamberlain et al. (1988)"Tissue-specific and Cell surface expression of human major histocompatibility complex class I heavy (HLA-B7) and light (B2-microglobulin) chain genes in transgenic mice," PNAS, 86:7690-7694.

Chung et al. (1994) "Functional three-domain single-chain T-Cell receptors," PNAS, 91:12654-12658.

Connolly et al. (1988) "The Lyt-2 Molecule Recognizes Residues in the Class I alpha3 Domain in Allogeneic Cytotoxic T Cell Responses," J. Exp. Med., 168:325-341.

Cooper et al. (2007) "An Impaired Breeding Phenotype in Mice with a Genetic Deletion of Beta-2 Microglobulin and Diminished MHC Class I Expression: Role in Reproductive Fitness," Biol. Reprod., 77:274-279.

Cosson and Bonifacino (1992) "Role of Transmembrane Domain Interactions in the Assembly of Class II MHC Molecules," Science, 258:659-662.

Danner et al. (2011) "Expression of HLA Class II Molecules in Humanized NOD.Rag1KO.IL2RgKO Mice is Critical for Development and Function of Human T and B cells," PLoS ONE, 6:e19826, 12 pages.

De Bakker et al. (2006) "A high-resolution HLA and SNP haplotype map for disease association studies in the extended human MHC," Nature Genet., 38:1166-1172.

De Bakker et al. (2006) "A high-resolution HLA and SNP haplotype map for disease association studies in the extended human MHC," Nature Genet. Online Supplement, 33 pages.

De Gassart et al. (2008) "MHC class II stabilization at the surface of human dendritic cells is the result of maturation-dependent MARCH I down-regulation," PNAS, 105:3491-3496.

Dolan et al. (2004) "Invariant Chain and the MHC Class II Cytoplasmic Domains Regulate Localization of MHC Class II Molecules to Lipid Rafts in Tumor Cell-Based Vaccines," J. Immunol., 172:907-914.

Duke (1989) "Self-Recognition by T Cell," J. Exp. Med. 170:59-71.
El Fakhry et al. (2004) "Delineation of the HLA-DR Region and the Residues Involved in the Association with the Cytoskeleton," J. Biol. Chem., 279:18472-18480.

Festing et al. (1999) "Revised nomenclature for strain 129 mice," Mamm. Genome, 10:836.

Firat et al. (2002) "Comparative analysis of the CO8+ T Cell repertoires of H-2 class I wild-ype/HLA-2.1 and H-2 class I knockout/HLA-A2.1 transgenic mice," Internal. Immunol., 14:925-934.

Fooksman et al. (2009) "Cutting Edge: Phospholidylinositol 4,5-Bisphosphate Concentration at the APC Side of the Immunological Synapse Is Required for Effector T Cell Function," J. Immunol., 182:5179-5182.

Fugger et al. (1994) "Expression of HLA-DR4 and human CD4 transgenes in mice determines the variable region beta-chain T-Cell repertoire and mediates an HLA-DR-restricted immune response," PNAS, 91:6151-6155.

Fukui et al. (1993) "T-cell repertoire in a stain of transgenic C57BL/6 mice with the HLA-DRA gene on the X-chromosome," Immunogenetics, 37(3):204-211.

Fukui et al. (1997) "Differential requirement of MHC class II molecules expressed on hematopoietic cells for positive selection of CD4+ thymocytes in TCR $\alpha$ $\beta$ and TCR $\beta$ transgenic mice," Internal. Immunol., 9(9):1385-1391.

Gao et al. (1997) "Crystal structure of the complex between human CD88alpha-alpha and HLA-A2," Nature, 387:630-634.

Gao et al. (2000) "Molecular interactions of coreceptor CD8 and MHC class 1: the molecular basis for functional coordination with the T-Cell receptor," Immunol. Today, 21 (12):630-636.

Gruda et al. (2007) "Intracellular Cysteine Residues in the Tail of MHC Class I Proteins Are Crucial for Extracellular Recognition by Leukocyte Ig-Like Receptor 1," J. Immunol., 179:3655-3661.

Gur et al. (1997) "Structural Analysis of Class I MHC Molecules: The Cytoplasmic Domain Is Not Required for Cytoskeletal Association, Aggregation and Internalization," Mol. Immunol., 34:125-132.

Güssow et al. (1987) "The Human B2-Microglobulin Gene. Primary Structure and Definition of the Transcriptional Unit," J. Immunol., 139:3132-3138.

Holdsworth et al. (2009) "The HLA dictionary 2008: a summary of HLA-A, -B, -C -DRB1/3/4/5, and -DQB1 alleles and their association with serologically defined HLA-A, -B, -C, -DR, and -DO antigens," Tissue Antigens, 73:95-170.

International MHC and Autoimmunity Genetics Network (IMAGEN) (2009) "Mapping of multiple 40 susceptibility variants within the MHC region for 7 immune-mediated diseases," PNAS, 1 06: 18680-18685.

Irwin et al. (1989) "Species-restricted interactions between COB an the alpha3 domain of class I influence the magnitude of the xenogeneic response," J. Exp. Med., 170:1091-1101.

Ishimoto et al. (1997) "In vitro and in vivo evidence for high frequency of I-Ab-reactive CD4+ t cells in HLA-DQ, or HLA-DRA transgenic mice lacking endogenous MHC class I and/or class II expression," J. Immunol., 159(8):3717-3722.

Ito et al. (1996) "HLA-DR4-IE Chimeric Class II Transgenic, Murine Class 11-Deficient Mice Are Susceptible to Experimental Allergic Encephalomyelitis," J. Exp. Med., 183:2635-2644.

Jakobovits (1994) "Humanizing the mouse genome," Cur. Biol., 4(8):761-763.

Johansson et al. (2005) "Natural killer Cell education in mice with single or multiple major histocompatibility complex class I molecules," J. Exp. Med., 201:1145-1155.

Josson et al. (2011) "B2 microglobulin induces epithelial to mesenchymal transition and confers cancer lethality and bone metastasis in human cancer cells," Cancer Res., 71:1-11.

Kalinke et al. (1990) "Strong Xenogeneic HLA Response in Transgenic Mice after Introducing an Alpha3 Domain into HLA B27," Nature, 348:642-644.

Kaplan et al. (2005) "A new murine tumor model for studying HLA-A2-restricted anti-tumor immunity," Cancer Letters, 224:153-166.

Kievits et al. (1987) "HLA-restricted recognition of viral antigens in HLA transgenic mice," Nature 329:447-449.

Kirwan et al. (2005) "Killer Cell Ig-Like Receptor-Dependent Signaling by Ig-Like Transcript 2 (ILT2/CD85j/LILRB1/ LIR-1)," J. Immunol., 175:5006-5015.

Koller and Orr (1985) "Cloning and complete sequence of an HLA-A2 gene: Analysis of two HLA-A Alleles at the nucleotide Level" J. Immunol. 134(4):2727-2733.

Koller et al. (1990) "Normal Development of Mice Deficient in B2M, MHC Class I Proteins, and CD8+ T cells," Science, 248:1227-1230.

(56) References Cited

OTHER PUBLICATIONS

Kumanovics et al. (2003) "Genomic Organization of the Mammalian MHC," Annu. Rev. Immunol., 21:629-657.
Laface et al. (1995) "Human CD8 Transgene Regulation of HLA Recognition by Murine T cells," J. Exp. Med., 182:1315-1325.
Lee et al. (1982) "Sequence of an HLA-DR alpha-chain eDNA clone and intron-exon organization of the corresponding gene," Nature, 299:750-752.
Li et al. (2009) "Mamu-A*01/Kb transgenic and MHC Class I knockout mice as a tool for HIV vaccine development," Virology, 387:16-28.
Li et al. (2010) "Transgenic mice with a diverse human T Cell antigen receptor repertoire," Nature Med., 16(9):1029-1034.
Lie and Petropoulos (1998) "Advances in quantitative PCR technology: 5' nuclease assays," Curr. Opin. Biotech., 9:43-48.
Linnenbach et al. (1980) "DNA-transformed murine teratocarcinoma cells: regulation of expression of simian virus 40 tumor antigen in stem versus differentiated cells," PNAS, 77(8):4875-4879.
Lizee et al. (2003) "Control of dendritic cell cross-presentation by the major histocompatibility complex class I cytoplasmic domain," Nature Immunol., 4:1065-1073.
Lynch et al. (2009) "Novel MHC Class I Structures on Exosomes," J. Immunol., 183:1884-1891.
Madsen et al. (1999) "A humanized model for multiple sclerosis using HLA-DR2 and a human T-cell receptor," Nature Genet., 23:343-347.
Marsh et al. (2010) "Nomenclature for factors of the HLA system," 2010, Tissue Antigens, 75:291-455.
Mendez et al. (1997) "Functional transplant of megabase human immunoglobulin loci recapitulates human antibody response in mice," Nature Genet., 15(2):146-156.
Mombaerts et al. (1993) "Spontaneous Development of Inflammatory Bowel Disease in T Cell Receptor Mutant Mice," Cell, 75:275-282.
Murphy et al. (2008) "Janeway's Immunobiology" 7th ed., Garland Science, pp. 125-13B and 196-213.
Nickerson et al. (1990) "Expression of HLA-B27 in Transgenic Mice Is Dependent on the Mouse H-20 Genes," J. Exp. Med., 172:1255-1261.
Ostrand-Rosenberg et al. (1991) "Abrogation of Tumorigenicity by MHC Class II Antigen Expression Requires the Cytoplasmic Domain of the Class II Molecule," J. Immunol., 147:2419-2422.
Pajot et al. (2004) "A mouse model of human adaptive immune functions: HLA-A2.1/HLA-DR1-trasngenic H-2 class 1-/class 11-knockout mice," Eur. J. Immunol., 34:3060-3069.
Pascolo, et al. (1997) "HLA-A2.1-restricted Education and Cytolytic Activity of CD8+ T Lymphocytes from from β2 Microglobulin (β2m) HLA-A2.1 Monochain Transgenic H-2Db β2m Double Knockout Mice," J. Exp. Med., 185:2043-2051.
Pascolo, et al. (2005) "HLA class I transgenic mice: development, utilisation and improvement," Expert Opinion Biol. Ther., 5(7):919-938.
Perarnau et al. (1988) "Human B2-microglobulin specifically enhances cell-surface expression of HLA class I molecules in transfected murine cells," J. Immunol., 141:1383-1389.
Pettersen et al. (1998) "The TCR-Binding Region of the HLA Class I α2 Domain Signals Rapid Fast Independent Cell, Death: A Direct Pathway for T Cell-Mediated Killing of Target cells," J. Immunol., 160:4343-4352.
Pitiet et al. (2003) "Alpha3 Domain Mutants of Peptide/MHC Class I Multimers Allow the Selective Isolation of High Avidity Tumor-Reactive CD8 T cells," J. Immunol., 171 :1844-1849.
Potter et al. (1989) "Substitution at residue 227 of H-2 class I molecules abrogates recognition by CD8-dependent, but not CD8-independent, cytotoxic T lymphocytes," Nature, 337:73-75.
Poueymirou et al. (2007) "F0 generation mice fully derived from gene-targeted embryonic stem cells allowing immediate phenotypic analyses," Nature Biotech., 25:91-99.

Quinn et al. (1997) "Virus-Specific, CD8+ Major Histocompatibility Complex Class 1-Restricted Cytotoxic T Lymphocytes in Lymphocytic Choriomeningitis Virus-Infected B2-Microglobulin-Deficient Mice," J. Virol., 71 :8392-8396.
Raffegerst et al. (2009) "Diverse Hematological Malignancies Including Hodgkin-Like Lymphomas Develop in Chimeric MHC Class II Transgenic Mice," PLoS ONE, 4:e8539, 12 pages.
Ren et al. (2006) "Construction of bioactive chimeric MHC class I tetramer by expression and purification of human-murine chimeric MHC heavy chain and β2M as a fusion protein in *Escherichia coli*," Protein Expression and Purification, 50:171-78.
Rodriguez-Cruz et al. (2011) "Natural Splice Variant of MHC Class I Cytoplasmic Tail Enhances Dendritic Cell-Induced CD8+ T-Cell, Responses and Boosts Anti-Tumor Immunity," PLoS ONE, 6:e22939, 10 pages.
Rohrlich et al. (2003) "HLA-B*0702 transgenic, H-2$K^bD^b$ doubleknockout mice: phenotypical and functional characterization in response to influenza virus," International Immunology, 15(6):765-772.
Rosano et al. (2005) "The three-dimensional structure of B2 microglobulin: Results from X-ray crystallography," Biochim. Biophys. Acta, 1753:85-91.
Rubio et al. (2004) "Cross-linking of MHC class I molecules on human NK cells inhibits NK cell function, segregates MHC I from the NK cell synapse, and induces intracellular phosphotyrosines," J. Leukoc. Biol., 76:116-124.
Salter et al. (1989) "Polymorphism in the alpha3 domain of HLA-A molecules affects binding to CD8," Nature, 338:345-347.
Salter et al. (1990) "A binding site for the T-cell co-receptor CD8 on the alpha 3 domain of HLA-A2," Nature, 345:41-46.
Sanders et al. (1991) "Mutations in CD8 that Affect Interactions with HLA Class I and Monoclonal Anti-CD8 Antibodies," J. Exp. Med., 174:371-379.
Scheer et al. (2013) "Generation and utility of genetically humanized mouse models." Drug Discovery Today, 18(23/24):1200-1211.
Shankarkumar (2004) "The Human Leukocyte Antigen (HLA) System," Int. J. Hum. Genet., 4:91-103.
Sherman et al. (1992) "Selecting T Cell Receptors with High Affinity for Self-MHC by Decreasing the Contribution of CD8," Science, 258:815-818.
Shin et al. (2006) "Surface expression of MHC class II in dendritic cells is controlled by regulated ubiquitination," Nature, 444:115-118.
Shinohara et al. (2007) "Active integration: new strategies for transgenesis," Transgenic Res., 16:333-339.
Shiroishi et al. (2003) "Human inhibitory receptors Ig-like transcript 2 (ILT2) and ILT4 compete with CD8 for MHC class I binding and bind preferentially to HLA-G," PNAS, 100:8856-8861.
Shultz et al. (2007) "Humanized mice in translational biomedical research," Nature Rev., 7:118-130.
Sims et al (2004) "Genetic Susceptibility to Ankylosing Spondylitis," Cur. Mol. Med., 4(1):13-20.
Smiley et al. (1995) "Transgenic mice expressing MHC class II molecules with truncated A-beta cytoplasmic domains reveal signaling-independent defects in antigen presentation," Internal. Immunol., 7:665-677.
Street et al. (2002) "Limitations of HLA-transgenic mice in presentation of HLA-restricted cytotoxic T-cell epitopes from endogenously processed human papillomavirus type 16 E7 protein," Immunology, 106:526-536.
Takaki et al. (2006) "HLA-A*0201-Restricled T cells from Humanized NOD Mice Recognize Autoantigens of Potential Clinical Relevance to Type I Diabetes," J. Immunol., 176:3257-3265.
Tanabe et al. (1989) "Analysis of xenoantigenicity of HLA Class I molecules by a complete series of human-mouse hybrid genes," Transplantation, 48:1, 135-140.
Taneja and David (1998) "HLA Transgenic Mice as Humanized Mouse Models of Disease and Immunity," J. Clin. Invest., 101:921-926.
Taneja and David (2009) "Spontaneous autoimmune myocarditis and cardiomyopathy in HLA-DQ8.NODAbo transgenic mice," Journal of Autoimmunity 33:260-269.

(56) References Cited

OTHER PUBLICATIONS

Taylor et al. (1993) "Human immunoglobulin transgenes undergo rearrangement, somatic mutation and class switching in mice that lack endogenous IgM," Int. Immunol., 6(4):579-591.
Theobald et al. (1995) "Targeting p53 as a general tumor antigen," PNAS, 92:11993-11997.
Tishon et al. (2000) "Transgenic Mice Expressing Human HLA and CD8 Molecules Generate HLA-Restricted Measles Virus Cytotoxic T Lymphocytes of the Same Specificity as Humans with Natural Measles Infection," Virology, 275:286-293.
Ureta-Vidal et al. (1999) "Phenotypical and Functional Characterization of the CD8 + T Cell Repertoire of HLA-A2.1 Transgenic, H-2Kb°Db° Double Knockout Mice," J. Immunol., 163:2555-2560.
Valenzuela et al. (2003) "High-throughput engineering of the mouse genome coupled with high-resolution expression analysis", Nature Biotech., 21:652-659.
Vignali et al. (1992) "Species-specific Binding of CD4 to the Beta2 Domain of Major Histocompatibility Complex Class II Molecules," J. Exp. Med., 175:925-932.
Vitiello et al. (1991) "Analysis of the HLA-restricted Influenza-specific Cytotoxic T Lymphocyte Response in 6 Transgenic Mice Carrying a Chimeric Human-Mouse Class I Major Histocompatibility Complex," J. Exp. Med., 173:1007-1015.
Vugmeyster et al. (1998) "Major histocompatibility complex (MHC) class I KbDb −/− deficient mice possess functional CD8 + T cells and natural killer cells," PNAS, 95:12492-12497.
Wagner et al. (1994) "Antibodies generated from human immunoglobulin miniloci in transgenic mice," Nucleic Acids Res., 22(8):1389-1393.
Wagner et al. (1994) "Ligation of MHC Class I and Class II Molecules Can Lead to Heterologous Desensitization of Signal Transduction Pathways That Regulate Homotypic Adhesion in Human Lymphocytes," J. Immunol., 152:5275-5287.
Wagner et al. (1994) "The diversity of antigen-specific monoclonal antibodies from transgenic mice bearing human immunoglobulin gene miniloci," Eur. J. Immunol., 24(11):2672-2681.
Wang and Reinherz (2001) "Structural basis of T cell recognition of peptides bound to MHC molecules," Mol. Immunol., 38:1039-1049.
Willcox et al. (2003) "Crystal structure of HLA-A2 bound to LIR-1, a host and viral major histocompatibility complex receptor," Nature Immunol., 4:913-919.
Wong and Wen (2004) "What can the HLA transgenic mouse tell us about autoimmune diabetes?," Diabetologia, 47:1476-1487.
Woodle et al. (1997) "Anti-Human Class I MHC Antibodies Induce Apoptosis by a Pathway That Is Distinct from the Fas Antigen-Meidaled Pathway," J. Immunol., 158:2156-2164.
Woods et al. (1994) "Human Major Histocompatibility Complex Class 11-Restricted T Cell, Responses in Transgenic Mice," J. Exp. Med., 180:173-181.
Wooldridge et al. (2010) "MHC Class I Molecules with Superenhanced CD8 Binding Properties Bypass the Requirement for Cognate TCR Recognition and Nonspecifically Activate CTLs," J. Immunol., 184:3357-3366.
Yamamoto et al. (1994) "Functional Interaction between Human Histocompatibility Leukocyte Antigen (HLA) Class 27 II and Mouse CD4 Molecule in Antigen Recognition by T cells in HLA-DR and DQ Transgenic Mice," J. Exp. Med., 180:165-171.
Zijlstra et al. (1990) "B2-Microglobulin deficient mice lack CD4-8+ cytolytic T Cells," Nature, 344:742-746.
International Search Report and Written Opinion for PCT/US2014/023076, dated Jul. 18, 2014.
International Search Report and Written Opinion for PCT/US2012/062042, dated Feb. 18, 2013.
International Search Report and Written Opinion for PCT/US2014/017395, dated Jun. 2, 2014.
International Search Report and Written Opinion for PCT/US2014/017387, dated Jun. 2, 2014.
Statement of Relatedness under MPEP 2001.06 with Respect to U.S. Appl. No. 15/415,544 dated Jun. 22, 2017.
Samberg et al. (1989) "The α3 domain of major histocompatibility complex class I molecules plays a critical role in cytotoxic T lymphocyte stimulation," Eur. J. Immunol., 19(12):2349-2354.
Extended European Search Report with respect to Europe Application No. 17184955.7, dated Nov. 24, 2017.

GENETICALLY MODIFIED MAJOR HISTOCOMPATIBILITY COMPLEX ANIMALS

CROSS-REFERENCE TO RELATED APPLICATIONS

This application is a divisional of U.S. patent application Ser. No. 13/793,812, filed Mar. 11, 2013, now U.S. Pat. No. 9,591,835, which is a continuation-in-part of U.S. patent application Ser. No. 13/661,159, filed Oct. 26, 2012, now U.S. Pat. No. 9,615,550 which claims benefit of priority to U.S. Provisional Patent Application Nos. 61/552,582 and 61/552,587, both filed Oct. 28, 2011, and U.S. Provisional Patent Application No. 61/700,908, filed Sep. 14, 2012, all of which are hereby incorporated by reference herein in their entireties.

FIELD OF THE INVENTION

Present invention relates to a genetically modified non-human animal, e.g., a rodent (e.g., a mouse or a rat), that expresses a human or humanized Major Histocompatibility Complex (MHC) class I molecule. The invention also relates to a genetically modified non-human animal, e.g., a mouse or a rat, that expresses a human or humanized MHC I protein (e.g., MHC I α chain) and/or a human or humanized β2 microglobulin; as well as embryos, tissues, and cells expressing the same. The invention further provides methods for making a genetically modified non-human animal that expresses human or humanized MHC class I protein (e.g., MHC I α chain) and/or β2 microglobulin. Also provided are methods for identifying and evaluating peptides in the context of a humanized cellular immune system in vitro or in a genetically modified non-human animal, and methods of modifying an MHC I and/or a β2 microglobulin locus of a non-human animal. e.g., a mouse or a rat, to express a human or humanized MHC I and/or β2 microglobulin.

BACKGROUND OF THE INVENTION

In the adaptive immune response, foreign antigens are recognized by receptor molecules on B lymphocytes (e.g., immunoglobulins) and T lymphocytes (e.g., T cell receptor or TCR). These foreign antigens are presented on the surface of cells as peptide fragments by specialized proteins, generically referred to as major histocompatibility complex (MHC) molecules, MHC molecules are encoded by multiple loci that are found as a linked cluster of genes that spans about 4 Mb. In mice, the MHC genes are found on chromosome 17, and for historical reasons are referred to as the histocompatibility 2 (H-2) genes. In humans, the genes are found on chromosome 6 and are called human leukocyte antigen (HLA) genes. The loci in mice and humans are polygenic; they include three highly polymorphic classes of MHC genes (class I, II and III) that exhibit similar organization in human and murine genomes (see FIG. 2 and FIG. 3, respectively).

MHC loci exhibit the highest polymorphism in the genome; some genes are represented by >300 alleles (e.g., human HLA-DRβ and human HLA-B). All class I and II MHC genes can present peptide fragments, but each gene expresses a protein with different binding characteristics, reflecting polymorphisms and allelic variants. Any given individual has a unique range of peptide fragments that can be presented on the cell surface to B and T cells in the course of an immune response.

Both humans and mice have class I MHC genes (see FIG. 2 and FIG. 3). In humans, the classical class I genes are termed HLA-A, HLA-B and HLA-C, whereas in mice they are H-2K, H-2D and H-2L. Class I molecules consist of two chains: a polymorphic α-chain (sometimes referred to as heavy chain) and a smaller chain called β2-microglobulin (also known as light chain), which is generally not polymorphic (FIG. 1). These two chains form a non-covalent heterodimer on the cell surface. The α-chain contains three domains (α1, α2 and α3). Exon 1 of the α-chain gene encodes the leader sequence, exons 2 and 3 encode the α1 and α2 domains, exon 4 encodes the α3 domain, exon 5 encodes the transmembrane domain, and exons 6 and 7 encode the cytoplasmic tail. The α-chain forms a peptide-binding cleft involving the α1 and α2 domains (which resemble Ig-like domains) followed by the α3 domain, which is similar to β2-microglobulin.

β2 microglobulin is a non-glycosylated 12 kDa protein; one of its functions is to stabilize the MHC class I α-chain. Unlike the α-chain, the β2 microglobulin does not span the membrane. The human β2 microglobulin locus is on chromosome 15, while the mouse locus is on chromosome 2. β2 microglobulin gene consists of 4 exons and 3 introns. Circulating forms of β2 microglobulin are present in the serum, urine, and other body fluids; thus, the non-covalently MHC I-associated β2 microglobulin can be exchanged with circulating β2 microglobulin under physiological conditions.

Class I MHC molecules are expressed on all nucleated cells, including tumor cells. They are expressed specifically on T and B lymphocytes, macrophages, dendritic cells and neutrophils, among other cells, and function to display peptide fragments (typically 8-10 amino acids in length) on the surface to CD8+ cytotoxic T lymphocytes (CTLs). CTLs are specialized to kill any cell that bears an MHC I-bound peptide recognized by its own membrane-bound TCR. When a cell displays peptides derived from cellular proteins not normally present (e.g., of viral, tumor, or other non-self origin), such peptides are recognized by CTLs, which become activated and kill the cell displaying the peptide.

Typically, presentation of normal (i.e., self) proteins in the context of MHC I molecules does not elicit CTL activation due to the tolerance mechanisms. However, in some diseases (e.g., cancer, autoimmune diseases) peptides derived from self-proteins become a target of the cellular component of the immune system, which results in destruction of cells presenting such peptides. Although there has been advancement in recognizing some self-derived antigens that elicit cellular immune response (e.g., antigens associated with various cancers), in order to improve identification of peptides recognized by human CTLs through MHC class I molecules there remains a need for both in vivo and in vitro systems that mimic aspects of the human cellular immune system. Systems that mimic the human cellular immune system can be used in identifying disease-associated antigens in order to develop human therapeutics, e.g., vaccines and other biologics. Systems for assessing antigen recognition in the context of the human immune system can assist in identifying therapeutically useful CTL populations (e.g., useful for studying and combatting human disease). Such systems can also assist in enhancing the activity of human CTL populations to more effectively combat infections and foreign antigen-bearing entities. Thus, there is a need for biological systems (e.g., genetically engineered animals)

that can generate an immune system that displays components that mimic the function of human immune system.

SUMMARY OF THE INVENTION

A biological system for generating or identifying peptides that associate with human MHC class I proteins and chimeras thereof, and bind to CD8+ T cells, is provided. Non-human animals comprising non-human cells that express human or humanized molecules that function in the cellular immune response are provided. Humanized rodent loci that encode human or humanized MHC I and β2 microglobulin proteins are also provided. Humanized rodent cells that express human or humanized MHC and β2 microglobulin molecules are also provided. In vivo and in vitro systems are provided that comprise humanized rodent cells, wherein the rodent cells express one or more human or humanized immune system molecules.

Provided herein is a non-human animal, e.g., a rodent (e.g., a mouse or a rat), comprising in its genome a nucleotide sequence encoding a chimeric human/non-human (e.g., human/rodent, e.g., human/mouse or human/rat) MHC I polypeptide, wherein a human portion of the chimeric polypeptide comprises an extracellular domain of a human MHC I polypeptide. Specifically, provided herein is a non-human animal comprising at an endogenous MHC I locus a nucleotide sequence encoding a chimeric human/non-human MHC I polypeptide, wherein a human portion of the chimeric polypeptide comprises an extracellular domain of a human MHC I polypeptide, and wherein the animal expresses the chimeric human/non-human MHC I polypeptide. In one aspect, the animal does not express an extracellular domain (e.g., a functional extracellular domain) of an endogenous non-human MHC I polypeptide from an endogenous non-human MHC I locus. In one aspect of the invention, the non-human animal (e.g., a rodent, e.g., a mouse or a rat) comprises two copies of the MHC I locus comprising a nucleotide sequence encoding chimeric human/non-human (e.g., human/rodent, e.g., human/mouse or human/rat) MHC I polypeptide. In another aspect of the invention, the animal comprises one copy of the MHC I locus comprising a nucleotide sequence encoding a chimeric human/non-human MHC I polypeptide. Thus, the animal may be homozygous or heterozygous for the MHC I locus comprising a nucleotide sequence encoding chimeric human/non-human MHC I polypeptide. In various embodiments, the nucleotide sequence encoding a chimeric human/non-human MHC I polypeptide is comprised in the germline of the non-human animal (e.g., rodent, e.g., rat or mouse). In one embodiment, the chimeric MHC I locus is comprised in the germline of a non-human animal.

In one aspect, the nucleotide sequence encoding the chimeric human/non-human MHC I is operably linked to endogenous non-human regulatory elements, e.g., promoter, enhancer, silencer, etc. In one embodiment, a human portion of the chimeric polypeptide comprises a human leader sequence. In another embodiment, the chimeric polypeptide comprises a non-human leader sequence, e.g., endogenous non-human leader sequence. In an additional embodiment, the human portion of the chimeric polypeptide comprises α1, α2, and α3 domains of the human MHC I polypeptide. The human MHC I polypeptide may be selected from a group consisting of HLA-A, HLA-B, and HLA-C. In one embodiment, the human MHC I polypeptide is an HLA-a polypeptide, e.g., HLA-A2 polypeptide, e.g., an HLA-A2.1 polypeptide. In another embodiment, the human MHC I polypeptide is an HLA-B polypeptide, e.g., HLA-627 polypeptide.

In one aspect, the genetically engineered non-human animal is a rodent. In one embodiment, the rodent is a mouse. Thus, in one embodiment, the endogenous non-human locus is a mouse locus, e.g., a mouse H-2K, H-2D or H-2L locus. In one embodiment, the non-human portion of the chimeric human/non-human MHC I polypeptide comprises transmembrane and cytoplasmic domains of the endogenous non-human MHC I polypeptide. Thus, in an embodiment wherein the non-human animal is a mouse, the endogenous non-human MHC I locus may be an H-2K locus (e.g., H-2Kb locus) and the endogenous non-human MHC I polypeptide may be an H-2K polypeptide; therefore, the chimeric human/non-human MHC I polypeptide may comprise transmembrane and cytoplasmic domains of H-2K polypeptide. In another embodiment wherein the non-human animal is a mouse, the endogenous non-human MHC I locus may be an H-2D locus and the endogenous non-human MHC I polypeptide may be an H-2D polypeptide; therefore, the chimeric human/non-human MHC I polypeptide may comprise transmembrane and cytoplasmic domains of H-2D polypeptide. Similarly, in another embodiment, the endogenous non-human MHC I locus may be a mouse H-2L locus and the endogenous non-human MHC I polypeptide may be an H-2L polypeptide; therefore, the chimeric human/non-human MHC I polypeptide may comprise transmembrane and cytoplasmic domains of H-2L polypeptide.

Also provided herein is a mouse comprising at an endogenous H-2K locus a nucleotide sequence encoding a chimeric human/mouse MHC I polypeptide, wherein a human portion of the chimeric polypeptide comprises an extracellular domain of a human HLA-A (e.g., HLA-A2) polypeptide and a mouse portion comprises transmembrane and cytoplasmic domains of a mouse H-2K polypeptide, and wherein the mouse expresses the chimeric human/mouse MHC I polypeptide. In some embodiments, the mouse does not express an extracellular domain (e.g., does not express a functional extracellular domain) of the mouse H-2K polypeptide from an endogenous H-2K locus. In one aspect, the nucleotide sequence encoding a chimeric human/mouse MHC I polypeptide is operably linked to endogenous mouse regulatory elements. The human portion of the chimeric polypeptide may comprise a human leader sequence. It may also comprise α1, α2, and α3 domains of the human MHC I polypeptide. The human MHC I polypeptide may be HLA-A polypeptide, e.g., HLA-A2.1 polypeptide. In one aspect, the mouse H-2K locus is an H-2Kb locus.

Also provided herein is a mouse comprising at an endogenous H-2D locus a nucleotide sequence encoding a chimeric human/mouse MHC I polypeptide, wherein a human portion of the chimeric polypeptide comprises an extracellular domain of a human HLA-B (e.g., HLA-B27) polypeptide and a mouse portion comprises transmembrane and cytoplasmic domains of a mouse H-2D (e.g., H-2D1) polypeptide, and wherein the mouse expresses the chimeric human/mouse MHC I polypeptide. In some embodiments, the mouse does not express an extracellular domain (e.g., a functional extracellular domain) of the mouse H-2D polypeptide from an endogenous H-2D locus. In one aspect, the nucleotide sequence encoding a chimeric human/mouse MHC I polypeptide is operably linked to endogenous mouse regulatory elements. The human portion of the chimeric polypeptide may comprise a human leader sequence. The chimeric polypeptide may also comprise a mouse leader sequence. The human portion of the chimeric polypeptide may also comprise α1, α2, and α3 domains of the human MHC I polypeptide. The human MHC I polypeptide may be HLA-B polypeptide, e.g., HLA-627 polypeptide. In one aspect, the mouse H-2D locus is an H-2D1 locus.

In an additional embodiment, provided herein is a mouse that comprises at an endogenous mouse MHC I locus a nucleotide sequence encoding a chimeric human/mouse MHC I polypeptide, wherein the human portion of the chimeric polypeptide comprises an extracellular domain of a human MHC I selected from the group consisting of HLA-A2, HLA-A3, HLA-327, and HLA-B7. In another embodiment, provided herein is a mouse that comprises at an endogenous MHC I locus one or more, e.g., one, two, three, four, five, or six, nucleotide sequence(s) encoding a chimeric human/mouse MHC I polypeptide(s), wherein a human portion of the chimeric polypeptide(s) comprises an extracellular domain of a human MHC I polypeptide, wherein a mouse portion of a chimeric human/mouse MHC I polypeptide(s) comprises transmembrane and cytoplasmic domain of a mouse MHC I polypeptide, and wherein the mouse expresses one or more, e.g., one, two, three, four, five, or six, chimeric human/mouse MHC I polypeptide(s). Thus, the mouse MHC I polypeptide may be selected from H-2D, H-2K, and H-2L. In one embodiment, the chimeric human/mouse MHC I polypeptide may be selected from HLA-A2M-2K, HLA-A3/H-2K, HLA-B27/H-2D, HLA-B7/H-2D, and a combination thereof. In one embodiment, one, two, or three chimeric human/mouse MHC I polypeptide(s) may be encoded on each sister chromosome 17; thus, a mouse MHC I locus may comprise one or more, e.g., one, two, three, four, five, or six, nucleotide sequences encoding a chimeric human/mouse MHC I polypeptide(s). In one embodiment, the mouse comprises two nucleotide sequences encoding the chimeric human/mouse MHC I polypeptide(s), wherein the two nucleotide sequences encode HLA-A2/H-2K and HLA-B27/H-2D polypeptides, and wherein the mouse expresses the chimeric HLA-A2/H-2K and HLA-B27/H-2D polypeptides. In one embodiment, the mouse provided herein does not express any functional endogenous mouse MHC I polypeptides from the endogenous mouse MHC I locus. Thus, in one aspect, the mouse expresses only humanized, e.g., chimeric human/mouse MHC I polypeptides, and the remaining MHC I loci that do not comprise chimeric human/mouse MHC I sequences (e.g., MHC I loci that do not comprise replacement of endogenous mouse MHC I nucleotide sequences with those encoding chimeric human/mouse polypeptides) are removed by deletion. In another embodiment, the mouse retains a nucleotide sequence encoding a functional endogenous mouse MHC I polypeptide (e.g., H-2L polypeptide).

Another aspect of the invention relates to a non-human animal, e.g., a rodent (e.g., a mouse or a rat), comprising in its genome a nucleotide sequence encoding a human or humanized β2 microglobulin polypeptide. Thus, provided herein is a non-human animal comprising at an endogenous non-human β2 microglobulin locus a nucleotide sequence encoding a human or humanized β2 microglobulin polypeptide, wherein the animal expresses the human or humanized β2 microglobulin polypeptide. In one aspect, the animal does not express a functional endogenous non-human β2 microglobulin polypeptide from an endogenous non-human β2 microglobulin locus. In one aspect, the animal comprises two copies of the β2 microglobulin locus encoding the human or humanized β2 microglobulin polypeptide; in another embodiment, the animal comprises one copy of the β2 microglobulin locus encoding the human or humanized β2 microglobulin polypeptide. Thus, the animal may be homozygous or heterozygous for the β2 microglobulin locus encoding the human or humanized β2 microglobulin polypeptide. In various embodiments, the nucleotide sequence encoding the human or humanized β2 microglobulin polypeptide is comprised in the germline of the non-human animal (e.g., rodent, e.g., rat or mouse). In one embodiment, a nucleotide sequence encoding a human or humanized β2 microglobulin polypeptide comprises a nucleotide sequence encoding a polypeptide comprising a human β2 microglobulin amino acid sequence. In one embodiment, the polypeptide is capable of binding to an MHC I protein.

In some embodiments, the nucleotide sequence encoding the human or humanized microglobulin polypeptide is operably linked to endogenous non-human β2 microglobulin regulatory elements. In one aspect, the nucleotide sequence encoding the human or humanized β2 microglobulin polypeptide comprises a nucleotide sequence set forth in exon 2 to exon 4 of a human β2 microglobulin gene. In another aspect, the nucleotide sequence encoding the human or humanized β2 microglobulin polypeptide comprises nucleotide sequences set forth in exons 2, 3, and 4 of a human β2 microglobulin gene. In a further aspect, the nucleotide sequence also comprises a nucleotide sequence set forth in exon 1 of a non-human β2 microglobulin gene. In some embodiments, the non-human animal is a rodent (e.g., mouse or a rat); thus, the non-human β2 microglobulin locus is a rodent (e.g., a mouse or a rat) β2 microglobulin locus.

Also provided is a mouse comprising at an endogenous β2 microglobulin locus a nucleotide sequence encoding a human or humanized β2 microglobulin polypeptide, wherein the mouse expresses the human or humanized β2 microglobulin polypeptide. In some embodiments, the mouse does not express a functional endogenous mouse β2 microglobulin from an endogenous β2 microglobulin locus. The nucleotide sequence may be linked to endogenous mouse regulatory elements. In one aspect, the nucleotide sequence comprises a nucleotide sequence set forth in exon 2 to exon 4 of a human β2 microglobulin gene. Alternatively, the nucleotide sequence encoding the human or humanized β2 microglobulin polypeptide may comprise nucleotide sequences set forth in exons 2, 3, and 4 of a human β2 microglobulin gene. The nucleotide sequence encoding the human or humanized β2 microglobulin polypeptide may further comprise a nucleotide sequence of exon 1 of a mouse β2 microglobulin gene. In one embodiment, a nucleotide sequence encoding a human or humanized β2 microglobulin polypeptide comprises a nucleotide sequence encoding a polypeptide comprising a human β2 microglobulin amino acid sequence. In one embodiment, the polypeptide is capable of binding to an MHC I protein.

The invention further provides a non-human animal (e.g., a rodent, e.g., a mouse or a rat) comprising in its genome a nucleotide sequence encoding a chimeric human/non-human MHC I polypeptide and a nucleotide sequence encoding a human or humanized β2 microglobulin polypeptide. In one embodiment, the invention provides a non-human animal comprising in its genome a first nucleotide sequence encoding a chimeric human/non-human MHC I polypeptide, wherein a human portion of the chimeric polypeptide comprises an extracellular domain of a human MHC I polypeptide; and a second nucleotide sequence encoding a human or humanized β2 microglobulin polypeptide, wherein the first nucleotide sequence is located at an endogenous non-human MHC I locus, and the second nucleotide sequence is located at an endogenous non-human β2 microglobulin locus, and wherein the animal expresses the chimeric human/non-human MHC I polypeptide and the human or humanized β2 microglobulin polypeptide. In one aspect, the animal is a mouse. Thus, the endogenous MHC I locus may be selected from a group consisting of H-2K, H-2D, and H-2L locus. In one embodiment, the endogenous mouse locus is an H-2K locus (e.g., H-2Kb locus). In another embodiment, the endogenous mouse locus is an H-2D locus. In one embodiment, the human MHC I polypeptide is selected from the group consisting of HLA-A, HLA-B, and HLA-C polypeptide. In one aspect, the human MHC I polypeptide is HLA-A, e.g., HLA-A2 (e.g., HLA-A2.1). In another embodiment, the human MHC I polypeptide is HLA-B, e.g., HLA-B27. In various embodiments, the first and the second nucleotide sequences are comprised in the germline of the non-human animal (e.g., rodent, e.g., mouse or rat).

Therefore, in one embodiment, the invention provides a mouse comprising in its genome a first nucleotide sequence encoding a chimeric human/mouse MHC I polypeptide, wherein a human portion of the chimeric polypeptide comprises an extracellular domain of a human HLA-A (e.g., HLA-A2) and a mouse portion comprises transmembrane and cytoplasmic domains of a mouse H-2K; and a second nucleotide sequence encoding a human or humanized β2 microglobulin polypeptide, wherein the first nucleotide sequence is located at an endogenous H-2K locus and the second nucleotide sequence is located at an endogenous mouse β2 microglobulin locus, and wherein the mouse expresses the chimeric human/mouse MHC I polypeptide and the human or humanized β2 microglobulin polypeptide. In another embodiment, the invention provides a mouse comprising in its genome a first nucleotide sequence encoding a chimeric human/mouse MHC I polypeptide, wherein a human portion of the chimeric polypeptide comprises an extracellular domain of a human HLA-B (e.g., HLA-B27) and a mouse portion comprises transmembrane and cytoplasmic domains of a mouse H-2D; and a second nucleotide sequence encoding a human or humanized β2 microglobulin polypeptide, wherein the first nucleotide sequence is located at an endogenous H-2D locus and the second nucleotide sequence is located at an endogenous mouse β2 microglobulin locus, and wherein the mouse expresses the chimeric human/mouse MHC I polypeptide and the human or humanized β2 microglobulin polypeptide. In one embodiment, the non-human animal (e.g., the mouse) comprising both the chimeric MHC I polypeptide and human or humanized β2 microglobulin polypeptide does not express an extracellular domain (e.g., a functional extracellular domain) of an endogenous non-human MHC I polypeptide (e.g., the mouse H-2K or H-2D polypeptide) and/or a functional endogenous non-human (e.g., the mouse) β2 microglobulin polypeptides from their respective endogenous loci. In one aspect, the animal (e.g., the mouse) comprises two copies of each of the first and the second nucleotide sequence. In another aspect, the animal (e.g., the mouse) comprises one copy of the first and one copy of the second nucleotide sequences. Thus, the animal may be homozygous or heterozygous for both the first and the second nucleotide sequences.

In one aspect, the first nucleotide sequence is operably linked to endogenous non-human (e.g., mouse) MHC I regulatory elements, and the second nucleotide sequence is operably linked to endogenous non-human (e.g., mouse) β2 microglobulin elements. The human portion of the chimeric polypeptide may comprise α1, α2 and α3 domains of the human MHC I polypeptide. The second nucleotide sequence may comprise a nucleotide sequence set forth in exon 2 to exon 4 of a human β2 microglobulin gene. Alternatively, the second nucleotide sequence may comprise nucleotide sequences set forth in exons 2, 3, and 4 of a human β2 microglobulin gene. In one aspect, the mouse comprising both the chimeric MHC I polypeptide and human or humanized β2 microglobulin polypeptide may be such that the expression of human or humanized β2 microglobulin increases the expression of the chimeric human/mouse MHC I polypeptide as compared to the expression of the chimeric human/mouse MHC I polypeptide in the absence of expression of human or humanized β2 microglobulin polypeptide.

Additionally, provided herein is a mouse that comprises in its genome, e.g., at its endogenous MHC I locus, one or more, e.g., one, two, three, four, five, or six, nucleotide sequence(s) encoding a chimeric human/mouse MHC I polypeptide(s), and further comprising at its endogenous β2 microglobulin locus a nucleotide sequence encoding a human or humanized β2 microglobulin polypeptide. In one embodiment, the human portion of the chimeric MHC I polypeptide(s) comprises an extracellular domain of a human MHC I polypeptide and a mouse portion comprises transmembrane and cytoplasmic domains of a mouse MHC I polypeptide. Thus, the mouse may express one or more, e.g., one, two, three, four, five or six, chimeric human/mouse MHC I polypeptide(s) and a human or a humanized β2 microglobulin polypeptide.

Also provided are methods of making genetically engineered non-human animals (e.g., rodents, e.g., mice or rats) described herein. Thus, in one embodiment, provided is a method of modifying an MHC I locus of a non-human animal, e.g., a rodent (e.g., a mouse or a rat) to express a chimeric human/non-human, e.g., human/rodent (e.g., human/mouse or human/rat) MHC I polypeptide, wherein the method comprises replacing at the endogenous MHC I locus a nucleotide sequence encoding an extracellular domain of a non-human, e.g., rodent MHC I polypeptide with a nucleotide sequence encoding an extracellular domain of a human MHC I polypeptide. In another embodiment, provided is a method of modifying a β2 microglobulin locus of a non-human animal, e.g., a rodent (e.g., a mouse or a rat) to express a human or humanized β2 microglobulin polypeptide, wherein the method comprises replacing at the endogenous non-human, e.g., rodent (e.g., mouse or rat) β2 microglobulin locus a nucleotide sequence encoding a non-human, e.g., rodent (e.g., a mouse or a rat) β2 microglobulin polypeptide with a nucleotide sequence encoding a human or humanized β2 microglobulin polypeptide. In such methods, the replacement may be made in a single ES cell, and the single ES cell may be introduced into a non-human animal, e.g., rodent (e.g., a mouse or a rat) to make an embryo. The resultant non-human animal, e.g., rodent (e.g., a mouse or a rat) can be bred to generate a double humanized animal.

Thus, the invention also provides a method of making double humanized animals, e.g., rodents (e.g., mice or rats). In one embodiment, provided is a method of making a genetically modified mouse comprising (a) modifying an MHC I locus of a first mouse to express a chimeric human/mouse MHC I polypeptide comprising replacing at the endogenous mouse MHC I locus a nucleotide sequence encoding an extracellular domain of a mouse MHC I polypeptide with a nucleotide sequence encoding an extracellular domain of a human MHC I polypeptide, (b) modifying a β2 microglobulin locus of a second mouse to express a human or humanized β2 microglobulin polypeptide comprising replacing at the endogenous mouse β2 microglobulin locus a nucleotide sequence encoding a mouse β2 microglobulin polypeptide with a nucleotide sequence encoding a human or humanized β2 microglobulin polypeptide; and (c) breeding the first and the second mouse to generate a genetically modified mouse comprising in its genome a first nucleotide sequence encoding a chimeric human/mouse MHC I polypeptide and a second nucleotide sequence encoding a human or humanized β2 microglobulin polypeptide, wherein the genetically modified mouse expresses the chimeric human/ mouse MHC I polypeptide and the human or humanized β2 microglobulin polypeptide. In some embodiments, the MHC I locus is selected from H-2K, H-2D, and H-2L; in some embodiments, the human MHC I polypeptide is selected from HLA-A, HLA-B, and HLA-C. In one embodiment, the MHC I locus is an H-2K locus, the human MHC I polypeptide is HLA-A (e.g., HLA-A2), and the mouse expresses a chimeric HLA-AIH-2K polypeptide (e.g., HLA-A2/H-2K polypeptide). In one aspect, the chimeric HLA-A2/H-2K polypeptide comprises an extracellular domain of the HLA-A2 polypeptide and cytoplasmic and transmembrane domains of H-2K polypeptide. In another embodiment, the MHC I locus is an H-2D locus, the human MHC I polypeptide is HLA-B (e.g., HLA-827), and the mouse expresses a chimeric HLA-B2/H-2D polypeptide (e.g., HLA-B27/H-2D polypeptide). In one aspect, the chimeric HLA-B27/H-2D polypeptide comprises an extracellular domain of the HLA-B27 polypeptide and cytoplasmic and transmembrane domains of H-2D polypeptide. In one aspect, the second nucleotide sequence comprises nucleotide sequences set forth in exons 2, 3, and 4 (e.g., exon 2 to exon 4) of a human β2 microglobulin gene, and a nucleotide sequence set forth in exon 1 of a mouse β2 microglobulin gene.

Also provided herein is a non-human chimeric MHC I locus encoding a chimeric human/non-human MHC I polypeptide, comprising a first nucleotide sequence encoding a human MHC I extracellular domain operably linked to a second nucleotide sequence encoding a non-human MHC E transmembrane and cytoplasmic domains. In one aspect, the chimeric MHC I locus is at an endogenous MHC I position in a genome of a non-human animal. In one aspect, the chimeric MHC I locus expresses a chimeric human/non-human (e.g., human/rodent, e.g., human/mouse or human/rat) MHC I polypeptide. In one embodiment, the human MHC I is selected from HLA-A, HLA-B, and HLA-C (e.g., HLA-B27 or HLA-A2). In one embodiment, the non-human MHC I is a mouse MHC I selected from H-2D, H-2K, and H-2L (e.g., H-2D or H-2K). In one embodiment, the chimeric MHC I locus expresses one or more chimeric human/ non-human MHC I polypeptide(s).

Also provided herein is a genetically modified β2 microglobulin locus comprising a nucleotide sequence encoding a human or humanized β2 microglobulin polypeptide. In one aspect, the locus comprises a first nucleotide sequence comprising the sequence set forth in exons 2, 3, and 4 (e.g., exons 2-4) of a human β2 microglobulin gene, and a second nucleotide sequence comprising the sequence set forth in exon 1 of a non-human (e.g., rodent, e.g., rat or mouse) β2 microglobulin gene. In one embodiment, the second nucleotide sequence is operably linked to the first nucleotide sequence. In one aspect, the genetically modified β2 microglobulin locus is at an endogenous β2 microglobulin position in a genome of a non-human animal. In one aspect, the genetically modified β2 microglobulin locus expresses a human or humanized β2 microglobulin polypeptide.

In one aspect, the non-human chimeric MHC I locus is obtainable by any methods described herein for generating genetically modified non-human animals (e.g., rodents, e.g., mice or rats). In one aspect, the genetically modified β2 microglobulin locus is obtainable by any methods described herein for generating genetically modified non-human animals (e.g., rodents, e.g., mice or rats).

Also provided herein are cells, e.g., isolated antigen-presenting cells, derived from the non-human animals (e.g., rodents, e.g., mice or rats) described herein. Tissues and embryos derived from the non-human animals described herein are also provided.

In yet another embodiment, the invention provides methods for identification of antigens or antigen epitopes that elicit immune response, methods for evaluating a vaccine candidate, methods for identification of high affinity T cells to human pathogens or cancer antigens.

Any of the embodiments and aspects described herein can be used in conjunction with one another, unless otherwise indicated or apparent from the context. Other embodiments will become apparent to those skilled in the art from a review of the ensuing detailed description. The following detailed description includes exemplary representations of various embodiments of the invention, which are not restrictive of the invention as claimed. The accompanying figures constitute a part of this specification and, together with the description, serve only to illustrate embodiments and not to limit the invention.

DETAILED DESCRIPTION OF THE INVENTION

Definitions

Figure 1:
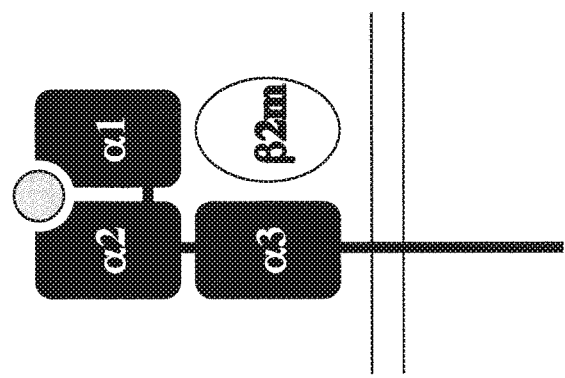
FIG. 1 is a schematic drawing of the four domains of a class I MHC molecule: α-chain containing the α1, α2 and α3 domains and the non-covalently associated fourth domain, β2-microglobulin (β2m). The gray circle represents a peptide bound in the peptide-binding cleft.

The present invention provides genetically modified non-human animals (e.g., mice, rats, rabbits, etc.) that express human or humanized MHC I and/or β2 microglobulin polypeptides; embryos, cells, and tissues comprising the same; methods of making the same; as well as methods of using the same. Unless defined otherwise, all terms and phrases used herein include the meanings that the terms and phrases have attained in the art, unless the contrary is clearly indicated or clearly apparent from the context in which the term or phrase is used.

The term "conservative," when used to describe a conservative amino acid substitution, includes substitution of an amino acid residue by another amino acid residue having a side chain R group with similar chemical properties (e.g., charge or hydrophobicity). Conservative amino acid substitutions may be achieved by modifying a nucleotide sequence so as to introduce a nucleotide change that will encode the conservative substitution. In general, a conservative amino acid substitution will not substantially change the functional properties of interest of a protein, for example, the ability of MHC I to present a peptide of interest. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet et al. ((1992) Exhaustive Matching of the Entire Protein Sequence Database, Science 256:1443-45), hereby incorporated by reference. In some embodiments, the substitution is a moderately conservative substitution wherein the substitution has a nonnegative value in the PAM250 log-likelihood matrix.

Thus, also encompassed by the invention is a genetically modified non-human animal whose genome comprises a nucleotide sequence encoding a human or humanized MHC I polypeptide and/or β2 microglobulin polypeptide, wherein the polypeptide(s) comprises conservative amino acid substitutions of the amino acid sequence(s) described herein.

One skilled in the art would understand that in addition to the nucleic acid residues encoding a human or humanized MHC I polypeptide and/or β2 microglobulin described herein, due to the degeneracy of the genetic code, other nucleic acids may encode the polypeptide(s) of the invention. Therefore, in addition to a genetically modified non-human animal that comprises in its genome a nucleotide sequence encoding MHC I and/or β2 microglobulin polypeptide(s) with conservative amino acid substitutions, a non-human animal whose genome comprises a nucleotide sequence(s) that differs from that described herein due to the degeneracy of the genetic code is also provided.

The term "identity" when used in connection with sequence includes identity as determined by a number of different algorithms known in the art that can be used to measure nucleotide and/or amino acid sequence identity. In some embodiments described herein, identities are determined using a ClustalW v, 1.83 (slow) alignment employing an open gap penalty of 10.0, an extend gap penalty of 0.1, and using a Gonnet similarity matrix (MacVector™ 10.0.2, MacVector Inc., 2008). The length of the sequences compared with respect to identity of sequences will depend upon the particular sequences. In various embodiments, identity is determined by comparing the sequence of a mature protein from its N-terminal to its C-terminal. In various embodiments when comparing a chimeric human/non-human sequence to a human sequence, the human portion of the chimeric human/non-human sequence (but not the non-human portion) is used in making a comparison for the purpose of ascertaining a level of identity between a human sequence and a human portion of a chimeric human/non-human sequence (e.g., comparing a human ectodomain of a chimeric human/mouse protein to a human ectodomain of a human protein).

The terms "homology" or "homologous" in reference to sequences, e.g., nucleotide or amino acid sequences, means two sequences which, upon optimal alignment and comparison, are identical in, e.g., at least about 75% of nucleotides or amino acids, e.g., at least about 80% of nucleotides or amino acids, e.g., at least about 90-95% nucleotides or amino acids, e.g., greater than 97% nucleotides or amino acids. One skilled in the art would understand that, for optimal gene targeting, the targeting construct should contain arms homologous to endogenous DNA sequences (i.e., "homology arms"); thus, homologous recombination can occur between the targeting construct and the targeted endogenous sequence.

The term "operably linked" refers to a juxtaposition wherein the components so described are in a relationship permitting them to function in their intended manner. As such, a nucleic acid sequence encoding a protein may be operably linked to regulatory sequences (e.g., promoter, enhancer, silencer sequence, etc.) so as to retain proper transcriptional regulation. In addition, various portions of the chimeric or humanized protein of the invention may be operably linked to retain proper folding, processing, targeting, expression, and other functional properties of the protein in the cell. Unless stated otherwise, various domains of the chimeric or humanized proteins of the invention are operably linked to each other.

The term "MHC I complex" or the like, as used herein, includes the complex between the MHC I $\alpha$ chain polypeptide and the $\beta$2-microglobulin polypeptide. The term "MHC I polypeptide" or the like, as used herein, includes the MHC I $\alpha$ chain polypeptide alone. Typically, the terms "human MHC" and "HLA" can be used interchangeably.

The term "replacement" in reference to gene replacement refers to placing exogenous genetic material at an endogenous genetic locus, thereby replacing all or a portion of the endogenous gene with an orthologous or homologous nucleic acid sequence. As demonstrated in the Examples below, nucleic acid sequences of endogenous loci encoding portions of mouse MHC I and $\beta$2 microglobulin polypeptides were replaced by nucleotide sequences encoding portions of human MHC I and $\beta$2 microglobulin polypeptides, respectively.

"Functional" as used herein, e.g., in reference to a functional polypeptide, refers to a polypeptide that retains at least one biological activity normally associated with the native protein. For example, in some embodiments of the invention, a replacement at an endogenous locus (e.g., replacement at an endogenous non-human MHC I and/or $\beta$2 microglobulin locus) results in a locus that fails to express a functional endogenous polypeptide. Likewise, the term "functional" as used herein in reference to functional extracellular domain of a protein, refers to an extracellular domain that retains its functionality, e.g., in the case of MHC I, ability to bind an antigen, ability to bind a T cell co-receptor, etc. In some embodiments of the invention, a replacement at the endogenous MHC locus results in a locus that fails to express an extracellular domain (e.g., a functional extracellular domain) of an endogenous MHC while expressing an extracellular domain (e.g., a functional extracellular domain) of a human MHC.

Several aspects described herein below for the genetically modified MHC I non-human animals, e.g., animal type; animal strains; cell types; screening, detection and other methods; methods of use; etc., will be applicable to the genetically engineered $\beta$2 microglobulin and MHC I/$\beta$2 microglobulin animals.

Genetically Modified MHC I Animals

In various embodiments, the invention generally provides genetically modified non-human animals that comprise in their genome a nucleotide sequence encoding a human or humanized MHC I polypeptide; thus, the animals express a human or humanized MHC I polypeptide.

Figure 2:
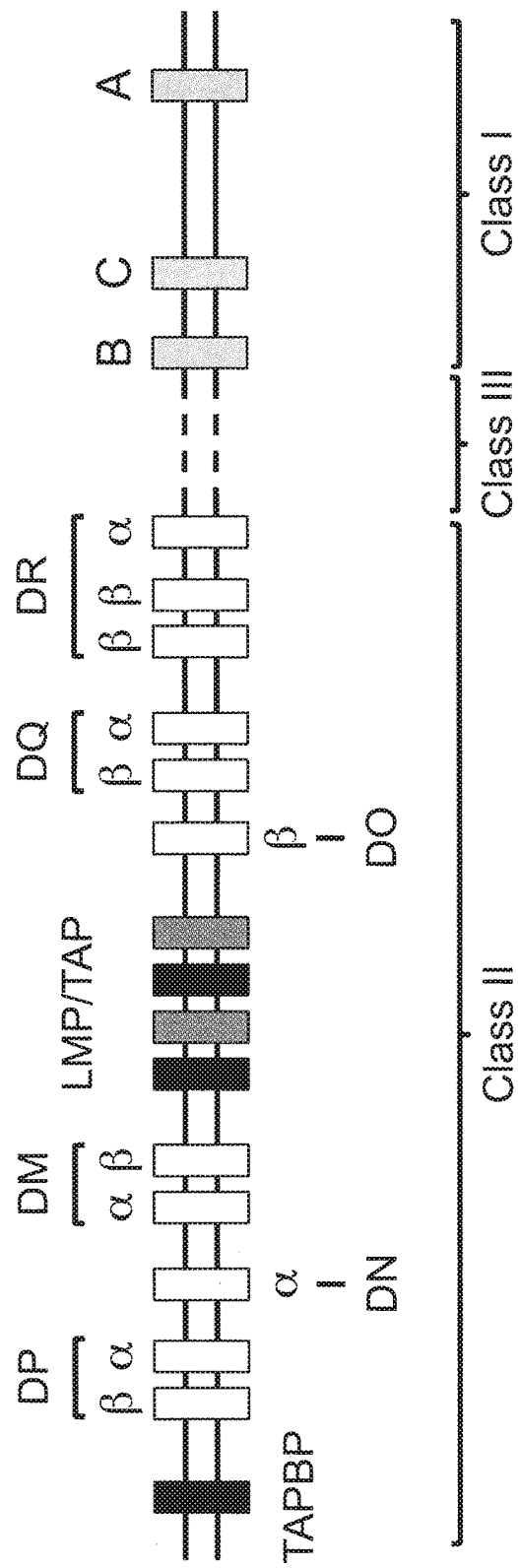
FIG. 2 is a schematic representation (not to scale) of the relative genomic structure of the human HLA, showing class I, II and III genes.
Figure 3:
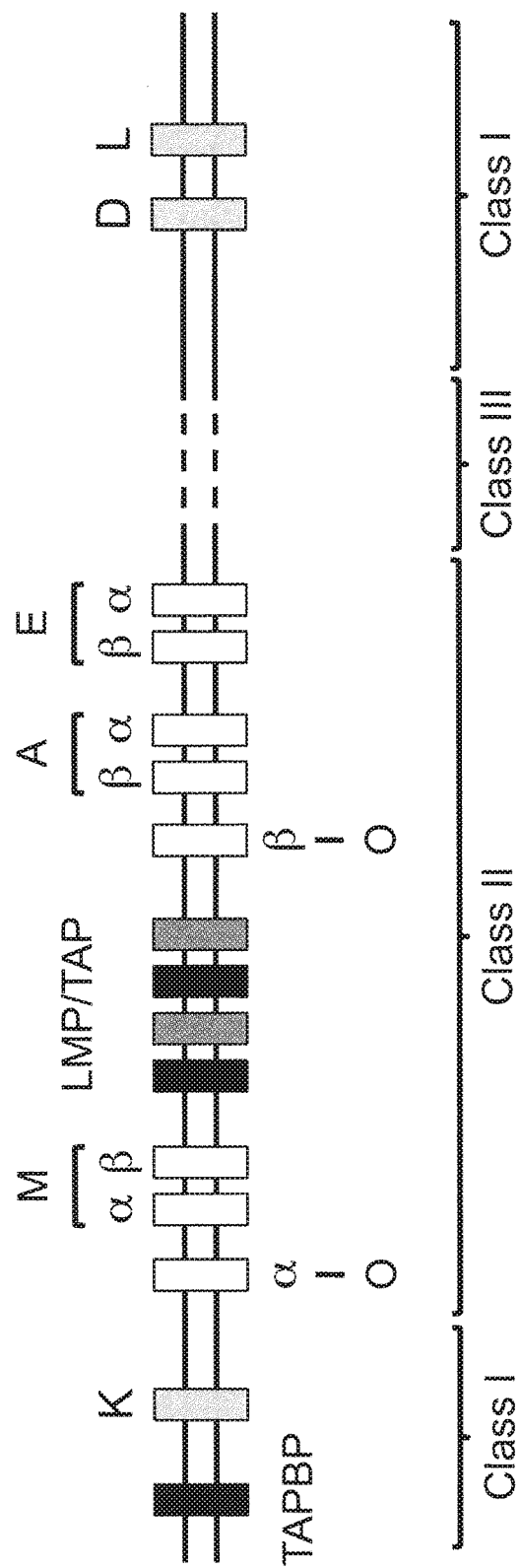
FIG. 3 is a schematic representation (not to scale) of the relative genomic structure of the mouse MHC, showing class I, II and III genes.

MHC genes are categorized into three classes: class I, class II, and class III, all of which are encoded either on human chromosome 6 or mouse chromosome 17. A schematic of the relative organization of the human and mouse MHC classes is presented in FIGS. 2 and 3, respectively. The MHC genes are among the most polymorphic genes of the mouse and human genomes, MHC polymorphisms are presumed to be important in providing evolutionary advantage; changes in sequence can result in differences in peptide binding that allow for better presentation of pathogens to cytotoxic T cells.

MHC class I protein comprises an extracellular domain (which comprises three domains: $\alpha_1$, $\alpha_2$ and $\alpha_3$), a transmembrane domain, and a cytoplasmic tail. The $\alpha_1$ and $\alpha_2$ domains form the peptide-binding cleft, while the $\alpha_3$ interacts with $\beta$2-microglobulin.

In addition to its interaction with $\beta$2-microglobulin, the $\alpha_3$ domain interacts with the TCR co-receptor CD8, facilitating antigen-specific activation. Although binding of MHC class I to CD8 is about 100-fold weaker than binding of TCR to MHC class I, CD8 binding enhances the affinity of TCR binding. Wooldridge et al. (2010) MHC Class I Molecules with Superenhanced CD8 Binding Properties Bypass the Requirement for Cognate TCR Recognition and Nonspecifically Activate CTLs, J. Immunol. 184:3357-3366. Interestingly, increasing MHC class I binding to CD8 abrogated antigen specificity in CTL activation. Id.

CD8 binding to MHC class I molecules is species-specific; the mouse homolog of CD8, Lyt-2, was shown to bind H-2D$^d$ molecules at the $\alpha$3 domain, but it did not bind HLA-A molecules, Connolly et al. (1988) The Lyt-2 Molecule Recognizes Residues in the Class I $\alpha$3 Domain in Allogeneic Cytotoxic T Cell Responses, J. Exp. Med. 168: 325-341. Differential binding was presumably due to CDR-like determinants (CDR1- and CDR2-like) on CD8 that was not conserved between humans and mice. Sanders et al. (1991) Mutations in CD8 that Affect Interactions with HLA Class I and Monoclonal Anti-CD8 Antibodies, J. Exp. Med. 174:371-379; Vitiello et al. (1991) Analysis of the HLA-restricted Influenza-specific Cytotoxic T Lymphocyte Response in Transgenic Mice Carrying a Chimeric Human-Mouse Class I Major Histocompatibility Complex, J. Exp. Med. 173:1007-1015; and, Gao et al. (1997) Crystal structure of the complex between human CD8$\alpha\alpha$ and HLA-A2, Nature 387:630-634. It has been reported that CD8 binds HLA-A2 in a conserved region of the $\alpha$3 domain (at position 223-229). A single substitution (V245A) in HLA-A reduced binding of CD8 to HLA-A, with a concomitant large reduction in T cell-mediated lysis. Salter et al. (1989), Polymorphism in the $\alpha_3$ domain of HLA-A molecules affects binding to CD8, Nature 338:345-348. In general, polymorphism in the $\alpha$3 domain of HLA-A molecules also affected binding to CD8. Id. In mice, amino acid substitution at residue 227 in H-2D$^d$ affected the binding of mouse Lyt-2 to H-2D$^d$, and cells transfected with a mutant H-2D$^d$ were not lysed by CD8+ T cells. Potter et al. (1989) Substitution at residue 227 of H-2 class I molecules abrogates recognition by CD8-dependent, but not CD8-independent, cytotoxic T lymphocytes, Nature 337:73-75.

Therefore, due to species specificity of interaction between the MHC class I $\alpha$3 domain and CD8, an MHC I complex comprising a replacement of an H-2K $\alpha$3 domain with a human HLA-A2 $\alpha$3 domain was nonfunctional in a mouse (i.e., in vivo) in the absence of a human CD8. In animals transgenic for HLA-A2, substitution of human $\alpha$3 domain for the mouse $\alpha$3 domain resulted in restoration of T cell response. Irwin et al. (1989) Species-restricted interactions between CD8 and the α3 domain of class I influence the magnitude of the xenogeneic response, J. Exp. Med. 170:1091-1101; Vitiello et al. (1991), supra.

The transmembrane domain and cytoplasmic tail of mouse MHC class I proteins also have important functions. One function of MHC I transmembrane domain is to facilitate modulation by HLA-A2 of homotypic cell adhesion (to enhance or inhibit adhesion), presumably as the result of cross-linking (or ligation) of surface MHC molecules. Wagner et al. (1994) Ligation of MHC Class I and Class II Molecules Can Lead to Heterologous Desensitization of Signal Transduction Pathways That Regulate Homotypic Adhesion in Human Lymphocytes, J. Immunol. 152:5275-5287. Cell adhesion can be affected by mAbs that bind at diverse epitopes of the HLA-A2 molecule, suggesting that there are multiple sites on HLA-A2 implicated in modulating homotypic cell adhesion; depending on the epitope bound, the affect can be to enhance or to inhibit HLA-A2-dependent adhesion. Id.

The cytoplasmic tail, encoded by exons 6 and 7 of the MHC I gene, is reportedly necessary for proper expression on the cell surface and for LIR1-mediated inhibition of NK cell cytotoxicity. Gruda et al. (2007) Intracellular Cysteine Residues in the Tail of MHC Class I Proteins Are Crucial for Extracellular Recognition by Leukocyte Ig-Like Receptor 1, J. Immunol. 179:3655-3661. A cytoplasmic tail is required for multimerizaton of at least some MHC I molecules through formation of disulfide bonds on its cysteine residues, and thus may play a role in clustering and in recognition by NK cells. Lynch et al. (2009) Novel MHC Class I Structures on Exosomes, J. Immunol. 183:1884-1891.

The cytoplasmic domain of HLA-A2 contains a constitutively phosphorylated serine residue and a phosphorylatable tyrosine, although—in Jurkat cells—mutant HLA-A2 molecules lacking a cytoplasmic domain appear normal with respect to expression, cytoskeletal association, aggregation, and endocytic internalization. Gur et al. (1997) Structural Analysis of Class I MHC Molecules: The Cytoplasmic Domain Is Not Required for. Cytoskeletal Association, Aggregation, and Internalization, Mol. Immunol. 34(2):125-132. Truncated HLA-A2 molecules lacking the cytoplasmic domain are apparently normally expressed and associate with β2 microglobulin. Id.

However, several studies have demonstrated that the cytoplasmic tail is critical in intracellular trafficking, dendritic cell (DC)-mediated antigen presentation, and CTL priming. A tyrosine residue encoded by exon 6 was shown to be required for MHC I trafficking through endosomal compartments, presentation of exogenous antigens, and CTL priming; while deletion of exon 7 caused enhancement of anti-viral CTL responses. Lizee et al. (2003) Control of Dendritic Cross-Presentation by the Major Histocompatibility Complex Class I Cytoplasmic Domain, Nature Immunol. 4:1065-73; Basha et al. (2008) MHC Class I Endosomal and Lysosomal Trafficking Coincides with Exogenous Antigen Loading in Dendritic Cells, PLoS ONE 3:e3247; and Rodriguez-Cruz et al. (2011) Natural Splice Variant of MHC Class I Cytoplasmic Tail Enhances Dendritic Cell-Induced CD8+ T-Cell Responses and Boosts Anti-Tumor Immunity, PLoS ONE 6:e22939.

In various embodiments, the invention provides a genetically modified non-human animal (e.g., mouse, rat, rabbit, etc.) that comprises in its genome a nucleotide sequence encoding a human or humanized MHC class I polypeptide. The non-human animal may comprise in its genome a nucleotide sequence that encodes an MHC I polypeptide that is partially human and partially non-human, e.g., a non-human animal that expresses a chimeric human/non-human MHC I polypeptide. In one aspect, the non-human animal only expresses the human or humanized MHC I polypeptide, e.g., chimeric human/non-human MHC I polypeptide, and does not express an endogenous non-human MHC I protein (e.g., a functional endogenous non-human MHC I protein) from an endogenous MHC I locus.

In one embodiment, provided herein is a non-human animal, e.g., a rodent, e.g., a rat or a mouse, comprising in its genome, e.g., at an endogenous non-human MHC I locus, a nucleotide sequence encoding a human MHC I polypeptide. In another embodiment, provided herein is a non-human animal, e.g., a rodent, e.g., a rat or a mouse, comprising in its genome, e.g., at an endogenous MHC I locus, a nucleotide sequence encoding a chimeric human/non-human MHC I polypeptide.

In one embodiment, the chimeric human/non-human MHC I polypeptide comprises in its human portion a peptide binding domain of a human MHC I polypeptide. In one aspect, the human portion of the chimeric polypeptide comprises an extracellular domain of a human MHC I. In this embodiment, the human portion of the chimeric polypeptide comprises an extracellular domain of an α chain of a human MHC I. In one embodiment, the human portion of the chimeric polypeptide comprises α1 and α2 domains of a human MHC I. In another embodiment, the human portion of the chimeric polypeptide comprises α1, α2, and α3 domains of a human MHC I. In one embodiment, the human portion of the chimeric polypeptide (e.g., the extracellular domain of the chimeric polypeptide) comprises a human leader sequence. In another embodiment, the chimeric polypeptide (e.g., the extracellular domain of the chimeric polypeptide) comprises a non-human leader sequence (e.g., endogenous non-human leader sequence).

The human or humanized MHC I polypeptide may be derived from a functional human HLA molecule encoded by any of HLA-A, HLA-B, HLA-C, HLA-E, HLA-F, or HLA-G loci. A list of commonly used HLA antigens is described in Shankarkumar et al. ((2004) The Human Leukocyte Antigen (HLA) System, Int. J. Hum. Genet. 4(2):91-103), incorporated herein by reference. Shankarkumar et al. also present a brief explanation of HLA nomenclature used in the art. Additional information regarding HLA nomenclature and various HLA alleles can be found in Holdsworth et al. (2009) The HLA dictionary 2008: a summary of HLA-A, -B, -C, DRB1/3/4/5, and DQB1 alleles and their association with serologically defined HLA-A, -B, -C, -DR, and -DQ antigens, Tissue Antigens 73:95-170, and a recent update by Marsh et al. (2010) Nomenclature for factors of the HLA system, 2010, Tissue Antigens 75:291-455, both incorporated herein by reference. Thus, the human or humanized MHC I polypeptide may be derived from any functional human HLA class I molecules described therein.

In one specific aspect, the human or humanized MHC I polypeptide is derived from human HLA-A. In a specific embodiment, the HLA-A polypeptide is an HLA-A2 polypeptide (e.g., and HLA-A2.1 polypeptide). In one embodiment, the HLA-A polypeptide is a polypeptide encoded by an HLA-A*0201 allele, e.g., HLA-A*012:01:01:01 allele. The HLA-A*0201 allele is commonly used amongst the North American population. Although the present Examples describe this particular HLA sequence, any suitable HLA-A sequence is encompassed herein, e.g., polymorphic variants of HLA-A2 exhibited in human population, sequences with one or more conservative or non-conservative amino acid modifications, nucleic acid sequences differing from the sequence described herein due to the degeneracy of genetic code, etc.

In one aspect, a non-human animal that expresses a human HLA-A2 sequence is provided, wherein the human HLA-A2 sequence comprises one or more conservative or non-conservative modifications.

In one aspect, a non-human animal that expresses a human HLA-A2 sequence is provided, wherein the human HLA-A2 sequence is at least about 85%, 90%, 95%, 96%, 97%, 98%, or 99% identical to a human HLA-A2 sequence. In a specific embodiment, the human HLA-A2 sequence is at least about 90%, 95%, 96%, 97%, 98%, or 99% identical to the human HLA-A2 sequence described in the Examples. In one embodiment, the human HLA-A2 sequence comprises one or more conservative substitutions. In one embodiment, the human HLA-A2 sequence comprises one or more non-conservative substitutions.

In another specific aspect, the human or humanized MHC I polypeptide is derived from human MHC I selected from HLA-B and HLA-C. In one aspect, the human or humanized MHC I is derived from HLA-B, e.g., HLA-B27. In other embodiments, the human or humanized MHC I is derived from HLA-A3, HLA-B7, HLA-B27, HLA-Cw6, etc.

Thus, in one aspect, the human or humanized MHC I is derived from HLA-B. In a specific embodiment, the HLA-B polypeptide is an HLA-B27. In one embodiment, the HLA-B27 polypeptide is a polypeptide encoded by HLA-B27 allele subtypes B*2701-2759. The HLA-B27 usage is commonly correlated with ankylosing spondylitis in human population. Although the present Examples describe this particular HLA sequence, any suitable HLA-B27 sequence is encompassed herein, e.g., polymorphic variants of HLA-B27 exhibited in human population, sequences with one or more conservative or non-conservative amino acid modifications, nucleic acid sequences differing from the sequence described herein due to the degeneracy of genetic code, etc.

In one aspect, a non-human animal that expresses a human HLA-B27 sequence is provided, wherein the human HLA-B27 sequence comprises one or more conservative or non-conservative modifications.

In one aspect, a non-human animal that expresses a human HLA-B27 sequence is provided, wherein the human HLA-27 sequence is at least about 85%, 90%, 95%, 96%, 97%, 98%, or 99% identical to a human HLA-B27 sequence. In a specific embodiment, the human HLA-B27 sequence is at least about 90%, 95%, 96%, 97%, 98%, or 99% identical to the human HLA-B27 sequence described in the Examples. In one embodiment, the human HLA-B27 sequence comprises one or more conservative substitutions. In one embodiment, the human HLA-B27 sequence comprises one or more non-conservative substitutions.

In one aspect, the non-human portion of the chimeric human/non-human MHC I polypeptide comprises transmembrane and/or cytoplasmic domains of the non-human MHC I polypeptide. In one embodiment, the non-human animal is a mouse, and the non-human MHC I polypeptide is selected from H-2K, H-2D, and H-2L. In one embodiment, the non-human MHC I polypeptide is H-2K, e.g., H-2Kb. In another embodiment, the non-human MHC I polypeptide is H-2D, e.g., H-2D1. Although specific H-2K and H-2D sequences are described in the Examples, any suitable H-2K or H-2D sequences, e.g., polymorphic variants, conservative/non-conservative amino acid substitutions, etc., are encompassed herein.

The non-human animal described herein may comprise in its genome a nucleotide sequence encoding a human or humanized MHC I polypeptide, e.g., chimeric human/non-human MHC I polypeptide, wherein the nucleotide sequence encoding such polypeptide is located at an endogenous non-human MHC I locus (e.g., H-2K or H-2D locus). In one aspect this results in a replacement of an endogenous MHC I gene or a portion thereof with a nucleotide sequence encoding a human or humanized MHC I polypeptide, e.g., resulting in a chimeric gene encoding a chimeric human/non-human MHC I polypeptide described herein. In one embodiment, the replacement comprises a replacement of an endogenous nucleotide sequence encoding a non-human MHC I peptide binding domain or a non-human MHC I extracellular domain with a human nucleotide sequence (e.g., HLA-A2 or HLA-B27 nucleotide sequence) encoding the same. In this embodiment, the replacement does not comprise a replacement of an MHC I sequence encoding transmembrane and/or cytoplasmic domains of a non-human MHC I polypeptide (e.g., H-2K or H-2D polypeptide). Thus, the non-human animal contains chimeric human/non-human nucleotide sequence at an endogenous non-human MHC I locus, and expresses chimeric human/non-human MHC I polypeptide from the endogenous non-human MHC I locus.

A chimeric human/non-human polypeptide may be such that it comprises a human or a non-human leader (signal) sequence. In one embodiment, the chimeric polypeptide comprises a leader sequence of a human MHC I protein, e.g., HLA-A2 protein (for instance, HLA-A2.1 leader sequence). Thus, the nucleotide sequence encoding the chimeric MHC I polypeptide may be operably linked to a nucleotide sequence encoding a human MHC I leader sequence.

In another embodiment, the chimeric polypeptide comprises a non-human leader sequence of an MHC I protein, e.g., a non-human leader sequence of an endogenous MHC I protein. In one embodiment, the chimeric polypeptide comprises a leader sequence of a non-human MHC I protein, e.g., mouse H-2D protein (for instance, mouse H-2D1 leader sequence). Thus, the nucleotide sequence encoding the chimeric MHC I polypeptide may be operably linked to a nucleotide sequence encoding a non-human MHC I leader sequence.

A chimeric human/non-human MHC I polypeptide may comprise in its human portion a complete or substantially complete extracellular domain of a human MHC I polypeptide. Thus, the human portion may comprise at least 80%, preferably at least 85%, more preferably at least 90%, e.g., 95% or more of the amino acids encoding an extracellular domain of a human MHC I polypeptide (e.g., HLA-A2 polypeptide, HLA-B27 polypeptide). In one example, substantially complete extracellular domain of the human MHC I polypeptide lacks a human MHC I leader sequence. In another example, the chimeric human/non-human MHC I polypeptide comprises a human MHC I leader sequence.

Moreover, the chimeric MHC I polypeptide may be expressed under the control of endogenous non-human regulatory elements, e.g., rodent MHC I regulatory animals. Such arrangement will facilitate proper expression of the chimeric MHC I polypeptide in the non-human animal, e.g., during immune response in the non-human animal.

The genetically modified non-human animal may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In one aspect, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

in a specific embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

Thus, in one embodiment, the invention relates to a genetically modified mouse that comprises in its genome a nucleotide sequence encoding a chimeric human/mouse MHC I polypeptide, wherein a human portion of the chimeric polypeptide comprises a peptide binding domain or an extracellular domain (e.g., a functional peptide binding or extracellular domain) of a human MHC I (e.g., human HLA-A or HLA-B, e.g., human HLA-A2 or HLA-B27 (e.g., human HLA-A2.1)). In some embodiments, the mouse does not express a peptide binding or an extracellular domain of an endogenous mouse polypeptide from its endogenous mouse locus. The peptide binding domain of the human MHC I may comprise α1 and α2 domains. Alternatively, the peptide binding domain of the human MHC I may comprise α1, α2, and α3 domains. In one aspect, the extracellular domain of the human MHC I comprises an extracellular domain of a human MHC I α chain. In one embodiment, the endogenous mouse locus is an H-2K or an H-2D locus (e.g., H-2Kb or H-2D1), and the mouse portion of the chimeric polypeptide comprises transmembrane and cytoplasmic domains of a mouse H-2K or H-2D polypeptide (e.g., H-2Kb or H-2D1), respectively.

Thus, in one embodiment, a genetically modified mouse is provided, wherein the mouse comprises at an endogenous H-2K (e.g., H-2Kb) locus a nucleotide sequence encoding a chimeric human/mouse MHC I polypeptide, wherein a human portion of the chimeric polypeptide comprises an extracellular domain of a human HLA-A2 (e.g., HLA-A2.1) polypeptide and a mouse portion comprises transmembrane and cytoplasmic domains of a mouse H-2K (e.g., H-2Kb) polypeptide. In one aspect, the mouse does not express an extracellular domain, e.g., a functional extracellular domain, of the mouse H-2K (e.g., H-2Kb) polypeptide from an endogenous MHC I locus. In one embodiment, the mouse expresses a chimeric HLA-A2/H-2K (e.g., a chimeric HLA-A2.1/H-2Kb) polypeptide from an endogenous H-2K (e.g., H-2Kb) locus. In various embodiments, expression of the chimeric gene is under control of endogenous mouse MHC class I regulatory elements. In some aspects, the mouse comprises two copies of the chimeric MHC I locus containing a nucleotide sequence encoding a chimeric HLA-A2/H-2K polypeptide; while in other aspects, the mouse comprises one copy of the chimeric MHC I locus containing a nucleotide sequence encoding a chimeric HLA-A2/H-2K polypeptide. Thus, the mouse may be homozygous or heterozygous for the nucleotide sequence encoding the chimeric HLA-A2/H-2K polypeptide.

In some embodiments described herein, a mouse is provided that comprises a chimeric MHC I locus located at an endogenous mouse H-2K locus. The chimeric locus comprises a nucleotide sequence that encodes an extracellular domain of a human HLA-A2 protein, e.g., α1, α2, and α3 domains of a human HLA-A2 gene. The chimeric locus lacks a nucleotide sequence that encodes an extracellular domain of a mouse H-2K protein (e.g., α1, α2, and α3 domains of the mouse H-2K). In one aspect, the chimeric locus lacks a nucleotide sequence that encodes a leader peptide, α1, α2, and α3 domains of a mouse H-2K; and comprises a leader peptide, α1, α2, and α3 domains of a human HLA-A2, and transmembrane and cytoplasmic domains of a mouse H-2K. The various domains of the chimeric locus are operably linked to each other such that the chimeric locus expresses a functional chimeric human/mouse MHC I protein.

In another embodiment, a genetically modified mouse is provided, wherein the mouse comprises at an endogenous H-2D (e.g., H-2D1) locus a nucleotide sequence encoding a chimeric human/mouse MHC I polypeptide, wherein a human portion of the chimeric polypeptide comprises an extracellular domain of a human HLA-B (e.g., HLA-B27) polypeptide and a mouse portion comprises transmembrane and cytoplasmic domains of a mouse H-2D (e.g., H-2D1) polypeptide. In one aspect, the mouse does not express an extracellular domain. e.g., a functional extracellular domain, of the mouse H-2D polypeptide from an endogenous MHC I locus. In one embodiment, the mouse expresses a chimeric HLA-B27/H-2D polypeptide from an endogenous H-2D locus. In various embodiments, expression of the chimeric gene is under control of endogenous mouse MHC class I regulatory elements. In some aspects, the mouse comprises two copies of the chimeric MHC I locus containing a nucleotide sequence encoding a chimeric HLA-B27/H-2D polypeptide; while in other aspects, the mouse comprises one copy of the chimeric MHC I locus containing a nucleotide sequence encoding a chimeric HLA-B27/H-2D polypeptide. Thus, the mouse may be homozygous or heterozygous for the nucleotide sequence encoding the chimeric HLA-B27/H-2D polypeptide.

In some embodiments described herein, a mouse is provided that comprises a chimeric MHC I locus located at an endogenous mouse H-2D locus. The chimeric locus comprises a nucleotide sequence that encodes an extracellular domain of a human HLA-B27 protein, e.g., α1, α2, and α3 domains of a human HLA-827 gene. The chimeric locus lacks a nucleotide sequence that encodes an extracellular domain of a mouse H-2D protein (e.g., α1, α2, and α3 domains of the mouse H-2D). In one aspect, the chimeric locus lacks a nucleotide sequence that encodes α1, α2, and α3 domains of a mouse H-2D; and comprises α1, α2, and α3 domains of a human HLA-B27, and a leader sequence and transmembrane and cytoplasmic domains of a mouse H-2D. The various domains of the chimeric locus are operably linked to each other such that the chimeric locus expresses a functional chimeric human/mouse MHC I protein.

In various embodiments, a non-human animal, e.g., a rodent (e.g., a mouse or a rat), that expresses a functional chimeric MHC I protein from a chimeric MHC I locus as described herein displays the chimeric protein on a cell surface. In one embodiment, the non-human animal expresses the chimeric MHC I protein on a cell surface in a cellular distribution that is the same as observed in a human. In one aspect, the cell displays a peptide fragment (an antigen fragment) bound to an extracellular portion (e.g., human HLA-A2 or HLA-B27 extracellular portion) of the chimeric MHC I protein. In an embodiment, the extracellular portion of such chimeric protein interacts with other proteins on the surface of said cell, e.g., β2-microglobulin.

In various embodiments, a cell displaying the chimeric MHC I protein, e.g., HLA-A2/H-2K protein or HL-B27/H-2D protein, is a nucleated cell. In various aspects, the cell is an antigen-presenting cell (APC). Although most cells in the body can present an antigen in the context of MHC I, some nonlimiting examples of antigen presenting cells include macrophages, dendritic cells, and B cells. Other antigen presenting cells, including professional and nonprofessional APCs, are known in the art, and are encompassed herein. In some embodiments, the cell displaying the chimeric MHC I protein is a tumor cell, and a peptide fragment presented by the chimeric protein is derived from a tumor. In other embodiments, the peptide fragment presented by the chimeric MHC I protein is derived from a pathogen, e.g., a bacterium or a virus.

The chimeric MHC I protein described herein may interact with other proteins on the surface of the same cell or a second cell. In some embodiments, the chimeric MHC I protein interacts with endogenous non-human proteins on the surface of said cell. The chimeric MHC I protein may also interact with human or humanized proteins on the surface of the same cell or a second cell.

On the same cell, HLA class I molecules may functionally interact with both non-human (e.g., rodent, e.g., mouse or rat) and human β2-microglobulin. Thus, in one embodiment, the chimeric MHC I protein, e.g., HLA-A2/H-2K or HLA-B27/H-2D protein, interacts with a mouse β2-microglobulin. Although interaction between some human HLA class I molecules and mouse β2-microglobulin is possible, it nevertheless may be greatly reduced in comparison to interaction between human HLA class I and human β2-microglobulin. Thus, in the absence of human β2-microglobulin, expression of human MHC I on the cell surface may be reduced. Perarnau et al. (1988) Human β2-microglobulin Specifically Enhances Cell-Surface Expression of HLA Class I Molecules in Transfected Murine Cells, J. Immunol. 141:1383-89. Other HLA molecules, e.g., HLA-B27, do not interact with mouse β2-microglobulin; see, e.g., Tishon et al. (2000) Transgenic Mice Expressing Human HLA and CD8 Molecules Generate HLA-Restricted Measles Virus Cytotoxic T Lymphocytes of the Same Specificity as Humans with Natural Measles Virus Infection, Virology 275:286-293, which reports that HLA-B27 function in transgenic mice requires both human β2-microglobulin and human CD8. Therefore, in another embodiment, the chimeric MHC I protein interacts with a human or humanized β2-microglobulin. In some such embodiments, as described herein below, the non-human animal, e.g., a rodent (e.g., a mouse or a rat), comprises in its genome a human or humanized β2-microglobulin gene, and the animal expresses a functional human or humanized β2-microglobulin polypeptide; therefore, the chimeric MHC I protein interacts with a human or humanized β2-microglobulin polypeptide.

In various aspects, the chimeric protein (e.g., HLA-A2/H-2K or HLA-B27/H-2D protein) also interacts with proteins on the surface of a second cell (through its extracellular portion). The second cell may be a cell of a non-human, e.g., a mouse, or a human origin. The second cell may be derived from the same non-human animal or the same non-human animal specie as the cell expressing the chimeric MHC I polypeptide. Nonlimiting examples of proteins with which the extracellular portion of a chimeric protein (e.g., HLA-A2/H-2K or HLA-B27/H-2D) may interact include T cell receptor (TCR) and its co-receptor CD8. Thus, a second cell may be a T cell. In addition, the extracellular portion of the chimeric MHC I protein may bind a protein on the surface of NaturalKiller (NK) cells, e.g., killer unoglobulin receptors (KIRs) on the surface of NK cells.

A T cell or NK cell may bind a complex formed between the chimeric MHC I polypeptide and its displayed peptide fragment. Such binding may result in T cell activation or inhibition of NK-mediated cell killing, respectively. One hypothesis is that NK cells have evolved to kill either infected or tumor cells that have evaded T cell mediated cytotoxicity by downregulating their MHC I complex. However, when MHC I complex is expressed on cell surface, NK cell receptors recognize it, and NK-mediated cell killing is inhibited. Thus, in some aspects, when an NK cell binds a complex formed between the chimeric MHC I polypeptide (e.g., HLA-A2/H-2K or HLA-B27/H-2D polypeptide) and a displayed peptide fragment on the surface of infected or tumor cell, the NK-mediated cell killing is inhibited.

In one example, the chimeric MHC I polypeptide described herein, e.g., a chimeric HLA-A2/H-2K or HLA-B27/H-2D polypeptide, interacts with CD8 protein on the surface of a second cell. In one embodiment, the chimeric MHC I polypeptide, e.g., HLA-A2/H-2K or HLA-B27/H-2D polypeptide, interacts with endogenous rodent (e.g., mouse or rat) CD8 protein on the surface of a second cell. In one embodiment, the second cell is a T cell. In another embodiment, the second cell is engineered to express CD8. In certain aspects, the chimeric MHC I polypeptide, e.g., HLA-A2/H-2K or HLA-B27/H-2D polypeptide, interacts with a human CD8 on the surface of the second cell (e.g., a human cell or a rodent cell). In some such embodiments, the non-human animal, e.g., a mouse or a rat, comprises a human CD8 transgene, and the mouse or the rat expresses a functional human CD8 protein.

The chimeric MHC I polypeptide described herein may also interact with a non-human (e.g., a mouse or a rat) TCR, a human TCR, or a humanized TCR on a second cell. The chimeric MHC I polypeptide may interact with an endogenous TCR (e.g., mouse or rat TCR) on the surface of a second cell. The chimeric MHC I polypeptide may also interact with a human or humanized TCR expressed on the surface of a second cell, wherein the cell is derived from the same animal or animal specie (e.g., mouse or rat) as the cell expressing the chimeric MHC I polypeptide. The chimeric MHC I polypeptide may interact with a human TCR expressed on the surface of a human cell.

In addition to genetically engineered non-human animals, a non-human embryo (e.g., a rodent embryo, e.g., mouse or a rat embryo) is also provided, wherein the embryo comprises a donor ES cell that is derived from a non-human animal (e.g., a rodent, e.g., a mouse or a rat) as described herein. In one aspect, the embryo comprises an ES donor cell that comprises the chimeric MHC I gene, and host embryo cells.

Also provided is a tissue, wherein the tissue is derived from a non-human animal (e.g., a mouse or a rat) as described herein, and expresses the chimeric MHC I polypeptide (e.g., HLA-A2/H-2K polypeptide or HLA-B27/H-2D polypeptide).

In addition, a non-human cell isolated from a non-human animal as described herein is provided. In one embodiment, the cell is an ES cell. In one embodiment, the cell is an antigen-presenting cell, e.g., dendritic cell, macrophage, B cell. In one embodiment, the cell is an immune cell. In one embodiment, the immune cell is a lymphocyte.

Also provided is a non-human cell comprising a chromosome or fragment thereof of a non-human animal as described herein. In one embodiment, the non-human cell comprises a nucleus of a non-human animal as described herein. In one embodiment, the non-human cell comprises the chromosome or fragment thereof as the result of a nuclear transfer.

In one aspect, a non-human induced pluripotent cell comprising gene encoding a chimeric MHC I polypeptide (e.g., HLA-A2/H-2K or HLA-B27/H-2D polypeptide) as described herein is provided. In one embodiment, the induced pluripotent cell is derived from a non-human animal as described herein.

In one aspect, a hybridoma or quadroma is provided, derived from a cell of a non-human animal as described herein. In one embodiment, the non-human animal is a mouse or rat.

Also provided is a method for making a genetically engineered non-human animal (e.g., a genetically engineered rodent, e.g., a mouse or a rat) described herein. The method for making a genetically engineered non-human animal results in the animal whose genome comprises a nucleotide sequence encoding a chimeric MHC I polypeptide. In one embodiment, the method results in a genetically engineered mouse, whose genome comprises at an endogenous MHC I locus, e.g., H-2K or H-2D locus, a nucleotide sequence encoding a chimeric human/mouse MHC I polypeptide, wherein a human portion of the chimeric MHC I polypeptide comprises an extracellular domain of a human HLA-A2 or human HLA-B27 and a mouse portion comprises transmembrane and cytoplasmic domains of a mouse H-2K or a mouse H-2D, respectively. In some embodiments, the method utilizes a targeting construct made using VELOCIGENE® technology, introducing the construct into ES cells, and introducing targeted ES cell clones into a mouse embryo using VELOCIMOUSE® technology, as described in the Examples. In one embodiment, the ES cells are a mix of 129 and C57BL/6 mouse strains; in another embodiment, the ES cells are a mix of BALB/c and 129 mouse strains.

Thus, a nucleotide construct used for generating genetically engineered non-human animals described herein is also provided. In one aspect, the nucleotide construct comprises: 5' and 3' non-human homology arms, a human DNA fragment comprising human HLA-A or HLA-B gene sequences, and a selection cassette flanked by recombination sites. In one embodiment, the human DNA fragment is a genomic fragment that comprises both introns and exons of a human HLA-A or HLA-B gene. In one embodiment, the non-human homology arms are homologous to a non-human MHC class I locus (e.g., a mouse H-2K or H-2D locus).

In one embodiment, the genomic fragment comprises a human HLA-A (e.g., HLA-A2) leader, an $\alpha 1$ domain, an $\alpha 2$ domain and an $\alpha 3$ domain coding sequence. In one embodiment, the human DNA fragment comprises, from 5' to 3': an HLA-A leader sequence, an HLA-A leader/al intron, an HLA-A $\alpha 1$ exon, an HLA-A $\alpha 1$-$\alpha 2$ intron, an HLA-A $\alpha 2$ exon, an HLA-A $\alpha 2$-$\alpha 3$ intron, and an HLA-A $\alpha 3$ exon.

In another embodiment, the genomic fragment comprises a human HLA-B (e.g., HLA-B27) $\alpha 1$ domain, $\alpha 2$ domain and $\alpha 3$ domain coding sequence. Thus, the nucleotide sequence for generating genetically engineered animals may also comprise a non-human, e.g., a mouse, e.g., a mouse H-2D, leader sequence. In one embodiment, the human DNA fragment comprises, from 5' to 3': a human HLA-B27 $\alpha 1$ exon, an HLA-B27 $\alpha 1$-$\alpha 2$ intron, an HLA-B27 $\alpha 2$ exon, an HLA-B27 $\alpha 2$-$\alpha 3$ intron, and an HLA-B27 $\alpha 3$ exon.

A selection cassette is a nucleotide sequence inserted into a targeting construct to facilitate selection of cells (e.g., ES cells) that have integrated the construct of interest. A number of suitable selection cassettes are known in the art. Commonly, a selection cassette enables positive selection in the presence of a particular antibiotic (e.g., Neo. Hyg. Pur. CM. Spec, etc,). In addition, a selection cassette may be flanked by recombination sites, which allow deletion of the selection cassette upon treatment with recombinase enzymes. Commonly used recombination sites are loxP and Frt, recognized by Ore and Flp enzymes, respectively, but others are known in the art.

In one embodiment, the selection cassette is located at the 5' end the human DNA fragment. In another embodiment, the selection cassette is located at the 3' end of the human DNA fragment. In another embodiment, the selection cassette is located within the human DNA fragment. In another embodiment, the selection cassette is located within an intron of the human DNA fragment. In another embodiment, the selection cassette is located within the $\alpha 2$-$\alpha 3$ intron. In yet another embodiment, the selection cassette may be located within the non-human sequence that is a part of the sequence being inserted into the genome of the non-human animal.

In one embodiment, the 5' and 3' non-human homology arms comprise genomic sequence at 5' and 3' locations of an endogenous non-human (e.g., murine) MHC class I gene locus, respectively (e.g., 5' of the first leader sequence and 3' of the $\alpha 3$ exon of the non-human MHC I gene). In another embodiment, the 5' non-human homology arm may comprise genomic sequence upstream of the al exon of the non-human MHC I gene, e.g., genomic sequence comprising the non-human leader sequence exon; in this embodiment, the chimeric human/non-human MHC I protein retains the non-human leader sequence. In one embodiment, the endogenous MHC class I locus is selected from mouse H-2K, H-2D and H-2D1, and H-2L.

In a specific embodiment, the endogenous MHC class I locus is mouse H-2K. Thus, in one aspect, a nucleotide construct is provided, comprising, from 5' to 3': a 5' homology arm containing mouse genomic sequence 5' of the endogenous mouse H-2K locus, a first human DNA fragment comprising a first genomic sequence of an HLA-A gene, a 5' recombination sequence site (e.g., loxP), a selection cassette, a 3' recombination sequence site (e.g., loxP), a second human DNA fragment comprising a second genomic sequence of an HLA-A gene and a 3' homology arm containing mouse genomic sequence 3' of an endogenous H-2K α3 exon. In one embodiment, the nucleotide construct comprises, from 5' to 3': a 5' homology arm containing mouse genomic sequence 5' of the endogenous mouse H-2K locus, a human genomic sequence including an HLA-A leader, an HLA-A leader/α1 intron sequence, an HLA-A exon, an HLA-A α1-α2 intron, an HLA-A α2 exon, a first 5' portion of an α2-α3 intron, a selection cassette flanked by recombination sites, a second 3' portion of an α2-α3 intron, an HLA-A α3 exon, and a 3' homology arm containing non-mouse genomic sequence 3' of the endogenous mouse H-2K α3 exon. In one embodiment, a 5' homology arm sequence is set forth in SEQ ID NO:1, and a 3' homology arm sequence is set forth in SEQ ID NO:2.

In another specific embodiment, the endogenous MHC class I locus is a mouse H-2D locus. Thus, in one aspect, a nucleotide construct is provided, comprising, from 5' to 3': a 5' homology arm containing mouse genomic sequence 5' of the endogenous mouse H-2D1 gene, a human DNA fragment comprising a genomic sequence of an HLA-B27 gene and a 3' homology arm containing mouse genomic sequence 3' of an endogenous H-D gene. In one embodiment, the nucleotide construct comprises, from 5' to 3': a 5' homology arm containing mouse genomic sequence 5' of the endogenous mouse H-2D gene including the leader sequence exon and the H-2D1 leader-al intron, an HLA-B27 α1 exon, an HLA-B27 α1-α2 intron, an HLA-B27 α2 exon, an HLA-B27 α2-α3 intron with a 5' IoxP site insertion, an HLA-B27 α3 exon, a mouse H-2D α3-transmembrane domain intron, a mouse transmembrane and cytoplasmic domain genomic sequence and a polyA tail, a 5' FRT site, a hygromycin cassette, a 3' FRT site, a 3' IoxP site and a 3' homology arm containing genomic sequence downstream of the mouse H-2D gene. In one embodiment, a 5' homology arm sequence spans mouse genomic sequence 49.8 kb upstream of endogenous mouse H-2D gene and includes the H-2D leader sequence, and a 3' homology arm spans mouse genomic sequence 155.6 kb downstream of endogenous mouse H-2D gene.

Upon completion of gene targeting, ES cells or genetically modified non-human animals are screened to confirm successful incorporation of exogenous nucleotide sequence of interest or expression of exogenous polypeptide. Numerous techniques are known to those skilled in the art, and include (but are not limited to) Southern blotting, long PCR, quantitative PCT (e.g., real-time PCR using TAQMAN®), fluorescence in situ hybridization, Northern blotting, flow cytometry, Western analysis, immunocytochemistry, immunohistochemistry, etc. In one example, non-human animals (e.g., mice) bearing the genetic modification of interest can be identified by screening for loss of mouse allele and/or gain of human allele using a modification of allele assay described in Valenzuela et al. (2003) High-throughput engineering of the mouse genome coupled with high-resolution expression analysis, Nature Biotech. 21(6):652-659. Other assays that identify a specific nucleotide or amino acid sequence in the genetically modified animals are known to those skilled in the art.

The disclosure also provides a method of modifying an MHC I locus of a non-human animal to express a chimeric human/non-human MHC I polypeptide described herein. In one embodiment, the invention provides a method of modifying an MHC I locus of a mouse to express a chimeric human/mouse MHC I polypeptide wherein the method comprises replacing at an endogenous MHC I locus a nucleotide sequence encoding a peptide binding domain of a mouse MHC polypeptide with a nucleotide sequence encoding a peptide binding domain of a human MHC I polypeptide. In some aspects, a nucleotide sequence of an extracellular domain of a mouse MHC I is replaced by a nucleotide sequence of an extracellular domain of a human MHC I. The mouse may fail to express the peptide binding or the extracellular domain of the mouse MHC I from an endogenous MHC I locus. In one embodiment, a nucleotide sequence of an extracellular domain of a mouse H-2K is replaced by a nucleotide sequence of an extracellular domain of a human HLA-A2, such that the modified mouse MHC I locus expresses a chimeric HLA-A2/H-2K polypeptide. In one embodiment, a nucleotide sequence of an extracellular domain of a mouse H-2D is replaced by a nucleotide sequence of an extracellular domain of a human HLA-B27, such that the modified mouse MHC I locus expresses a chimeric HLA-B27/H-2D polypeptide.

In one aspect, a method for making a chimeric human HLA class I/non-human MHC class I molecule is provided, comprising expressing in a single cell a chimeric HLA-A/H-2K or HLA-B/H-2D protein from a nucleotide construct, wherein the nucleotide construct comprises a cDNA sequence that encodes an α1, α2, and α3 domain of an HLA-A or HLA-B protein, respectively, and a transmembrane and cytoplasmic domain of a non-human H-2K or H-2D protein, e.g., mouse H-2K or H-2D protein, respectively. In one embodiment, the nucleotide construct is a viral vector; in a specific embodiment, the viral vector is a lentiviral vector. In one embodiment, the cell is selected from a CHO, COS, 293, HeLa, and a retinal cell expressing a viral nucleic acid sequence (e.g., a PERC.6™ cell).

In one aspect, a cell that expresses a chimeric human HLA Class I/non-human MHC I protein (e.g., HLA-A/H-2K or HLA-B/H-2D protein) is provided. In one embodiment, the cell comprises an expression vector comprising a chimeric MHC class I gene, wherein the chimeric MHC class I gene comprises a sequence of a human HLA-A or HLA-B gene fused in operable linkage with a sequence of a non-human H-2K or H-2D gene, e.g., mouse H-2K or H-2D gene, respectively. In one embodiment, the sequence of the human HLA-A or HLA-B gene comprises the exons that encode α1, α2 and α3 domains of an HLA-A or HLA-B protein. In one embodiment, the sequence of the non-human H-2K or H-2D gene comprises the exons that encode transmembrane and cytoplasmic domains of an H-2K or H-2D protein, respectively. In one embodiment, the cell is selected from CHO, COS, 293, HeLa, and a retinal cell expressing a viral nucleic acid sequence (e.g., a PERC.6™ cell).

A chimeric MHC class I molecule made by a non-human animal as described herein is also provided, wherein the chimeric MHC class I molecule comprises α1, α2, and α3 domains from a human HLA-A or HLA-B protein and transmembrane and cytoplasmic domains from a non-human, e.g., mouse, H-2K or H-2D protein. The chimeric HLA-A/H-2K polypeptide described herein maybe detected by anti-HLA-A antibodies. Thus, a cell displaying chimeric human/non-human HLA-A/H-2K polypeptide may be detected and/or selected using anti-HLA-A antibody. In some instances, the chimeric HLA-A2/H-2K polypeptide described herein maybe detected by an anti-HLA-A2 antibody. In another embodiment, the chimeric HLA-B/H-2D polypeptide described herein may be detected by anti-HLA-B antibodies; for example, the chimeric HLA-B27/H-2D polypeptide may be detected by anti-HLA-B27 antibodies.

Although the following Examples describe a genetically engineered animal whose genome comprises a replacement of a nucleotide sequence encoding an extracellular domain of mouse H-2K or H-2D polypeptide with the sequence encoding an extracellular domain of a human HLA-A2 at the endogenous mouse H-2K locus or human HLA-B27 at the endogenous H-2D locus, respectively, one skilled in the art would understand that a similar strategy may be used to replace other mouse MHC I loci (e.g., H-2L) with their corresponding human HLA loci (e.g., HLA-C). Thus, a non-human animal comprising in its genome a nucleotide sequence encoding a chimeric human/non-human MHC I polypeptide wherein a human portion of the polypeptide is derived from another HLA class I protein is also provided.

The replacement at multiple MHC I loci is also provided. Thus, also provided herein is a non-human animal, e.g., a rodent, e.g., a mouse, that comprises at an endogenous MHC I locus one or more, e.g., one, two, three, four, five, or six, nucleotide sequence(s) encoding a human or humanized MHC I polypeptide(s), e.g., a chimeric human/non-human (e.g., human/rodent, e.g., human/mouse) MHC I polypeptide(s). In one instance, each of the two mouse sister chromosomes 17 contains an MHC I locus that comprises H-2K, H-2L, and H-2D genes; thus, in one aspect, each sister chromosome may encode up to three chimeric human/mouse polypeptides at their endogenous genomic positions. Therefore, in one embodiment, a genetically modified non-human animal, e.g., a mouse, may comprise up to six different nucleotide sequences encoding up to six human or humanized MHC I polypeptide(s), e.g., up to six chimeric human/non-human, e.g., human/mouse, MHC I polypeptides at their endogenous MHC loci. In another instance, each of the two mouse sister chromosomes 17 contains an MHC I locus that comprises H-2K and H-2D genes; thus, in one aspect, each sister chromosome may encode up to two chimeric human/mouse polypeptides at their endogenous genomic positions; and the genetically modified non-human animal, e.g., a mouse, may comprise up to four different nucleotide sequences encoding up to four human or humanized MHC I polypeptide(s).

In one embodiment, provided herein is a mouse comprising at an endogenous MHC I locus one or more, e.g., one, two, three, four, five, or six, nucleotide sequence(s) encoding a human or humanized MHC I polypeptide(s); e.g., chimeric human/mouse MHC I polypeptide(s), wherein a human portion of the chimeric polypeptide(s) comprises an extracellular domain of a human MHC I polypeptide and wherein a mouse portion of the chimeric polypeptide comprises a transmembrane and cytoplasmic domain of a mouse MHC I polypeptide, and wherein the mouse expresses one or more, e.g., one, two, three, four, five, or six, chimeric human/mouse MHC I polypeptide(s). In one embodiment, the mouse MHC I is selected from H-2D, H-2K, and H-2L. In one embodiment, the human MHC is selected from HLA-A, HLA-B, and HLA-C.

Thus, provided herein is a mouse that comprises at an endogenous MHC I locus two nucleotide sequences encoding a chimeric human/mouse MHC I polypeptides, wherein the two nucleotide sequences encode chimeric HLA-A2/H-2K and HLA-B27/H-2D polypeptides, and wherein the mouse expresses the chimeric HLA-A2/H-2K and HLA-B27/H-2D polypeptides. In one embodiment, the nucleotide sequences encoding HLA-A2/H-2K and HLA-B27/H-2D are located at endogenous H-2K and H-2D loci, respectively. In one aspect, the mouse does not express any functional endogenous mouse MHC I polypeptides. In another aspect, the mouse retains a nucleotide sequence encoding an endogenous mouse MHC I polypeptide, e.g., expresses a functional mouse MHC I polypeptide (e.g., H-2L polypeptide).

Furthermore, provided herein is a method for generating a non-human animal, e.g., a mouse, comprising replacements at multiple endogenous MHC loci, e.g., a non-human, e.g., a mouse, comprising one or more, e.g., one, two, three, four, five, or six, nucleotide sequence(s) encoding a chimeric human/non-human, e.g., human/mouse, MHC I polypeptide(s). Due to close linkage of the various MHC I loci on mouse chromosome 17, in some embodiments, the methods comprise successive replacements at the locus. In one embodiment, the method comprises replacing a nucleotide sequence encoding a first mouse MHC I polypeptide with a nucleotide sequence encoding a first chimeric human/mouse MHC I polypeptide in an ES cell, generating a mouse expressing the first chimeric MHC I polypeptide, generating an ES cell from said mouse, replacing in said ES cell a nucleotide sequence encoding a second mouse MHC I polypeptide with a nucleotide sequence encoding a second chimeric human/mouse MHC I polypeptide, and generating a mouse expressing two chimeric human/mouse MHC I polypeptides. A mouse comprising a nucleotide sequence encoding a third chimeric human/mouse MHC I polypeptide can be generated in a similar fashion, by replacing a nucleotide sequence encoding a third mouse MHC I polypeptide with a nucleotide sequence encoding a third chimeric human/mouse MHC I polypeptide, performed in an ES cell comprising two chimeric MHC I genes. Alternatively, the method may comprise replacing a nucleotide sequence encoding a first mouse MHC I polypeptide with a nucleotide sequence encoding a first chimeric human/mouse MHC I polypeptide in an ES cell, followed by replacing in same ES cell a nucleotide sequence encoding a second mouse MHC I polypeptide with a nucleotide sequence encoding a second chimeric human/mouse MHC I polypeptide, and generating a mouse expressing two chimeric human/mouse MHC I polypeptides; a mouse comprising three chimeric human/mouse MHC I polypeptides can be generated in the same ES cell. The mouse comprising one, two, or three chimeric MHC I polypeptides generated by successive replacement may be heterozygous or homozygous for the chimeric MHC I sequences. A mouse comprising four, five, and six chimeric MHC I polypeptides may be generated by breeding two animals each comprising nucleotide sequences encoding chimeric MHC I polypeptides, resulting in an animal that, in one embodiment, is heterozygous for each of the chimeric MHC I sequences. One skilled in the art would understand that a mouse comprising two, three, or four chimeric MHC I polypeptides may also be generated by breeding rather than successive replacement; this animal may be heterozygous for all of the chimeric MHC I sequences (e.g., a mouse comprising a different chimeric gene on each of its sister chromosomes will be heterozygous for the two MHC genes, etc.).

Genetically Modified β2 Microglobulin Animals

The invention generally provides genetically modified non-human animals that comprise in their genome a nucleotide sequence encoding a human or humanized β2 microglobulin polypeptide; thus, the animals express a human or humanized β2 microglobulin polypeptide.

β2 microglobulin or the light chain of the MHC class I complex (also abbreviated "β2M") is a small (12 kDa) non-glycosylated protein, that functions primarily to stabilize the MHC I α chain. The human β2 microglobulin gene encodes a protein of 119 amino acids, with 20 N-terminal amino acids encoding a leader sequence. The mature protein comprises 99 amino acids. The gene contains 4 exons, with the first exon containing the 5' untranslated region, the entire leader sequence and the first two amino acids of the mature polypeptide; the second exon encoding the majority of the mature protein; the third exon encoding the last four amino acids of the mature protein and a stop codon; and the fourth exon containing the 3' non-translated region. Gussow et al. (1987) The β2-Microglobulin Gene. Primary Structure and Definition of the Transcriptional Unit, J. Immunol. 139: 3131-38. β2 microglobulin is non-covalently associated with MHC I, Unbound β2 microglobulin is found in body fluids, such as plasma, and is carried to the kidney for excretion. Kidney dysfunction causes accumulation of β2 microglobulin, which can be pathogenic (e.g., Dialysis Related Amyloidosis); the accumulated protein forms filamentous fibrils resembling amyloid plaques in joints and connective tissues.

In addition to Dialysis Related Amyloidosis, β2 microglobulin has been implicated in a number of other disorders. Elevated levels of β2 microglobulin were detected in lymphocytic malignancies, e.g., non-Hodgkin's lymphoma and multiple myeloma. See, e.g., Shi et al. (2009) β2 Microglobulin: Emerging as a Promising Cancer Therapeutic Target, Drug Discovery Today 14:25-30. Some other malignancies with elevated levels of β2 microglobulin include breast cancer, prostate cancer, lung cancer, renal cancer, gastrointestinal and nasopharyngeal cancers. Overexpression of β2 microglobulin has been suggested to have tumor growth promoting effects. Id. It has also been recently shown that β2 microglobulin drives epithelial to mesenchymal transition, promoting cancer bone and soft tissue metastasis in breast, prostate, lung and renal cancers. Josson et al. (2011) β2 microglobulin Induces Epitelial to Mesenchymal Transition and Confers Cancer Lethality and Bone Metastasis in Human Cancer Cells. Cancer Res. 71(7):1-11. β2 microglobulin interacts with a non-classical MHC I member, hemochromatosis (HFE) protein, and with the transferrin receptor, and modulates iron homeostasis. Id. Involvement of β2 microglobulin in other hallmarks of malignancy (self-renewal, angiogenesis enhancement, resistance to treatment) is widely documented in the art.

Mice deficient in β2 microglobulin have been reported. See, Koller et al. (1990) Normal development of mice deficient in β2m, MHC class I proteins, and CD8+ T cells, Science 248: 1227-1230. As reported in Koller et al., these mice appeared healthy, however, MHC class I expression was not detected. Further, most T cell populations appeared normal in some tissues, while a marked decrease of CD8+ T cells was observed in others. This purported lack of MHC I expression disagrees with previous results obtained by Allen et al. ((1986) β2 microglobulin Is Not Required for Cell Surface Expression of the Murine Class I Histocompatibility Antigen H-2D$^b$ or of a Truncated H-2D$^b$, Proc. Natl. Acad. Sci. USA 83:7447-7451). Allen et al. reported that β2 microglobulin was not absolutely required for cell surface expression of all MHC I complexes, because cells lacking β2 microglobulin were able to express H-2D$^b$. However, the function of H-2D$^b$ in these cells was presumably compromised, and conformation of H-2D$^b$ was different from the native protein, which explains the inability of Koller and colleagues to detect this protein using antibodies against native H-2D$^b$. However, cells lacking β2 microglobulin can reportedly present endogenous antigen to CD8+ T cells (including exogenous CD8+ T cells from normal mice), and β2 microglobulin is reportedly not required in order to develop high levels of H-2$^d$ MHC class I-restricted CD8+ CTLs in response to antigen challenge in mice, although it is required in order to sustain an effective immune response. Quinn et al. (1997) Virus-Specific, CD8+ Major Histocompatibility Complex Class I-Restricted Cytotoxic T Lymphocytes in Lymphocytic Choriomeningitis Virus-infected β2-Microglobulin-Deficient Mice, J. Virol. 71:8392-8396. It is of note that the ability to generate high levels of such T cells in the absence of β2 microglobulin is reportedly limited to an H-2$^d$ MHC class I-restricted response. β2 microglobulin deficient mice have been reported to have a host of dramatic characteristics, such as, for example, an increased susceptibility to some parasitic diseases, an increased susceptibility to hepatitis infections, a deficiency in iron metabolism, and an impaired breeding phenotype. Cooper et al. (2007) An impaired breeding phenotype in mice with a genetic deletion of Beta-2 microglobulin and diminished MHC class I expression: Role in reproductive fitness, Biol. Reprod. 77:274-279.

Mice that express human β2 microglobulin as well as human HLA class I molecules (i.e., HLA-B7) on a randomly inserted transgene have been reported. Chamberlain et al. (1988) Tissue-specific and cell surface expression of human major histocompatibility complex class I heavy (HLA-B7) and light (β2-microglobulin) chain genes in transgenic mice, Proc. Natl. Acad. Sci. USA 85:7690-7694. The expression of human HLA class I was consistent with that of endogenous class I with a marked decrease in the liver. Id. The expression of human β2 microglobulin was also consistent with the endogenous β2 microglobulin, while expression of the human HLA class I molecule was increased 10- to 17-fold in double transgenic mice, Id. However, the authors did not attempt a replacement of a mouse endogenous β2 microglobulin locus with a human β2 microglobulin locus.

Therefore, disclosed herein is a genetically engineered non-human animal (e.g., a rodent, e.g., a mouse or a rat) whose genome comprises a nucleotide sequence encoding a human or humanized β2 microglobulin polypeptide. In one aspect, the animal does not express an endogenous non-human β2 microglobulin from an endogenous non-human β2 microglobulin locus. In some embodiments, the nucleotide sequence encodes a β2 microglobulin polypeptide that is partially human and partially non-human, e.g., it contains some amino acids that correspond to human and some amino acids that correspond to non-human β2 microglobulin. In one aspect, the non-human animal does not express an endogenous non-human β2 microglobulin polypeptide from an endogenous non-human locus, and only expresses the human or humanized β2 microglobulin polypeptide. In one example, the non-human animal does not express a complete endogenous non-human β2 microglobulin polypeptide but only expresses a portion of a non-human endogenous β2 microglobulin polypeptide from an endogenous β2 microglobulin locus. Thus, in various embodiments, the animal does not express a functional non-human β2 microglobulin polypeptide from an endogenous non-human β2 microglobulin locus. In a specific aspect, the nucleotide sequence encoding the human or humanized β2 microglobulin is located at an endogenous non-human β2 microglobulin locus. In one aspect, the animal comprises two copies of β2 microglobulin locus comprising a nucleotide sequence encoding a human or humanized β2 microglobulin polypeptide. In another aspect, the animal comprises one copy of β2 microglobulin locus comprising a nucleotide sequence encoding a human or humanized β2 microglobulin polypeptide. Thus, the animal may be homozygous or heterozygous for β2 microglobulin locus comprising a nucleotide sequence that encodes a human or humanized β2 microglobulin polypeptide. The nucleotide sequence of the human or humanized β2 microglobulin may be derived from a collection of β2 microglobulin sequences that are naturally found in human populations. In various embodiments, the genetically engineered non-human animal of the invention comprises in its germline a nucleotide sequence encoding a human or humanized β2 microglobulin. In one embodiment, a nucleotide sequence encoding a human or humanized β2 microglobulin polypeptide comprises a nucleotide sequence encoding a polypeptide comprising a human β2 microglobulin amino acid sequence. In one embodiment, the polypeptide is capable of binding to an MHC I protein.

The nucleotide sequence encoding the human or humanized β2 microglobulin polypeptide may comprise nucleic acid residues corresponding to the entire human β2 microglobulin gene. Alternatively, the nucleotide sequence may comprise nucleic acid residues encoding amino acid sequence set forth in amino acids 21-119 of a human β2 microglobulin protein (i.e., amino acid residues corresponding to the mature human β2 microglobulin). In an alternative embodiment, the nucleotide sequence may comprise nucleic acid residues encoding amino acid sequence set forth in amino acids 23-115 of a human β2 microglobulin protein, for example, amino acid sequence set forth in amino acids 23-119 of a human β2 microglobulin protein. The nucleic and amino acid sequences of human β2 microglobulin are described in Gussow et al., supra, incorporated herein by reference.

Thus, the human or humanized β2 microglobulin polypeptide may comprise amino acid sequence set forth in amino acids 23-115 of a human β2 microglobulin polypeptide, e.g., amino acid sequence set forth in amino acids 23-119 of a human β2 microglobulin polypeptide, e.g., amino acid sequence set forth in amino acids 21-119 of a human β2 microglobulin polypeptide. Alternatively, the human β2 microglobulin may comprise amino acids 1-119 of a human β2 microglobulin polypeptide.

In some embodiments, the nucleotide sequence encoding a human or humanized β2 microglobulin comprises a nucleotide sequence set forth in exon 2 to exon 4 of a human β2 microglobulin gene. Alternatively, the nucleotide sequence comprises nucleotide sequences set forth in exons 2, 3, and 4 of a human β2 microglobulin gene. In this embodiment, the nucleotide sequences set forth in exons 2, 3, and 4 are operably linked to allow for normal transcription and translation of the gene. Thus, in one embodiment, the human sequence comprises a nucleotide sequence corresponding to exon 2 to exon 4 of a human β2 microglobulin gene. In a specific embodiment, the human sequence comprises a nucleotide sequence corresponding to exon 2 to about 267 bp after exon 4 of a human β2 microglobulin gene. In a specific embodiment, the human sequence comprises about 2.8 kb of a human β2 microglobulin gene.

Thus, the human or humanized β2 microglobulin polypeptide may be encoded by a nucleotide sequence comprising nucleotide sequence set forth in exon 2 to exon 4 of a human β2 microglobulin, e.g., nucleotide sequence corresponding to exon 2 to exon 4 of a human β2 microglobulin gene. Alternatively, the polypeptide may be encoded by a nucleotide sequence comprising nucleotide sequences set forth in exons 2, 3, and 4 of a human β2 microglobulin gene. In a specific embodiment, the human or humanized β2 microglobulin polypeptide is encoded by a nucleotide sequence corresponding to exon 2 to about 267 bp after exon 4 of a human β2 microglobulin gene. In another specific embodiment, the human or humanized polypeptide is encoded by a nucleotide sequence comprising about 2.8 kb of a human β2 microglobulin gene. As exon 4 of the β2 microglobulin gene contains the 5' untranslated region, the human or humanized polypeptide may be encoded by a nucleotide sequence comprising exons 2 and 3 of the β2 microglobulin gene.

It would be understood by those of ordinary skill in the art that although specific nucleic acid and amino acid sequences to generate genetically engineered animals are described in the present examples, sequences of one or more conservative or non-conservative amino acid substitutions, or sequences differing from those described herein due to the degeneracy of the genetic code, are also provided.

Therefore, a non-human animal that expresses a human β2 microglobulin sequence is provided, wherein the β2 microglobulin sequence is at least about 85%, 90%, 95%, 96%, 97%, 98%, or 99% identical to a human β2 microglobulin sequence. In a specific embodiment, the β2 microglobulin sequence is at least about 90%, 95%, 96%, 97%, 98%, or 99% identical to the human β2 microglobulin sequence described in the Examples. In one embodiment, the human β2 microglobulin sequence comprises one or more conservative substitutions. In one embodiment, the human β2 microglobulin sequence comprises one or more non-conservative substitutions.

In addition, provided are non-human animals wherein the nucleotide sequence encoding a human or humanized β2 microglobulin protein also comprises a nucleotide sequence set forth in exon 1 of a non-human β2 microglobulin gene. Thus, in a specific embodiment, the non-human animal comprises in its genome a nucleotide sequence encoding a human or humanized β2 microglobulin wherein the nucleotide sequence comprises exon 1 of a non-human β2 microglobulin and exons 2, 3, and 4 of a human β2 microglobulin gene. Thus, the human or humanized β2 microglobulin polypeptide is encoded by exon 1 of a non-human β2 microglobulin gene and exons 2, 3, and 4 of a human β2 microglobulin gene (e.g., exons 2 and 3 of a human β2 microglobulin gene).

Similarly to a non-human animal comprising a nucleotide sequence encoding a chimeric human/non-human MHC I polypeptide, the non-human animal comprising a nucleotide sequence encoding a human or humanized β2 microglobulin may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). In some embodiments of the invention, the non-human animal is a mammal. In a specific embodiment, the non-human animal is a murine, e.g., a rodent (e.g., a mouse or a rat). In one embodiment, the animal is a mouse.

Thus, in some aspects, a genetically engineered mouse is provided, wherein the mouse comprises a nucleotide sequence encoding a human or a humanized β2 microglobulin polypeptide as described herein. A genetically engineered mouse is provided, wherein the mouse comprises at its endogenous β2 microglobulin locus a nucleotide sequence encoding a human or humanized β2 microglobulin polypeptide (e.g., a human or substantially human β2 microglobulin polypeptide). In some embodiments, the mouse does not express an endogenous β2 microglobulin polypeptide (e.g., a functional endogenous β2 microglobulin polypeptide) from an endogenous β2 microglobulin locus. In some embodiments, the genetically engineered mouse comprises a nucleotide sequence comprising exon 1 of a mouse β2 microglobulin gene and exons 2, 3, and 4 of a human β2 microglobulin gene. In some embodiments, the mouse expresses the human or humanized β2 microglobulin polypeptide.

In one aspect, a modified non-human β2 microglobulin locus is provided that comprises a heterologous β2 microglobulin sequence. In one embodiment, the heterologous β2 microglobulin sequence is a human or a humanized sequence.

In one embodiment, the modified locus is a rodent locus. In a specific embodiment, the rodent locus is selected from a mouse or rat locus. In one embodiment, the non-human locus is modified with at least one human β2 microglobulin coding sequence.

In one embodiment, the heterologous β2 microglobulin sequence is operably linked to endogenous regulatory elements, e.g., endogenous promoter and/or expression control sequence. In a specific embodiment, the heterologous β2 microglobulin sequence is a human sequence and the human sequence is operably linked to an endogenous promoter and/or expression control sequence.

In one aspect, a modified non-human β2 microglobulin locus is provided that comprises a human sequence operably linked to an endogenous promoter and/or expression control sequence.

In various aspects, the human or humanized β2 microglobulin expressed by a genetically modified non-human animal, or cells, embryos, or tissues derived from a non-human animal, preserves all the functional aspects of the endogenous and/or human β2 microglobulin. For example, it is preferred that the human or humanized β2 microglobulin binds the α chain of MHC I polypeptide (e.g., endogenous non-human or human MHC I polypeptide). The human or humanized β2 microglobulin polypeptide may bind, recruit or otherwise associate with any other molecules, e.g., receptor, anchor or signaling molecules that associate with endogenous non-human and/or human β2 microglobulin (e.g., HFE, etc.).

In addition to genetically modified animals (e.g., rodents, e.g., mice or rats), also provided is a tissue or cell, wherein the tissue or cell is derived from a non-human animal as described herein, and comprises a heterologous β2 microglobulin gene or β2 microglobulin sequence, i.e., nucleotide and/or amino acid sequence. In one embodiment, the heterologous β2 microglobulin gene or β2 microglobulin sequence is a human or humanized β2 microglobulin gene or human or humanized β2 microglobulin sequence. Preferably, the cell is a nucleated cell. The cell may be any cell known to express MHC I complex, e.g., an antigen presenting cell. The human or humanized β2 microglobulin polypeptide expressed by said cell may interact with endogenous non-human MHC I (e.g., rodent MHC I), to form a functional MHC I complex. The resultant MHC I complex may be capable of interacting with a T cell, e.g., a cytotoxic T cell. Thus, also provided is an in vitro complex of a cell from a non-human animal as described herein and a T cell.

Also provided are non-human cells that comprise human or humanized β2 microglobulin gene or sequence, and an additional human or humanized sequence, e.g., chimeric MHC I polypeptide presently disclosed. In such an instance, the human or humanized β2 microglobulin polypeptide may interact with, e.g., a chimeric human/non-human MHC I polypeptide, and a functional MHC I complex may be formed. In some aspects, such complex is capable of interacting with a TCR on a T cell, e.g., a human or a non-human T cell. Thus, also provided in an in vitro complex of a cell from a non-human animal as described herein and a human or a non-human T cell.

Another aspect of the disclosure is a rodent embryo (e.g., a mouse or a rat embryo) comprising a heterologous β2 microglobulin gene or β2 microglobulin sequence as described herein. In one embodiment, the embryo comprises an ES donor cell that comprises the heterologous β2 microglobulin gene or β2 microglobulin sequence, and host embryo cells. The heterologous β2 microglobulin gene or β2 microglobulin sequence is a human or humanized β2 microglobulin gene or β2 microglobulin sequence.

This invention also encompasses a non-human cell comprising a chromosome or fragment thereof of a non-human animal as described herein (e.g., wherein the chromosome or fragment thereof comprises a nucleotide sequence encoding a human or humanized β2 microglobulin polypeptide). The non-human cell may comprise a nucleus of a non-human animal as described herein. In one embodiment, the non-human cell comprises the chromosome or fragment thereof as the result of a nuclear transfer.

In one aspect, a non-human induced pluripotent cell comprising a heterologous β2 microglobulin gene or β2 microglobulin sequence is provided. In one embodiment, the induced pluripotent cell is derived from a non-human animal as described herein. In one embodiment, the heterologous β2 microglobulin gene or β2 microglobulin sequence is a human or humanized gene or sequence.

Also provided is a hybridoma or quadroma, derived from a cell of a non-human animal as described herein. In one embodiment, the non-human animal is a mouse or rat.

The disclosure also provides methods for making a genetically engineered non-human animal (e.g., a genetically engineered rodent, e.g., a mouse or a rat) described herein. The methods result in an animal whose genome comprises a nucleotide sequence encoding a human or humanized β2 microglobulin polypeptide. In one aspect, the methods result in a genetically engineered mouse, whose genome comprises at an endogenous β2 microglobulin locus a nucleotide sequence encoding a human or humanized β2 microglobulin polypeptide. In some instances, the mouse does not express a functional mouse β2 microglobulin from an endogenous mouse β2 microglobulin locus. In some aspects, the methods utilize a targeting construct made using VELOCIGENE® technology, introducing the construct into ES cells, and introducing targeted ES cell clones into a mouse embryo using VELOCIMOUSE® technology, as described in the Examples. In one embodiment, the ES cells are mix of 129 and C57BL/6 mouse strains; in another embodiment, the ES cells are a mix of BALB/c and 129 mouse strains.

Also provided is a nucleotide construct used for generating genetically engineered non-human animals. The nucleotide construct may comprise: 5' and 3' non-human homology arms, a human DNA fragment comprising human β2 microglobulin sequences, and a selection cassette flanked by recombination sites. In one embodiment, the human DNA fragment is a genomic fragment that comprises both introns and exons of a human β2 microglobulin gene. In one embodiment, the non-human homology arms are homologous to a non-human β2 microglobulin locus. The genomic fragment may comprise exons 2, 3, and 4 of the human β2 microglobulin gene. In one instance, the genomic fragment comprises, from 5' to 3': exon 2, intron, exon 3, intron, and exon 4, all of human β2 microglobulin sequence. The selection cassette may be located anywhere in the construct outside the β2 microglobulin coding region, e.g., it may be located 3' of exon 4 of the human β2 microglobulin. The 5' and 3' non-human homology arms may comprise genomic sequence 5' and 3' of endogenous non-human β2 microglobulin gene, respectively. In another embodiment, the 5' and 3' non-human homology arms comprise genomic sequence 5' of exon 2 and 3' of exon 4 of endogenous non-human gene, respectively.

Another aspect of the invention relates to a method of modifying a β2 microglobulin locus of a non-human animal (e.g., a rodent, e.g., a mouse or a rat) to express a human or humanized β2 microglobulin polypeptide described herein. One method of modifying a β2 microglobulin locus of a mouse to express a human or humanized β2 microglobulin polypeptide comprises replacing at an endogenous β2 microglobulin locus a nucleotide sequence encoding a mouse β2 microglobulin with a nucleotide sequence encoding the human or humanized β2 microglobulin polypeptide. In one embodiment of such method, the mouse does not express a functional β2 microglobulin polypeptide from an endogenous mouse β2 microglobulin locus. In some specific embodiments, the nucleotide sequence encoding the human or humanized β2 microglobulin polypeptide comprises nucleotide sequence set forth in exons 2 to 4 of the human β2 microglobulin gene. In other embodiments, the nucleotide sequence encoding the human or humanized β2 microglobulin polypeptide comprises nucleotide sequences set forth in exons 2, 3, and 4 of the human β2 microglobulin gene.

Genetically Modified MHC I/β2 Microglobulin Animals

In various embodiments, the invention generally provides genetically modified non-human animals that comprise in their genome nucleotide sequences encoding both human or humanized MHC I and β2 microglobulin polypeptides; thus, the animals express both human or humanized MHC I and β2 microglobulin polypeptides.

Functional differences arise in the use of mixed human/non-human system components. HLA class I binds β2 microglobulin tighter than mouse class I. Bernabeu (1984) β2-microgobulin from serum associates with MHC class I antigens on the surface of cultured cells. Nature 308:642-645. Attempts to abrogate functional differences are reflected in the construction of particular humanized MHC mice. H-2 class I and class 2 knockout mice (in a mouse β2 microglobulin KO background) that express a randomly integrated human HLA-A2.1/HLA-DR1 chimeric transgene having an α1 and α2 of human HLA-A2.1, and α3 of mouse H-2D$^b$, attached at its N-terminal via a linker to the C-terminus of human β2-microglobulin have been developed. See, e.g., Pajot et al, (2004) A mouse model of human adaptive immune functions: HLA-A2.1-/HLA-DR1-transgenic H-2 class I-/class II-knockout mice, Eur. J. Immunol. 34:3060-3069. These mice reportedly generate antigen-specific antibody and CTL responses against hepatitis B virus, whereas mice merely transgenic for HLA-A2.1 or H-2 class I/class II knockout mice do not. The deficiency of mice that are merely transgenic for the genes presumably stems from the ability of such mice to employ endogenous class I and/or class II genes to circumvent any transgene, an option not available to MHC knockout mice. However, the mice may express at least H-2D$^b$, presumably due to breedings into the mouse β2 microglobulin knockout mouse background (see, Pajot et al., supra; which apparently comprised an intact endogenous class I and class II locus).

Cell surface expression of the chimeric fusion with human β2 microglobulin is reportedly lower than endogenous MHC expression, but survivability/rate of NK killing is not reported, nor is the rate of NK self-killing. Pajot et al., supra. Some improvement in CD8+ T cell numbers was observed over MHC class I-deficient β2-microglobulin knockout mice (2-3% of total splenocytes, vs. 0.6-1% in the β2 KO mice). However, T cell variable region usage exhibited altered profiles for BV 5.1, BV 5.2, and BV 11 gene segments. Both CD8+ and CD4+T cell responses were reportedly restricted to the appropriate hepatitis B antigen used to immunize the mice, although at least two mice killed cells bearing either of the antigens, where the mice were immunized with only one antigen, which might be due to a lack of NK cell inhibition or lack of NK cell selectivity.

As mentioned above, mice transgenic for both human MHC I and human β2 microglobulin comprise a nucleotide sequence encoding a chimeric MHC I/β2 microglobulin protein, wherein the MHC I and β2 microglobulin portions are contained within a single polypeptide chain, resulting in MHC I α chain and β2 microglobulin being covalently linked to each other and thereby tethered at the cell surface. A mouse which comprises in its genome two independent nucleotide sequences, one encoding a human or humanized MHC I polypeptide and the other encoding a human or humanized β2 microglobulin polypeptide is provided. The mouse provided herein would express an MHC I complex that more closely resembles an MHC I complex present in nature, wherein MHC I α chain and β2 microglobulin are provided on two separate polypeptide chains with β2 microglobulin non-covalently associating with the MHC I α chain.

Thus, the present disclosure provides a non-human animal comprising in its genome: a first nucleotide sequence encoding a human or humanized MHC I polypeptide, and a second nucleotide sequence encoding a human or humanized β2 microglobulin polypeptide. In one aspect, provided is a non-human animal comprising in its genome: (a) a first nucleotide sequence encoding a chimeric human/non-human MHC I polypeptide, wherein the human portion of the chimeric polypeptide comprises a peptide binding domain or an extracellular domain of a human MHC I (e.g., HLA-A, HLA-B, or HLA-C; e.g., HLA-A2 or HLA-B27), and (b) a second nucleotide sequence encoding a human or humanized β2 microglobulin polypeptide.

The first nucleotide sequence may be located at an endogenous non-human MHC I locus such that the animal comprises in its genome a replacement at the MHC I locus of all or a portion of endogenous MHC I gene (e.g., a portion encoding a peptide binding domain or an extracellular domain) with the corresponding human MHC I sequence. Thus, the animal may comprise at an endogenous MHC I locus a nucleotide sequence encoding an extracellular domain of a human MHC I (e.g., HLA-A, HLA-B, or HLA-C; e.g., HLA-A2 or HLA-B27) and transmembrane and cytoplasmic domains of endogenous non-human MHC I (e.g., H-2K, H-2D, H-2L, e.g., H-2K or H-2D). In one aspect, the animal is a mouse, and the first nucleotide sequence comprises a nucleotide sequence encoding an extracellular domain of a human HLA-A2 (e.g., HLA-A2.1) and transmembrane and cytoplasmic domains of a mouse H-2K (e.g., H-2Kb). In another aspect, the animal is a mouse and the first nucleotide sequence comprises a nucleotide sequence encoding an extracellular domain of a human HLA-B27 and transmembrane and cytoplasmic domains of a mouse H-2D (e.g., H-2D1).

The second nucleotide sequence may be located at an endogenous non-human β2 microglobulin locus such that the animal comprises in its genome a replacement at the β2 microglobulin locus of all or a portion of endogenous β2 microglobulin gene with the corresponding human β2 microglobulin sequence. The second nucleotide sequence may comprise a nucleotide sequence set forth in exon 2 to exon 4 of a human β2 microglobulin gene. Alternatively, the second nucleotide sequence may comprise nucleotide sequences set forth in exons 2, 3, and 4 of a human β2 microglobulin gene. In this embodiment, nucleotide sequences are operably linked to each other. The second nucleotide sequence may further comprise the sequence of exon 1 of a non-human β2 microglobulin gene.

In one aspect, the animal does not express a functional MHC I from an endogenous non-human MHC I locus (e.g., does not express either a functional peptide binding domain or a functional extracellular domain of the endogenous MHC I); in one aspect, the animal does not express a functional β2 microglobulin polypeptide from an endogenous non-human β2 microglobulin locus. In some aspects, the animal is homozygous for both an MHC I locus comprising a nucleotide sequence encoding a chimeric human/non-human MHC I polypeptide and a β2 microglobulin locus comprising a nucleotide sequence encoding a human or humanized β2 microglobulin. In other aspects, the animal is heterozygous for both an MHC I locus comprising a nucleotide sequence encoding a chimeric human/non-human MHC I polypeptide and a β2 microglobulin locus comprising a nucleotide sequence encoding a human or humanized β2 microglobulin.

Preferably, the first and the second nucleotide sequences are operably linked to endogenous expression control elements (e.g., promoters, enhancers, silencers, etc.).

Various other embodiments of the first and second nucleotide sequences (and the polypeptides they encode) encompassed herein may be readily understood from the embodiments described throughout the specification, e.g., those described in the sections related to genetically engineered MHC I animals and genetically engineered β2 microglobulin animals.

In one aspect, the disclosure provides a mouse comprising in its genome (a) a first nucleotide sequence encoding a chimeric human/mouse MHC I polypeptide (specifically, either HLA-A2/H-2K or HLA-B27/H-2D polypeptide), wherein the human portion of the chimeric polypeptide comprises an extracellular domain of a human HLA-A2 or HLA-B27 and the mouse portion comprises transmembrane and cytoplasmic domains of a mouse H-2K or mouse H-2D, respectively, and (b) a second nucleotide sequence encoding a human or humanized β2 microglobulin polypeptide (e.g., wherein the nucleotide sequence comprises a nucleotide sequence set forth in axon 2 to exon 4 of the human β2 microglobulin gene or nucleotide sequences set forth in exon 2, 3, and 4 of the human β2 microglobulin gene), wherein the first nucleotide sequence is located at an endogenous H-2K or H-2D locus, and the second sequence is located at an endogenous β2 microglobulin locus. In one embodiment, the mouse does not express functional H-2K or H-2D and mouse β2 microglobulin polypeptides from their respective endogenous loci. In one embodiment, the mouse expresses both the chimeric human/mouse MHC I polypeptide and the human or humanized β2 microglobulin polypeptide.

As shown in the following Examples, animals genetically engineered to co-express both the human or humanized MHC I and β2 microglobulin displayed increased expression of chimeric MHC class I on cell surface in comparison to animals humanized for MHC I alone. In some embodiments, co-expression of human or humanized MHC I and β2 microglobulin increases cell surface expression of human or humanized MHC I by more than about 10%, e.g., more than about 20%, e.g., about 50% or more, e.g., about 70%, over the expression of human or humanized MHC I in the absence of human or humanized β2 microglobulin.

The disclosure also provides a method of making genetically engineered non-human animals (e.g., rodents, e.g., rats or mice) whose genome comprises a first and a second nucleotide sequence as described herein. The method generally comprises generating a first genetically engineered non-human animal whose genome comprises a first nucleotide sequence described herein (i.e., a human or humanized MHC I sequence), generating a second genetically engineered non-human animal whose genome comprises a second nucleotide sequence described herein (i.e., a human or humanized β2 microglobulin sequence), and breeding the first and the second animal to obtain progeny whose genome contains both nucleotide sequences. In one embodiment, the first and the second animal are heterozygous for the first and the second nucleotide sequence, respectively. In one embodiment, the first and the second animal are homozygous for the first and the second nucleotide sequence, respectively. In one embodiment, the first and second animals are generated through replacement of endogenous non-human loci with the first and the second nucleotide sequences, respectively. In one aspect, the first and the second animals are generated through utilization of constructs generated via VELOCIGENE® technology, and introducing targeted ES cell clones bearing such constructs into an embryo (e.g., a rodent embryo, e.g., a mouse or a rat embryo) via the VELOCIMOUSE® method.

In yet another aspect, the invention provides a genetically modified non-human animal (e.g., rodent, e.g., mouse or rat) that comprises in its genome nucleotide sequence(s) encoding one or more (e.g., one, two, three, four, five, six) chimeric human/non-human (e.g., chimeric human/mouse) MHC I polypeptide(s) and a nucleotide sequence encoding a human or humanized β2 microglobulin polypeptide. Various aspects of the chimeric human/non-human MHC I polypeptide(s) and the human or humanized β2 microglobulin are disclosed throughout the specification and would be clear from the disclosure to those skilled in the art. Methods for generating non-human animals comprising nucleotide sequence(s) encoding one or more (e.g., one, two, three, four, five, six) chimeric human/non-human (e.g., chimeric human/mouse) MHC I polypeptide(s) and a nucleotide sequence encoding a human or humanized β2 microglobulin polypeptide are also provided herein.

Use of Genetically Modified Animals

In various embodiments, the genetically modified non-human animals described herein make APCs with human or humanized MHC I and/or β2 microglobulin on the cell surface and, as a result, present peptides derived from cytosolic proteins as epitopes for CTLs in a human-like manner, because substantially all of the components of the complex are human or humanized. The genetically modified non-human animals of the invention can be used to study the function of a human immune system in the humanized animal; for identification of antigens and antigen epitopes that elicit immune response (e.g., T cell epitopes, e.g., unique human cancer epitopes), e.g., for use in vaccine development; for identification of high affinity T cells to human pathogens or cancer antigens (i.e., T cells that bind to antigen in the context of human MHC I complex with high avidity), e.g., for use in adaptive T cell therapy; for evaluation of vaccine candidates and other vaccine strategies; for studying human autoimmunity; for studying human infectious diseases; and otherwise for devising better therapeutic strategies based on human MHC expression.

The MHC I complex binds peptides and presents them on cell surface. Once presented on the surface in the context of such a complex, the peptides are recognizable by T cells. For example, when the peptide is derived from a pathogen or other antigen of interest (e.g., a tumor antigen), T cell recognition can result in T cell activation, macrophage killing of cells bearing the presented peptide sequence, and B cell activation of antibodies that bind the presented sequence.

T cells interact with cells expressing MHC I complex through the peptide-bound MHC class I ectodomain and the T cell's CD8 ectodomain. CD8+ T cells that encounter APC's that have suitable antigens bound to the MHC class I molecule will become cytotoxic T cells. Thus, antigens that in the context of MHC class I bind with high avidity to a T cell receptor are potentially important in the development of treatments for human pathologies. However, presentation of antigens in the context of mouse MHC I is only somewhat relevant to human disease, since human and mouse MHC complexes recognize antigens differently, e.g., a mouse MHC I may not recognize the same antigens or may present different epitopes than a human MHC I. Thus, the most relevant data for human pathologies is obtained through studying the presentation of antigen epitopes by human MHC I.

Thus, in various embodiments, the genetically engineered animals of the present invention are useful, among other things, for evaluating the capacity of an antigen to initiate an immune response in a human, and for generating a diversity of antigens and identifying a specific antigen that may be used in human vaccine development.

In one aspect, a method for determining antigenicity in a human of a peptide sequence is provided, comprising exposing a genetically modified non-human animal as described herein to a molecule comprising the peptide sequence, allowing the non-human animal to mount an immune response, and detecting in the non-human animal a cell that binds a sequence of the peptide presented by a chimeric human/non-human MHC I, or a humanized MHC I complex (comprising a chimeric human/non-human MHC I and a human or humanized β2 microglobulin) as described herein.

In one aspect, a method for determining whether a peptide will provoke a cellular immune response in a human is provided, comprising exposing a genetically modified non-human animal as described herein to the peptide, allowing the non-human animal to mount an immune response, and detecting in the non-human animal a cell that binds a sequence of the peptide by a chimeric human/non-human MHC class I molecule as described herein. In one embodiment, the non-human animal following exposure comprises an MHC class I-restricted CD8+ cytotoxic T lymphocyte (CTL) that binds the peptide. In one embodiment, the CTL kills a cell bearing the peptide.

In one aspect, a method for identifying a human CTL epitope is provided, comprising exposing a non-human animal as described herein to an antigen comprising a putative CTL epitope, allowing the non-human animal to mount an immune response, isolating from the non-human animal an MHC class I-restricted CD8+ CTL that binds the epitope, and identifying the epitope bound by the MHC class I-restricted CD8+ CTL.

In one aspect, a method is provided for identifying an HLA class I-restricted peptide whose presentation by a human cell and binding by a human lymphocyte (e.g., human T cell) will result in cytotoxicity of the peptide-bearing cell, comprising exposing a non-human animal (or MHC class I-expressing cell thereof) as described herein to a molecule comprising a peptide of interest, isolating a cell of the non-human animal that expresses a chimeric human/non-human class I molecule that binds the peptide of interest, exposing the cell to a human lymphocyte that is capable of conducting HLA class I-restricted cytotoxicity, and measuring peptide-induced cytotoxicity.

In one aspect, a method is provided for identifying an antigen that generates a cytotoxic T cell response in a human, comprising exposing a putative antigen to a mouse as described herein, allowing the mouse to generate an immune response, and identifying the antigen bound by the HLA class I-restricted molecule.

In one embodiment, the antigen comprises a bacterial or viral surface or envelope protein. In one embodiment, the antigen comprises an antigen on the surface of a human tumor cell. In one embodiment, the antigen comprises a putative vaccine for use in a human. In one embodiment, the antigen comprises a human epitope that generates antibodies in a human. In another embodiment, the antigen comprises a human epitope that generates high affinity CTLs that target the epitope/MHC I complex.

In one aspect, a method is provided for determining whether a putative antigen contains an epitope that upon exposure to a human immune system will generate an HLA class I-restricted immune response, e.g., HLA-A-restricted immune response (e.g., HLA-A2-restricted response) or HLA-B-restricted response (e.g., HLA-B27-restricted response), comprising exposing a mouse as described herein to the putative antigen and measuring an antigen-specific HLA class I-restricted, HLA-A- or HLA-B-restricted (e.g., HLA-A2-restricted or HLA-B27-restricted) immune response in the mouse.

In one embodiment, the putative antigen is selected from a biopharmaceutical or fragment thereof, a non-self protein, a surface antigen of a non-self cell, a surface antigen of a tumor cell, a surface antigen of a bacterial or yeast or fungal cell, a surface antigen or envelope protein of a virus.

In addition, the genetically engineered non-human animals described herein may be useful for identification of T cell receptors, e.g., high-avidity T cell receptors, that recognize an antigen of interest, e.g., a tumor or another disease antigen. The method may comprise: exposing the non-human animal described herein to an antigen, allowing the non-human animal to mount an immune response to the antigen, isolating from the non-human animal a T cell comprising a T cell receptor that binds the antigen presented by a human or humanized MHC I, and determining the sequence of said T cell receptor.

In one aspect, a method for identifying a T cell receptor variable domain having high affinity for a human tumor antigen is provided, comprising exposing a mouse comprising humanized MHC I α1, α2, and α3 domains (e.g., HLA-A2 or HLA-B27 α1, α2, and α3 domains) to a human tumor antigen; allowing the mouse to generate an immune response; and, isolating from the mouse a nucleic acid sequence encoding a T cell receptor variable domain, wherein the T cell receptor variable domain binds the human tumor antigen with a $K_D$ of no higher than about 1 nanomolar.

In one embodiment, the mouse further comprises a replacement at the endogenous mouse T cell receptor variable region gene locus with a plurality of unrearranged human T cell receptor variable region gene segments, wherein the unrearranged human T cell receptor variable region gene segments recombine to encode a chimeric human-mouse T cell receptor gene comprising a human variable region and a mouse constant region. In one embodiment, the mouse comprises a human CD8 transgene, and the mouse expresses a functional human CD8 protein.

T cell receptors having high avidity to tumor antigens are useful in cell-based therapeutics. T cell populations with high avidity to human tumor antigens have been prepared by exposing human T cells to HLA-A2 that has been mutated to minimize CD8 binding to the α3 subunit, in order to select only those T cells with extremely high avidity to the tumor antigen (i.e., T cell clones that recognize the antigen in spite of the inability of CD8 to bind α3). See, Pittet et al. (2003) α3 Domain Mutants of Peptide/MHC Class I Multimers Allow the Selective Isolation of High Avidity Tumor-Reactive CD8 T Cells, J. Immunol. 171:1844-1849. The non-human animals, and cells of the non-human animals, are useful for identifying peptides that will form a complex with human HLA class I that will bind with high avidity to a T cell receptor, or activate a lymphocyte bearing a T cell receptor.

Antigen/HLA class I binding to a T cell, or activation of a T cell, can be measured by any suitable method known in the art. Peptide-specific APC-T cell binding and activation are measurable. For example, T cell engagement of antigen-presenting cells that express HLA-A2 reportedly causes PIP2 to accumulate at the immunosynapse, whereas cross-linking MHC class I molecules does not. See, Fooksman et al. (2009) Cutting Edge: Phosphatidylinositol 4,5-Bisphosphate Concentration at the APC Side of the Immunological Synapse Is Required for Effector T Cell Function, J. Immunol. 182:5179-5182.

Functional consequences of the interaction of a lymphocyte bearing a TCR, and a class I-expressing APC, are also measurable and include cell killing by the lymphocyte. For example, contact points on the α2 subunit of HLA-A2 by CD8+ CTLs reportedly generate a signal for Fas-independent killing. HLA-A2-expressing Jurkat cells apoptose when contacted (by antibodies) at epitopes on the HLA-A2 molecule known (from crystallographic studies) to contact CD8, without any apparent reliance on the cytoplasmic domain. See, Pettersen et al. (1998) The TCR-Binding Region of the HLA Class I α2 Domain Signals Rapid Fas-Independent Cell Death: A Direct Pathway for T Cell-Mediated Killing of Target Cells? J. Immunol. 160:4343-4352. It has been postulated that the rapid killing induced by HLA-A2 α2 contact with a CD8 of a CD8+ CTL may primarily be due to this Fas-independent HLA-A2-mediated pathway (Id.), as distinguished from TCR-independent α3 domain-mediated killing—which by itself can induce apoptosis (see, Woodle et al, (1997) Anti-human class I MHC antibodies induce apoptosis by a pathway that is distinct from the Fas antigen-mediated pathway, J. Immunol. 158:2156-2164).

The consequence of interaction between a T cell and an APC displaying a peptide in the context of MHC I can also be measured by a T cell proliferation assay. Alternatively, it can be determined by measuring cytokine release commonly associated with activation of immune response. In one embodiment, IFNγ ELISPOT can be used to monitor and quantify CD8+ T cell activation.

As described herein, CD8+ T cell activation can be hampered in the genetically modified non-human animals described herein due to species-specific binding of CD8 to MHC I. For embodiments where a species-specific CD8 interaction is desired, a cell of a genetically modified animal as described herein (e.g., a rodent, e.g., a mouse or a rat) is exposed (e.g., in vitro) to a human cell, e.g., a human CD8-bearing cell, e.g., a human T cell. In one embodiment, an MHC class I-expressing cell of a mouse as described herein is exposed in vitro to a T cell that comprises a human CD8 and a T cell receptor. In a specific embodiment, the T cell is a human T cell. In one embodiment, the MHC class I-expressing cell of the mouse comprises a peptide bound to a chimeric human/mouse MHC I or a humanized MHC I complex (which includes human β2 microglobulin), the T cell is a human T cell, and the ability of the T cell to bind the peptide-displaying mouse cell is determined. In one embodiment, activation of the human T cell by the peptide-displaying mouse cell is determined. In one embodiment, an in vitro method for measuring activation of a human T cell by the peptide-displaying cell is provided, comprising exposing a mouse or a mouse cell as described herein to an antigen of interest, exposing a cell from said mouse or said mouse cell (presumably bearing a peptide derived from the antigen in complex with human or humanized MHC I) to a human T cell, and measuring activation of the human T cell. In one embodiment, the method is used to identify a T cell epitope of a human pathogen or a human neoplasm. In one embodiment, the method is used to identify an epitope for a vaccine.

In one embodiment, a method is provided for determining T cell activation by a putative human therapeutic, comprising exposing a genetically modified animal as described herein to a putative human therapeutic (or e.g., exposing a human or humanized MHC I-expressing cell of such an animal to a peptide sequence of the putative therapeutic), exposing a cell of the genetically modified animal that displays a human or humanized MHC I/peptide complex to a T cell comprising a human T cell receptor and a CD8 capable of binding the cell of the genetically modified animal, and measuring activation of the human T cell that is induced by the peptide-displaying cell of the genetically modified animal.

In various embodiments, a complex formed between a human or humanized MHC class I-expressing cell from an animal as described herein is made with a T cell that comprises a human CD8 sequence, e.g., a human T cell, or a T cell of a non-human animal that comprises a transgene that encodes human CD8. Mice transgenic for human CD8 are known in the art. Tishon et al. (2000) Trangenic Mice Expressing Human HLA and CD8 Molecules Generate HLA-Restricted Measles Virus Cytotoxic T Lymphocytes of the Same Specificity as Humans with Natural Measles Virus Infection, Virology 275(2):286-293; also, LaFace et al. (1995) Human CD8 Transgene Regulation of HLA Recognition by Murine T Cells, J. Exp. Med. 182:1315-1325.

In addition to the ability to identify antigens and antigen epitopes from human pathogens or neoplasms, the genetically modified animals of the invention can be used to identify autoantigens of relevance to human autoimmune diseases, e.g., type I diabetes, multiple sclerosis, etc. For example, Takaki et al. ((2006) HLA-A*0201-Restricted T Cells from Humanized NOD Mice Recognize Autoantigens of Potential Clinical Relevance to Type 1 Diabetes, J. Immunol. 176:3257-65) describe the utility of NOD mice bearing HLA/β2 microglobulin monochain in identifying type 1 diabetes autoantigens. Also, the genetically modified animals of the invention can be used to study various aspects of human autoimmune disease. As some polymorphic alleles of human MHC I are known to be associated with development of certain diseases, e.g., autoimmune diseases (e.g., Graves' disease, myasthenia gravis, psoriasis, etc.; see Bakker et al. (2006) A high-resolution HLA and SNP haplotype map for disease association studies in the extended human MHC, Nature Genetics 38:1166-72 and Supplementary Information and International MHC and Autoimmunity Genetics Network (2009) Mapping of multiple susceptibility variants within the MHC region for 7 immune-mediated diseases, Proc. Natl. Acad. Sci. USA 106:18680-85, both incorporated herein by reference), a genetically modified animal of the invention comprising a humanized MHC I locus including such an allele may be useful as an autoimmune disease model. In one embodiment, the disease allele is HLA-B27, and the disease is ankylosing spondylitis or reactive arthritis; thus, in one embodiment, the animal used for the study of these diseases comprises a human or humanized HLA-B27. Other human disease alleles are known, e.g., HLA class I alleles associated with HIV, Ebola infection, etc., and these alleles or combination of alleles may be useful in for disease model creation in a genetically modified animal described herein.

In addition, the genetically modified animals of the invention and the human or humanized HLA molecules expressed by the same can be used to test antibodies that block antigen presentation by human HLA molecules associated with human disease progression. Thus, provided herein is a method of determining whether an antibody is capable of blocking presentation of an antigen by an HLA molecule linked to a human disease, e.g., a human disease described above, comprising exposing a cell expressing a human or humanized HLA described herein to a test antibody and determining whether the test antibody is capable of blocking the presentation of the antigen by a human or humanized HLA to immune cells (e.g., to T cells), e.g., by measuring its ability to block human or humanized HLA-restricted immune response. In one embodiment, the method is conducted in an animal expressing the human or humanized HLA. e.g., an animal expressing disease-associated human or humanized HLA that serves as a disease model for the disease.

Other aspects of cellular immunity that involve MHC I complexes are known in the art; therefore, genetically engineered non-human animals described herein can be used to study these aspects of immune biology. For instance, binding of TCR to MHC class I is modulated in vivo by additional factors. Leukocyte immunoglobulin-like receptor subfamily B member (LILRB1, or LIR-1) is expressed on MHC Class I-restricted CTLs and down-regulates T cell stimulation by binding a specific determinant on the α3 subunit of MHC class I molecules on APCs. Structural studies show that the binding site for LIR-1 and CD8 overlap, suggesting that inhibitory LIR-1 competes with stimulatory CD8 for binding with MHC class I molecules. Willcox et al. (2003) Crystal structure of HLA-A2 bound to LIR-1, a host and viral major histocompatibility complex receptor, Nature Immunology 4(9):913-919; also, Shirioshi et al. (2003) Human inhibitory receptors Ig-like transcript 2 (ILT2) and ILT4 compete with CD8 for MHC class I binding and bind preferentially to HLA-G, Proc. Natl. Acad. Sci. USA 100(15):8856-8861. LIR-1 transduces inhibitory signals through its (intracellular) immunoreceptor tyrosine-based inhibitory motif (ITIM). In NK cells, studies have shown that KIRs (inhibitory killer cell Ig-like receptors) lacking ITIMs (normally incapable of inhibition) can inhibit in the presence of LIR-1 (presumably through the LIR-1 ITIM) bound to the α3 domain of an MHC class I molecule (see, Kirwin et al. (2005) Killer Cell Ig-Like Receptor-Dependent Signaling by Ig-Like Transcript 2 (ILT2/CD85j/LILRB1/LIR-1) J. Immunol. 175:5006-5015), suggesting cooperation between LIR-1 bound to MHC class I and KIRs and thus a role for HLA α3 domain binding in modulating NK cell inhibition.

As described above, MHC molecules interact with cells that do not express a TCR. Among these cells are NK cells, NK cells are cytotoxic lymphocytes (distinguished from CTLs, or cytotoxic T lymphocytes) that play a central role in the cellular immune response, and in particular innate immunity, NK cells are the first line of defense against invading microorganisms, viruses, and other non-self (e.g., tumor) entities. NK cells are activated or inhibited through surface receptors, and they express CD8 but do not express TCRs. NK cells can interact with cells that express MHC class I, but interaction is through the CD8-binding α3 domain rather than the TCR-binding, peptide-bearing $\alpha_1$ and $\alpha_2$ domains. A primary function of NK cells is to destroy cells that lack sufficient MHC class I surface protein.

Cross-linking MHC class I molecules on the surface of human natural killer (NK) cells results in intracellular tyrosine phosphorylation, migration of the MHC class I molecule from the immunosynapse, and down-regulation of tumor cell killing. Rubio et al. (2004) Cross-linking of MHC class I molecules on human NK cells inhibits NK cell function, segregates MHC I from the NK cell synapse, and induces intracellular phosphotyrosines, J. Leukocyte Biol. 76:116-124.

Another function of MHC class I in NK cells is apparently to prevent self-killing. NK cells bear both activating receptor 2B4 and the 2B4 ligand CD48; MHC class I appears to bind 2B4 and prevent its activation by CD48. Betser-Cohen (2010) The Association of MHC Class I Proteins with the 2B4 Receptor Inhibits Self-Killing of Human NK Cells, J. Immunol. 184:2761-2768.

Thus, the genetically engineered non-human animals described herein can be used to study these non-TCR or non-CTL mediated processes and to design approaches for their modulation.

EXAMPLES

The invention will be further illustrated by the following nonlimiting examples. These Examples are set forth to aid in the understanding of the invention but are not intended to, and should not be construed to, limit its scope in any way. The Examples do not include detailed descriptions of conventional methods that would be well known to those of ordinary skill in the art (molecular cloning techniques, etc.). Unless indicated otherwise, parts are parts by weight, molecular weight is average molecular weight, temperature is indicated in Celsius, and pressure is at or near atmospheric.

Example 1. Construction and Characterization of Genetically Modified HLA-A2 Mice Example 1.1: Expression of HLA-A2/H-2K in MG87 Cells A viral construct containing a chimeric HLA-A2/H-2K gene sequence (FIG. 4A) was made using standard molecular cloning techniques known to a skilled artisan in order to analyze chimeric human/mouse MHC I expression in transfected cells.

Figure 4:
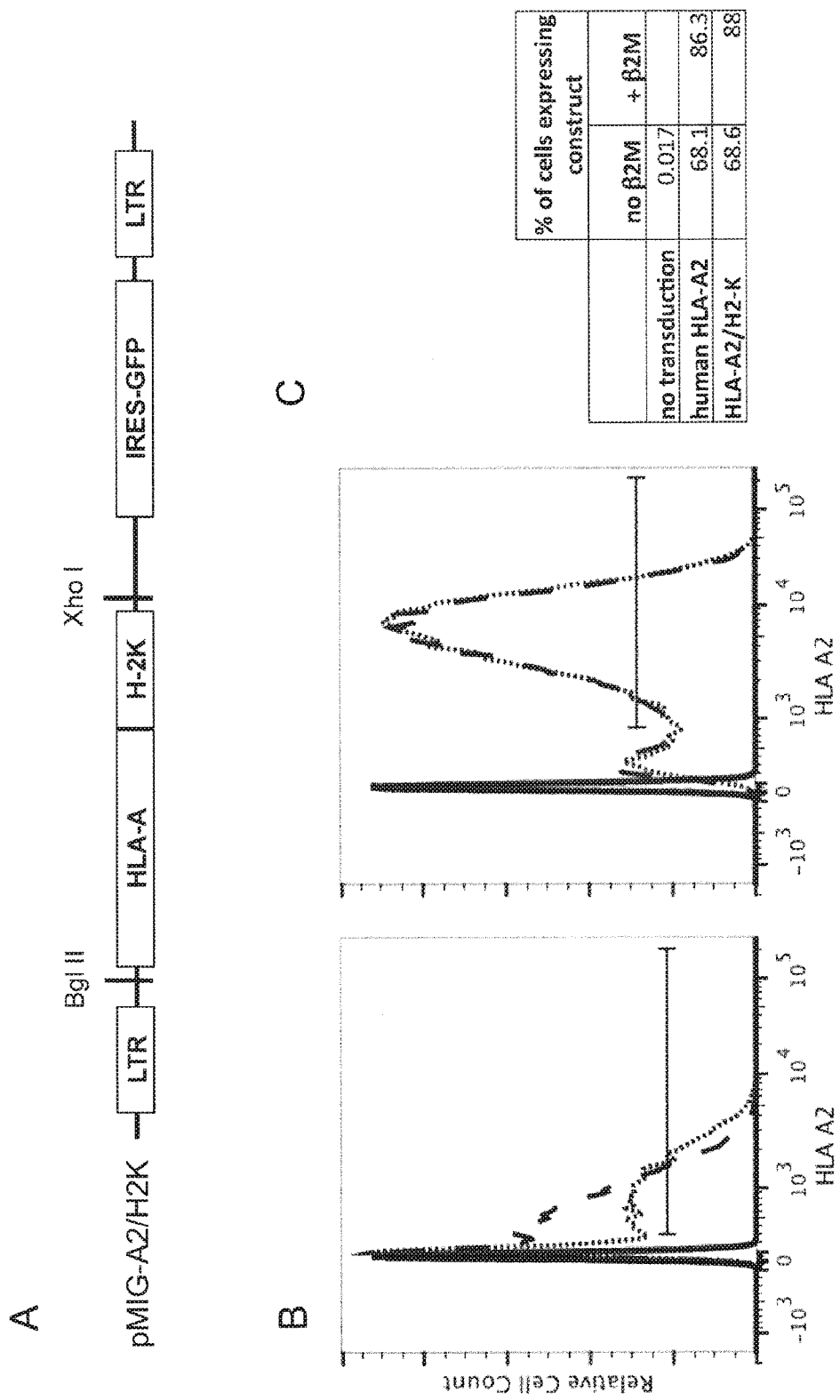
FIG. 4 illustrates a viral vector construct containing a cDNA encoding a chimeric HLA-A/H-2K polypeptide with an IRES-GFP reporter (A); and histograms comparing expression of human HLA-A2 in MG87 cells transduced with HLA-A2 (dashed line), HLA-A2/H-2K (dotted line), or no transduction (solid line) either alone (left) or co-transduced with humanized β2 microglobulin (right) (B). Data from horizontal gates presented graphically in (B) is illustrated as percent of cells expressing the construct in the table in (C).

Briefly, a chimeric human HLA-A/mouse H-2K viral construct was made using the exon sequences encoding the α1, α2 and α3 domains of the α chain and cloning them in frame with the mouse coding sequences for the transmembrane and cytoplasmic domains from the H-2K gene (FIG. 4A, pMIG-HLA-A2/H2K). As illustrated in FIG. 4, the construct contained an IRES-GFP reporter sequence, which allowed for determining if the construct was able to express in cells upon transfection.

Viruses containing the chimeric construct described above were made and propagated in human embryonic kidney 293 (293T) cells. 293 T cells were plated on 10 cm dishes and allowed to grow to 95% confluency. A DNA transfection mixture was prepared with 25 µg of pMIG-HLA-A2/H2K, pMIG-human HLA-A2, or pMIG-humanized β2 microglobulin, and 5 µg of pMDG (envelope plasmid), 15 µg of pCL-Eco (packaging construct without packaging signal ψ), 1 mL of Opti-MEM (Invitrogen). Added to this 1 mL DNA mixture was 80 µL of Lipofectamine-2000 (Invitrogen) in 1 mL of Opti-MEM, which was previously mixed together and allowed to incubate at room temperature for 5 minutes. The Lipofectamine/DNA mixture was allowed to incubate for an additional 20 minutes at room temperature, and then was added to 10 cm dishes, and the plates were incubated at 37° C. Media from the cells was collected after 24 hours and a fresh 10 mL of R10 (RPMI 1640+10% FBS) media was added to the cells. This media exchange was repeated twice. After a total of four days, the collected media was pooled, centrifuged and passed through a sterile filter to remove cellular debris.

The propagated viruses made above were used to transduce MG87 (mouse fibroblast) cells, MG87 cells from a single T-75 flask were washed once with PBS. 3 mL of 0.25% Trypsin EDTA was added to the cells and allowed to incubate at room temperature for three minutes. 7 mL of D10 (high glucose DMEM; 10% Fetal Bovine Serum) was added to the cells/trypsin mixture and transferred to a 15 mL tube to centrifuge at 1300 rpm for five minutes. After centrifuging the cells, the media was aspirated and the cells resuspended in 5 mL D10. Cells were counted and ~3.0×10$^5$ cells were placed per well in a 6-well plate. pMIG-human HLA-A2 or pMIG-HLA-A2/H-2K either alone or with pMIG-humanized β2 microglobulin virus were added to the wells, with non-transduced cells as a control. Cells were incubated at 37° C. with 5% CO$_2$ for 2 days. Cells were prepared for FACS analysis (using anti-HLA-A2 antibody, clone BB7.2) for HLA-A2 expression with or without β2 microglobulin.

The graphs (FIG. 4B), as well as the table summarizing the data obtained from the graphs (FIG. 4C) demonstrate that co-transduction with humanized β2 microglobulin increases the expression of human HLA-A2 or chimeric human/non-human HLA-A2/H-2K, as demonstrated by the shift of curves to the right.

Example 1.2. Engineering a Chimeric HLA-A2/H-2K Locus

The mouse H-2K gene was humanized in a single step by construction of a unique targeting vector from human and mouse bacterial artificial chromosome (BAC) DNA using VELOCIGENE® technology (see, e.g., U.S. Pat. No. 6,586,251 and Valenzuela et al, (2003) High-throughput engineering of the mouse genome coupled with high-resolution expression analysis. Nat. Biotech. 21(6): 652-659). DNA from mouse BAC clone RP23-173k21 (Invitrogen) was modified by homologous recombination to replace the genomic DNA encoding the α1, α2 and α3 domains of the mouse H-2K gene with human genomic DNA encoding the α1, α2 and α3 subunits of the human HLA-A gene (FIG. 5).

Briefly, the genomic sequence encoding the mouse the α1, α2 and α3 subunits of the H-2K gene is replaced with the human genomic DNA encoding the α1, α2 and α3 domains of the human HLA-A*0201 gene in a single targeting event using a targeting vector comprising a hygromycin cassette flanked by loxP sites with a 5' mouse homology arm containing sequence 5' of the mouse H-2K locus including the 5' untranslated region (UTR; 5' homology arm is set forth in SEQ ID NO: 1) and a 3' mouse homology arm containing genomic sequence 3' of the mouse H-2K α3 coding sequence (3' homology arm is set forth in SEQ ID NO: 2).

Figure 5:
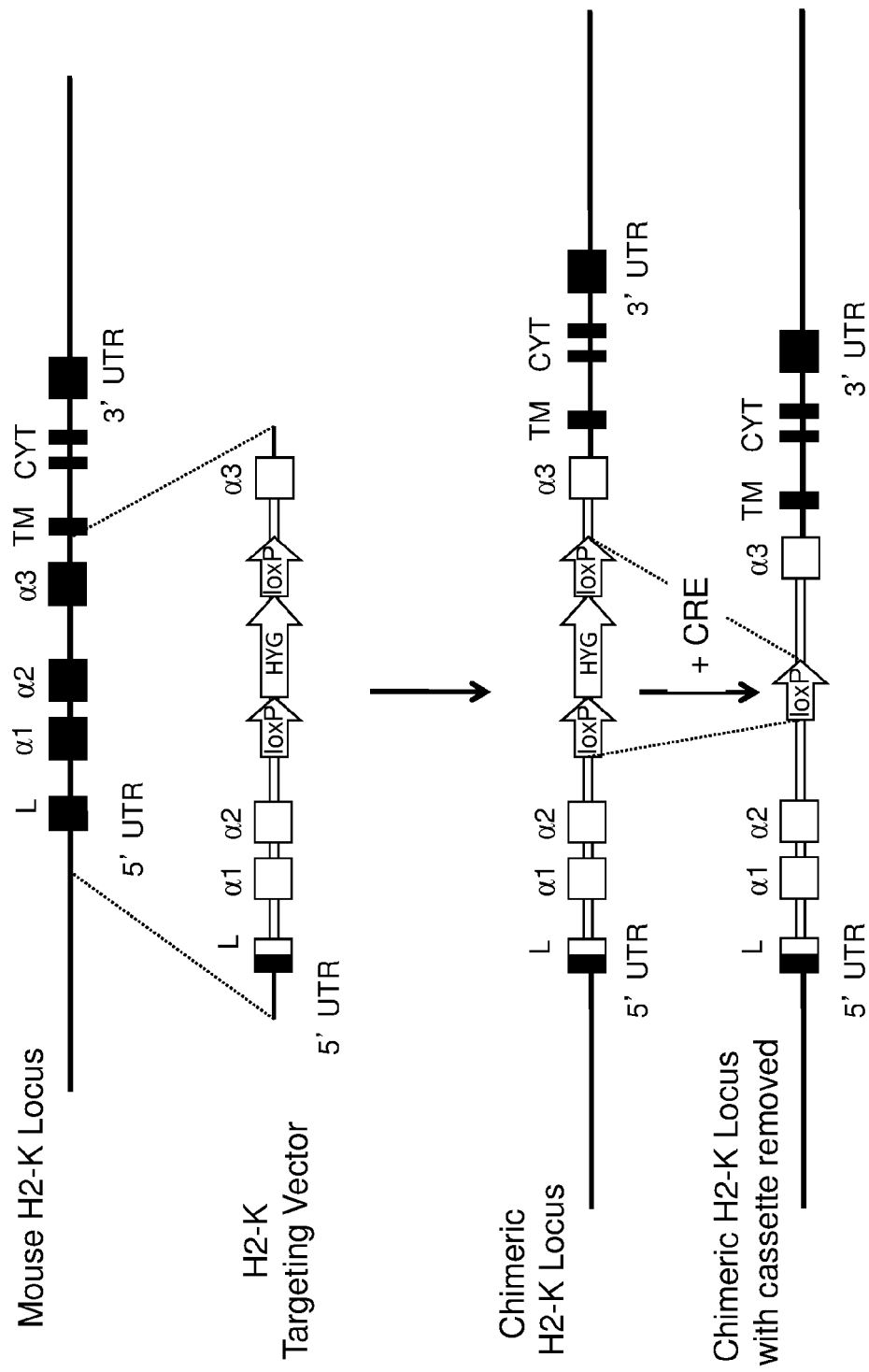
FIG. 5 is a schematic diagram (not to scale) of the targeting strategy used for making a chimeric H-2K locus that expresses an extracellular region of a human HLA-A2 protein. Mouse sequences are represented in black and human sequences are represented in white. L=leader, UTR=untranslated region, TM=transmembrane domain, CYT=cytoplasmic domain, HYG=hygromycin.

The final construct for targeting the endogenous H-2K gene locus from 5' to 3' included (1) a 5' homology arm containing ~200 bp of mouse genomic sequence 5' of the endogenous H-2K gene including the 5'UTR, (2) ~1339 bp of human genomic sequence including the HLA-A*0201 leader sequence, the HLA-A*0201 leader/α1 intron, the HLA-A*0201 exon, the HLA-A*0201 α1-α2 intron, the HLA-A*0201 α2 exon, ~316 bp of the 5' end of the α2-α3 intron, (3) a 5' loxP site, (4) a hygromycin cassette, (5) a 3' loxP site, (6) ~580 bp of human genomic sequence including ~304 bp of the 3' end of the α2-α3 intron, the HLA-A*0201 α3 exon, and (7) a 3' homology arm containing ~200 bp of mouse genomic sequence including the intron between the mouse H-2K α3 and transmembrane coding sequences (see FIG. 5 for schematic representation of the H-2K targeting vector). The sequence of 149 nucleotides at the junction of the mouse/human sequences at the 5' of the targeting vector is set forth in SEQ ID NO: 3, and the sequence of 159 nucleotides at the junction of the human/mouse sequences at the 3' of the targeting vector is set forth in SEQ ID NO:4. Homologous recombination with this targeting vector created a modified mouse H-2K locus containing human genomic DNA encoding the α1, α2 and α3 domains of the HLA-A*0201 gene operably linked to the endogenous mouse H-2K transmembrane and cytoplasmic domain coding sequences which, upon translation, leads to the formation of a chimeric human/mouse MHC class I protein.

The targeted BAC DNA was used to electroporate mouse F1H4 ES cells to create modified ES cells for generating mice that express a chimeric MHC class I protein on the surface of nucleated cells (e.g., T and B lymphocytes, macrophages, neutrophils). ES cells containing an insertion of human HLA sequences were identified by a quantitative TAQMAN™ assay. Specific primer sets and probes were designed for detecting insertion of human HLA sequences and associated selection cassettes (gain of allele, GOA) and loss of endogenous mouse sequences (loss of allele, LOA). Table 1 identifies the names and locations detected for each of the probes used in the quantitative PCR assays.

TABLE 1

Probes Used For Confirming Chimeric HLA-A2/H-2K Gene

| Probe | Assay | Region Detected by Probe | Sequence | SEQ ID NO |
|---|---|---|---|---|
| HYG | GOA | Hygromycin cassette | ACGAGCGGGT TCGGCCCATT C | 5 |

TABLE 1-continued

Probes Used For Confirming Chimeric HLA-A2/H-2K Gene

| Probe | Assay | Region Detected by Probe | Sequence | SEQ ID NO |
|---|---|---|---|---|
| 1665H1 | GOA | Human HLA-A2 α2-α3 intron | AGTCCTTCAG CCTCCACTCA GGTCAGG | 6 |
| 1665H2 | GOA | Human HLA-A2 α2 exon | TACCACCAGT ACGCCTACGA CGGCA | 7 |
| 5112H2 | GOA | Human HLA-A2 α2-α3 intron | CACTCTCTGGTACAGGAT | 8 |

The selection cassette may be removed by methods known by the skilled artisan. For example, ES cells bearing the chimeric human/mouse MHC class I locus may be transfected with a construct that expresses Cre in order to remove the "loxed" hygromycin cassette introduced by the insertion of the targeting construct containing human HLA-A*0201 gene sequences (See FIG. 5). The hygromycin cassette may optionally be removed by breeding to mice that express Cre recombinase. Optionally, the hygromycin cassette is retained in the mice.

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech, 25(1):91-99), VELOCIMICE® (F0 mice fully derived from the donor ES cell) independently bearing a chimeric MHC class I gene were identified by genotyping using a modification of allele assay (Valenzuela et al., supra) that detects the presence of the unique human HLA-A*0201 gene sequences.

Example 1.3. In Vivo Expression of Chimeric HLA-A/H-2K in Genetically Modified Mice A heterozygous mouse carrying a genetically modified H-2K locus as described in Example 1.2 was analyzed for expression of the chimeric HLA-A/H-2K protein in the cells of the animal.

Figure 6A:
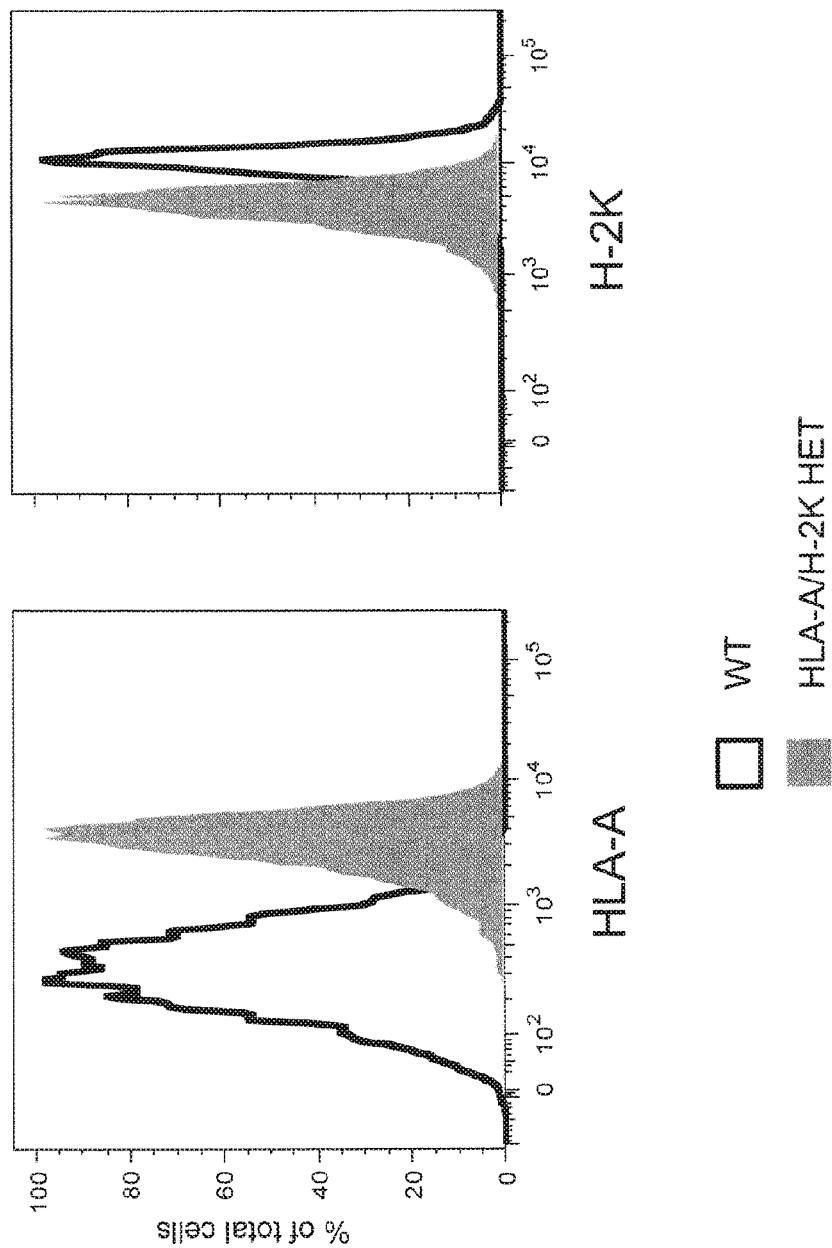
FIG. 6A demonstrates expression (% total cells) of HLA-A2 (left) and H-2K (right) in cells isolated from either a wild-type (WT) mouse or a heterozygous mouse carrying the chimeric HLA-A2/H-2K locus (HLA-A/H-2K HET).
Figure 6B:
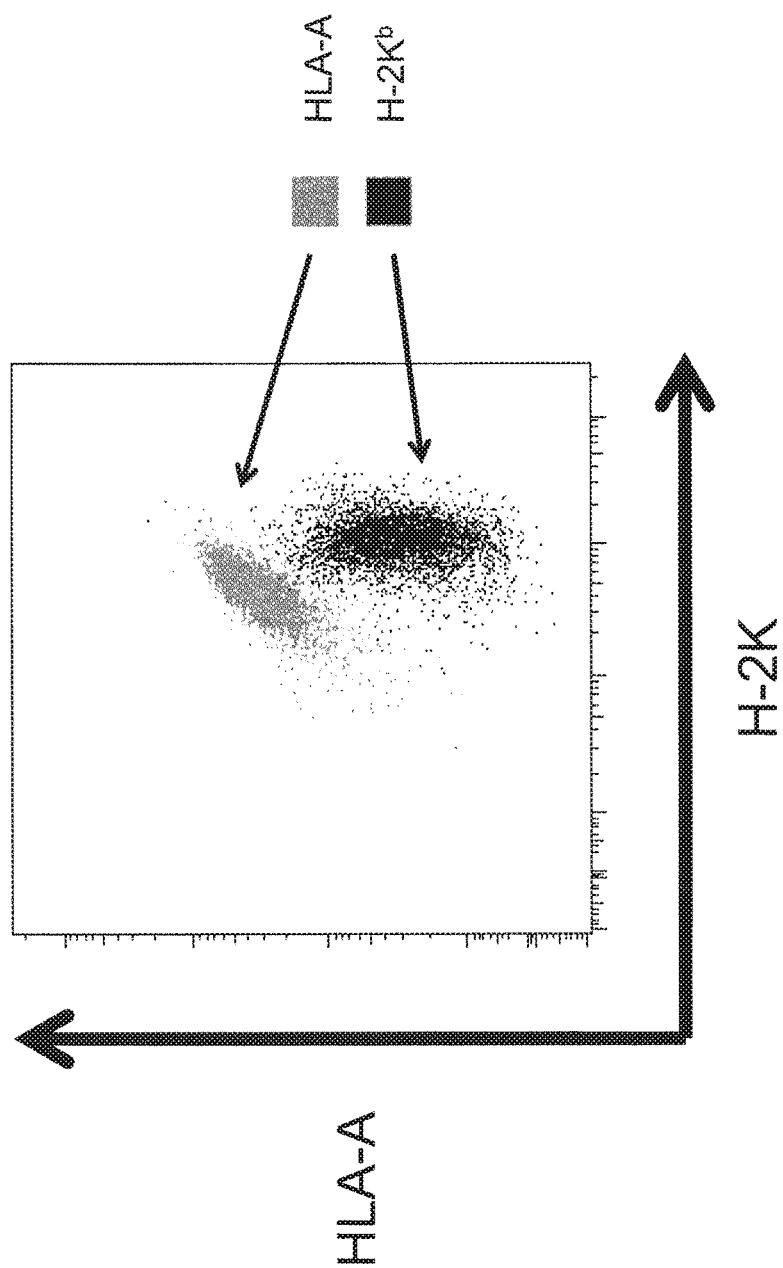
FIG. 6B is a dot plot of in viva expression of the chimeric HLA-A2/H-2K protein in a heterozygous mouse harboring a chimeric HLA-A2/H-2K locus.

Blood was obtained separately from a wild-type and a HLA-A/H-2K chimeric heterozygote (A2/H2K) mouse. Cells were stained for human HLA-A2 with a phycoerythrin-conjugated (PE) anti-HLA-A antibody, and exposed to an allophycocyanin-conjugated anti-H-2K$^b$ antibody for one hour at 4° C. Cells were analyzed for expression by flow cytometry using antibodies specific for HLA-A and H-2K$^b$. FIG. 6A shows the expression of H-2K$^b$ and HLA-A2 in the wild-type and chimeric heterozygote, with chimeric heterozygote expressing both proteins. FIG. 6B shows expression of both the H-2K$^b$ and the chimeric HLA-A2/H2K in the heterozygous mouse.

Example 2: Construction and Characterization of Genetically Modified β2 Microglobulin Mice Example 2.1: Engineering a Humanized β2 Microglobulin Locus The mouse β2 microglobulin (β2m) gene was humanized in a single step by construction of a unique targeting vector from human and mouse bacterial artificial chromosome (BAC) DNA using VELOCIGENE® technology (see, e.g., U.S. Pat. No. 6,586,251 and Valenzuela et al., supra).

Figure 7:
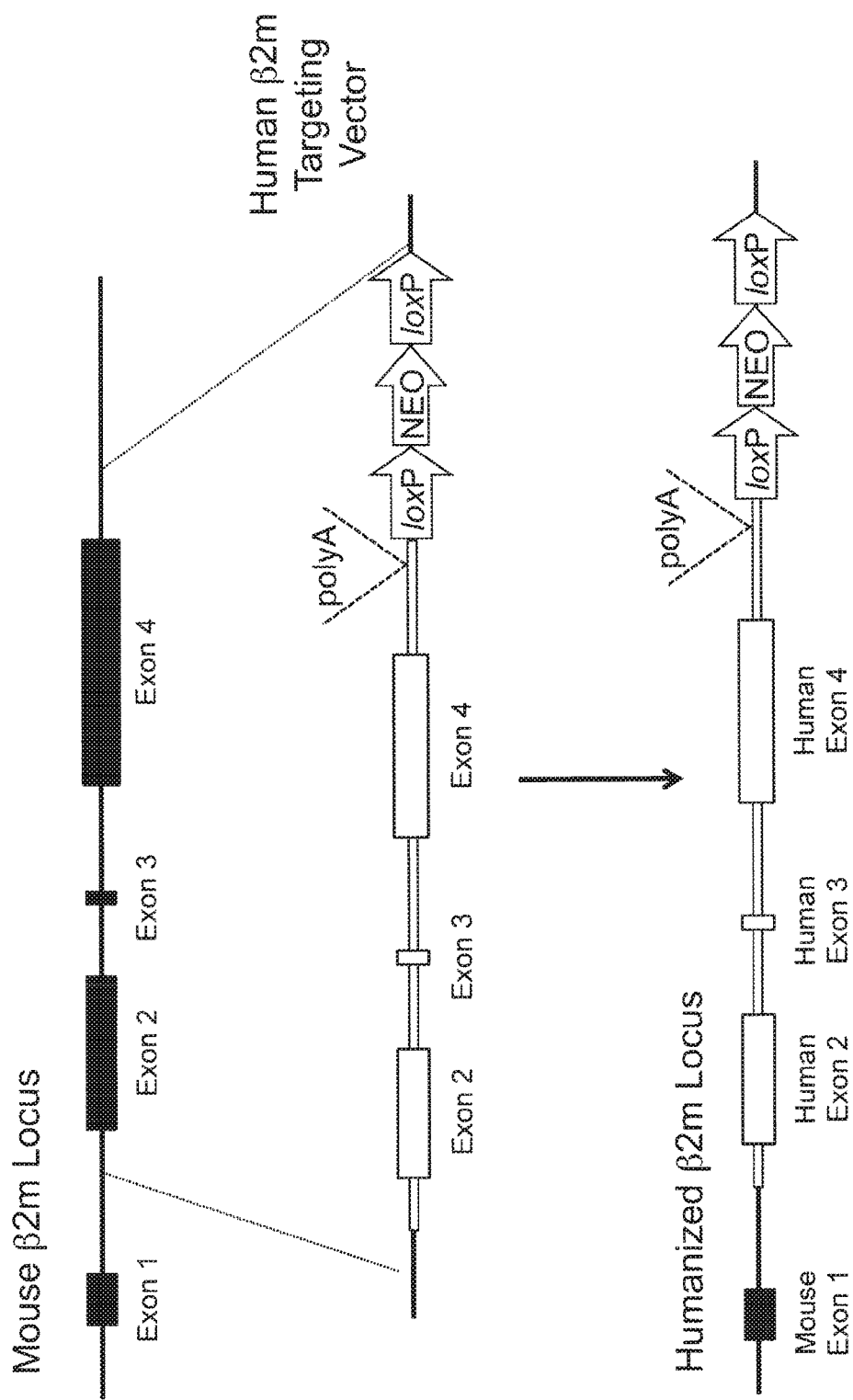
FIG. 7 shows a targeting strategy (not to scale) for humanization of a β2 microglobulin gene at a mouse β2 microglobulin locus. Mouse sequences are in black and human sequences are in white. NEO=neomycin.

Briefly, a targeting vector was generated by bacterial homologous recombination containing mouse β2m upstream and downstream homology arms from BAC clone 89C24 from the RPCI-23 library (Invitrogen). The mouse homology arms were engineered to flank a 2.8 kb human β2m DNA fragment extending from exon 2 to about 267 nucleotides downstream of non-coding exon 4 (FIG. 7). A drug selection cassette (neomycin) flanked by recombinase recognition sites (e.g., loxP sites) was engineered into the targeting vector to allow for subsequent selection. The final targeting vector was linearized and electroporated into a F1H4 mouse ES cell line (Valenzuela et al., supra).

Targeted ES cell clones with drug cassette removed (by introduction of Cre recombinase) were introduced into an 8-cell stage mouse embryo by the VELOCIMOUSE® method (see, e.g., U.S. Pat. No. 7,294,754 and Poueymirou et al., supra). VELOCIMICE® (F0 mice fully derived from the donor ES cell) bearing the humanized β2m gene were identified by screening for loss of mouse allele and gain of human allele using a modification of allele assay (Valenzuela et al., supra).

Example 2.2: Characterization of Humanized β2 Microglobulin Mice

Figure 8:
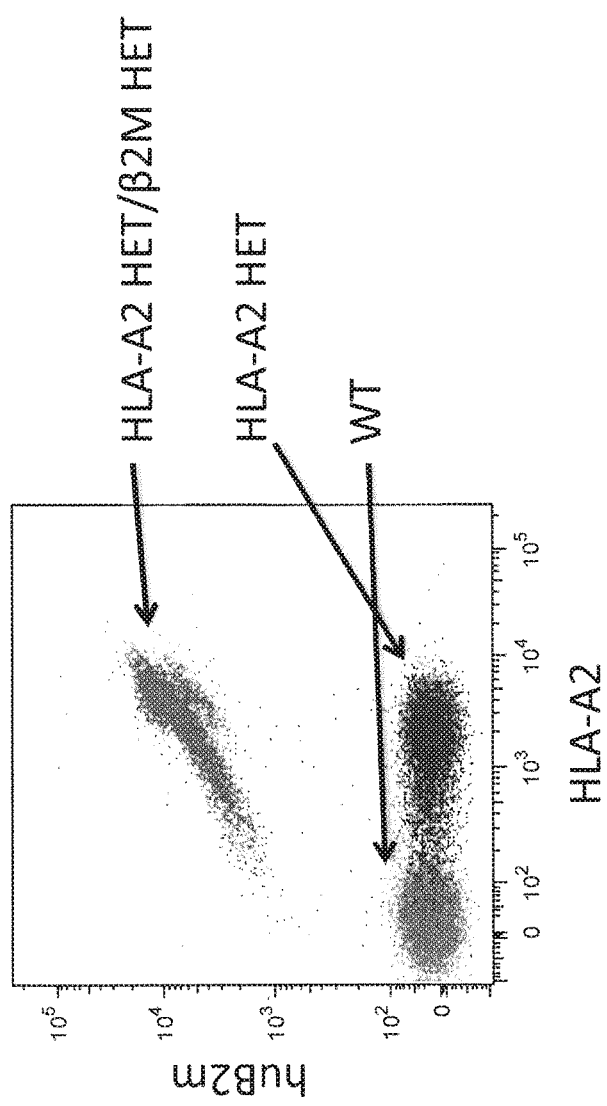
FIG. 8 shows a representative dot plot of HLA class I and human β2 microglobulin expression on cells isolated from the blood of wild-type (WT) mice, mice heterozygous for chimeric HLA-A2/H-2K, and mice heterozygous for chimeric HLA-A2/H-2K and heterozygous for humanized β2 microglobulin (double heterozygous; class I/β2m HET).
Figure 9:
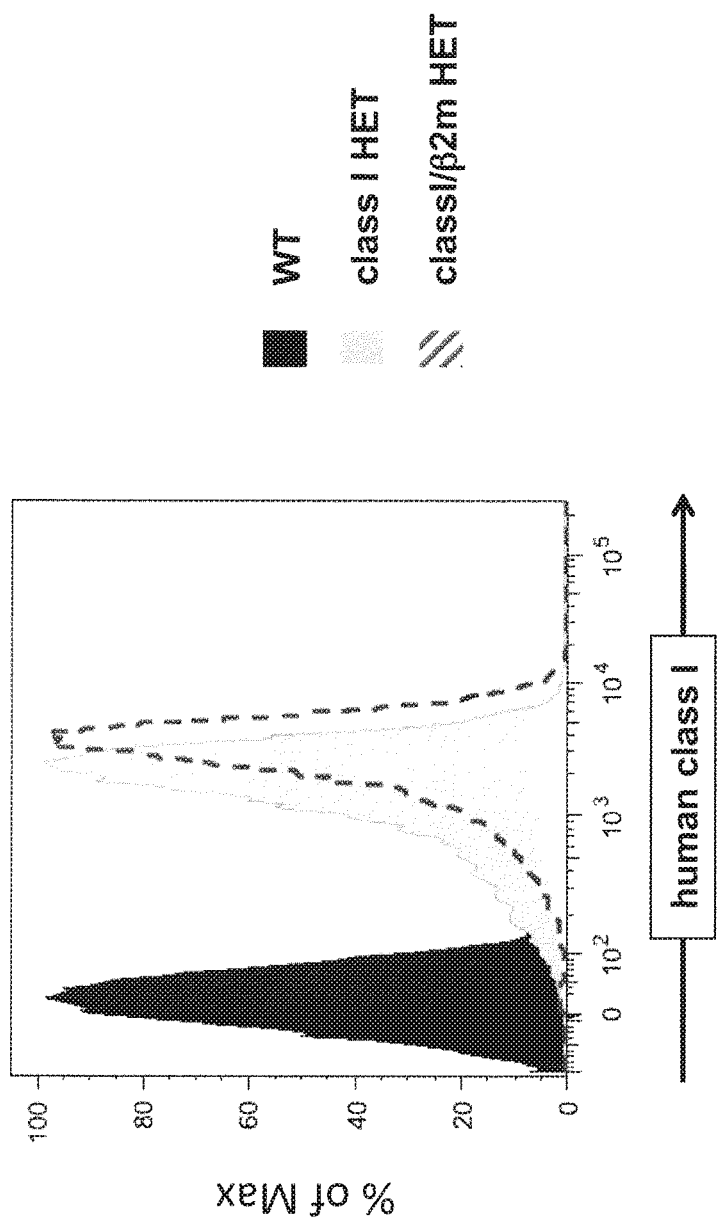
FIG. 9 shows a representative histogram of human HLA class I expression (X axis) on cells isolated from the blood of wild-type (WT), chimeric HLA-A2/H-2K heterozygous (class I HET), and chimeric HLA-A2/H2K/humanized microglobulin double heterozygous (class β2m HET) mice.

Mice heterozygous for a humanized β2 microglobulin (β2m) gene were evaluated for expression using flow cytometry (FIGS. 8 and 9).

Briefly, blood was isolated from groups (n=4 per group) of wild type, humanized β2m, humanized MHC (i.e., human HLA) class I, and double humanized β2m and MHC class I mice using techniques known in art. The blood from each of the mice in each group was treated with ACK lysis buffer (Lonza, Walkersville, Md., USA) to eliminate red blood cells. Remaining cells were stained using fluorochrome conjugated anti-CD3 (17A2), anti-C19 (1D3), anti-CD11b (M1/70), anti-human HLA class I, and anti-human β2 microglobulin (2M2) antibodies. Flow cytometry was performed using BD-FACSCANTO™ (BD Biosciences).

Expression of human HLA class I was detected on cells from single humanized and double humanized animals, while expression of β2 microglobulin was only detected on cells from double humanized mice (FIG. 8). Co-expression of human β2m and human HLA class I resulted in an increase of detectable amount of human HLA class I on the cell surface compared to human HLA class I expression in the absence of human β2m (FIG. 9; mean fluorescent intensity of 2370 versus 1387).

Example 3. Immune Response to Flu an Epstein-Barr Virus (EBV) Peptides Presented by APCs from Genetically Modified Mice Expressing HLA-A2/H-2K and Humanized β2 Microglobulin PBMCs from several human donors were screened for both HLA-A2 expression and their ability to mount a response to flu and EBV peptides. A single donor was selected for subsequent experiments.

Human T cells are isolated from PBMCs of the selected donor using negative selection. Splenic non-T cells were isolated from a mouse heterozygous for a chimeric HLA-A2/H-2K and heterozygous for a humanized β2-microglobulin gene, and a wild-type mouse. About 50,000 splenic non-T cells from the mice were added to an Elispot plate coated with anti-human IFNγ antibody. Flu peptide (10 micromolar) or a pool of EBV peptides (5 micromolar each) was added. Poly IC was added at 25 micrograms/well, and the wells were incubated for three hours at 37° C. at 5% $00_2$. Human T cells (50,000) and anti-human CD28 were added to the splenic non T cells and the peptides, and the wells were incubated for 40 hours at 37° C. at 5% CO2, after which an IFNγ Elispot assay was performed.

Figure 10:
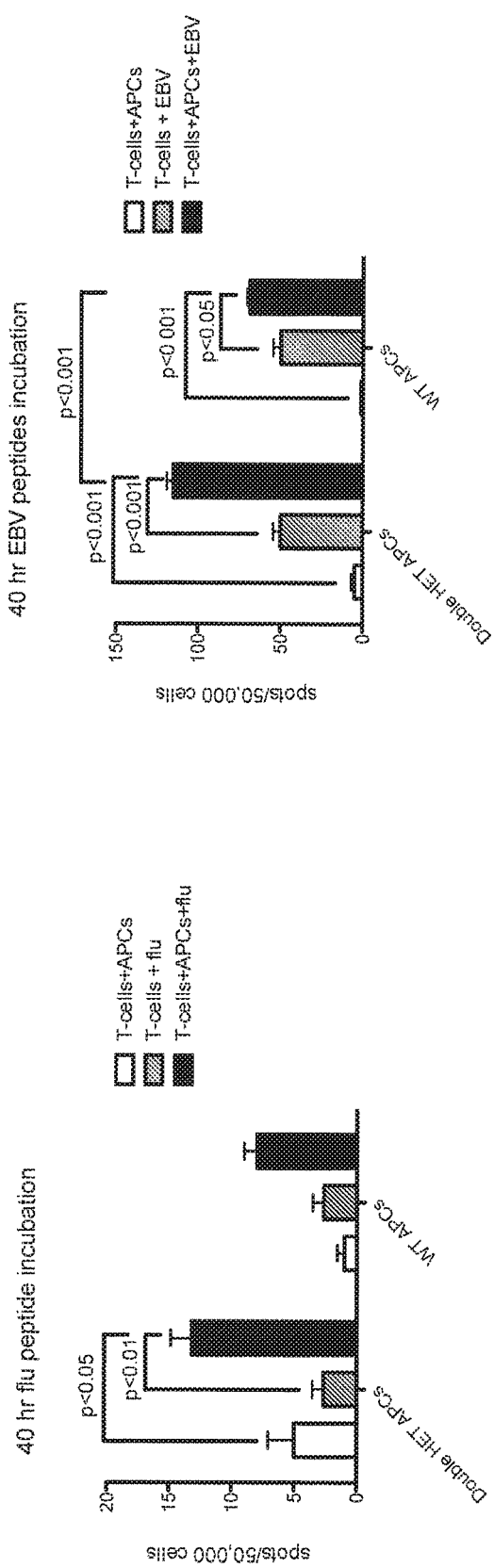
FIG. 10 shows the results of IFNγ Elispot assays for human T cells exposed to antigen-presenting cells (APCs) from wild-type mice (WT APCs) or mice heterozygous for both chimeric HLA-A2/H-2K and humanized β2 microglobulin (double HET APCs) in the presence of flu (left) or EBV (right) peptides. Statistical analysis was performed using one way ANOVA with a Tukey's Multiple Comparison Post Test.

As shown in FIG. 10, human T cells were able to mount a response to flu and EBV peptides when presented by mouse APCs that expressed the chimeric HLA-A2/H-2K and humanized β2 microglobulin on their surface.

Example 4: Construction and Characterization of Genetically Modified HLA-B27 Mice Example 4.1: Engineering a Chimeric HLA-B27/H-2D1 Locus The mouse H-2D1 (Histocompatibility 2, D region locus 1) gene was humanized in a single step by construction of a unique targeting vector from human and mouse bacterial artificial chromosome (BAC) DNA using VELOCIGENE® technology (see, e.g., U.S. Pat. No. 6,586,251 and Valenzuela et al. (2003), supra). DNA from mouse BAC clone bMQ300c10 (Invitrogen) was modified by homologous recombination to replace the genomic DNA encoding the α1, α2 and α3 domains of the mouse H-2D1 gene with human genomic DNA encoding the α1, α2 and α3 subunits of the human HLA-B27 gene (FIG. 11).

Briefly, the genomic sequence encoding the mouse the α1, α2 and α3 subunits of the H-2D1 gene is replaced with the human genomic DNA encoding the α1, α2 and α3 of the human HLA-B27 (subtypes B*2701-2759) gene in a single targeting event using a targeting vector comprising a 5' mouse homology arm containing sequence 5' of the mouse H-2D1 locus including the leader sequence exon and a 3' mouse homology arm containing genomic sequence 3' of the mouse H-2D1 polyA sequence.

Figure 11:
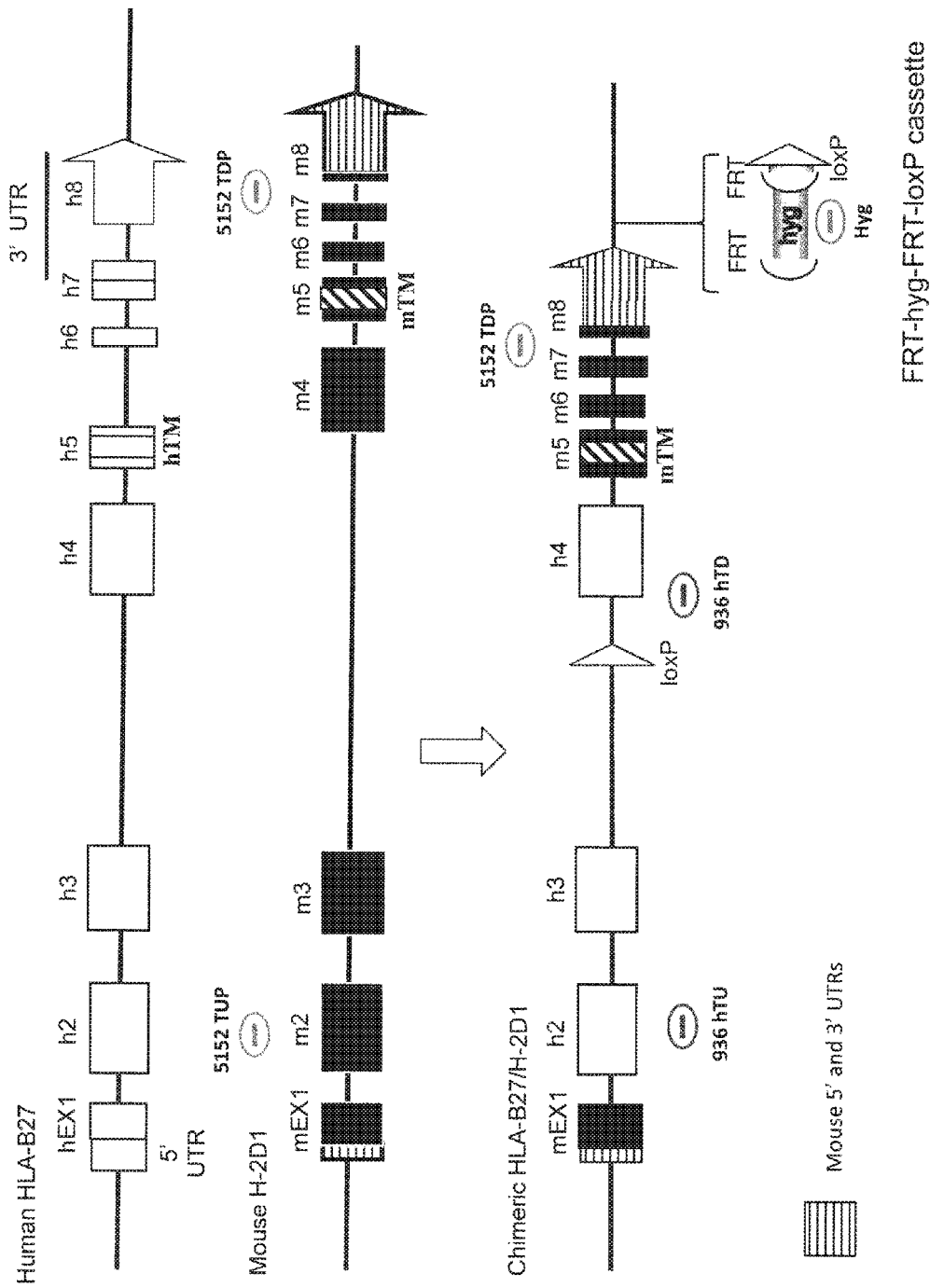
FIG. 11 is a schematic diagram (not to scale) of the targeting strategy for making a chimeric HLA-B27/H-2D1 locus that expresses an extracellular domain (in the particular embodiment depicted, human α1, α2, and α3 domains) of a human HLA-B27 gene, and endogenous mouse H-2D leader, transmembrane, and cytoplasmic domains. Locations of the probes used for genotyping (see Table 2) are also included. hEX1=human exon1; mEX1=mouse exon 1; h2, h3, h4=human exons 2, 3, and 4; m5, m6, m7, m8=mouse exons 5, 6, 7, and 8; mTM=mouse transmembrane domain in m5. Where not otherwise indicated, mouse sequences are represented in black and human sequences are represented in white.

The final construct for targeting the endogenous H-2D1 gene locus from 5' to 3' included (1) a 5' homology arm containing 49.8 kb of mouse genomic sequence 5' of the endogenous H-2D1 gene including the leader sequence exon and intron (2) 1.67 kb of human genomic sequence including the HLA-827 α1 exon, the HLA-B α1-α2 intron, the HLA-B α2 exon, the HLA-B α2-α3 intron with a 5' IoxP site insertion, the HLA-B α3 exon, (3) 1.8 kb of the mouse H-2D1 α3 intron, the H-2D1 transmembrane and cytoplasmic coding exons and polyA sequence, (4) a 5' FRT site, (5) a hygromycin cassette, (6) a 3' FRT site, (7) a 3' IoxP site and (8) a 3' homology arm containing 155.6 kb of mouse genomic sequence downstream of the mouse H-2D1 gene (see FIG. 11 for schematic representation of the H-2D1 targeting vector). The sequence of 199 nucleotides at the junction of the mouse/human sequences at the 5' of the targeting vector is set forth in SEQ ID NO: 9, the sequence of 134 nucleotides comprising IoxP insertion with its surrounding human sequences within the targeting vector is set forth in SEQ ID NO:10, the sequence of 200 nucleotides at the junction of the human/mouse sequences at the 3' of the targeting vector is set forth in SEQ ID NO:11, the sequence at the 5' junction of the mouse sequence and the FRT-HYG-FRT selection cassette is set forth in SEQ ID NO:12, and the sequence at the 3' junction of the FRT-HYG-FRT cassette and the mouse sequence is set forth in SEQ ID NO:13. Homologous recombination with this targeting vector created a modified mouse H-2D1 locus containing human genomic DNA encoding the α1, α2 and α3 domains of the HLA-B27 gene operably linked to the endogenous mouse H-2D1 transmembrane and cytoplasmic domain coding sequences which, upon translation, leads to the formation of a chimeric human/mouse MHC class I protein.

The targeted BAC DNA was used to electroporate mouse F1H4 ES cells to create modified ES cells for generating mice that express a chimeric MHC class I protein on the surface of nucleated cells (e.g., T and B lymphocytes, macrophages, neutrophils). ES cells containing an insertion of human HLA sequences were identified by a quantitative TAQMAN™ assay. Specific primer sets and probes were designed for detecting insertion of human HLA sequences and associated selection cassettes (gain of allele, GOA) and loss of endogenous mouse sequences (loss of allele, LOA). Table 2 identifies the names and locations detected for each of the probes used in the quantitative PCR assays; these probes are schematically depicted in FIG. 11.

TABLE 2

Probes Used For Confirming Chimeric HLA-B27/H-2D Gene

| Probe | Assay | Region Detected by Probe | Sequence | SEQ ID NO |
|---|---|---|---|---|
| HYG | GOA | Hygromycin cassette | ACGAGCGGGT TCGGCCCATT C | 5 |
| 936hTU | GOA | Human HLA-B27 α1 exon | TGCAAGGCCAAGGCACAGACT | 14 |
| 936hTD | GOA | Human HLA-B27 α2-α3 intron | TGCAAAGCGCCTGAATTTTCTGACTC | 15 |

TABLE 2-continued

Probes Used For Confirming Chimeric HLA-B27/H-2D Gene

| Probe | Assay | Region Detected by Probe | Sequence | SEQ ID NO |
|---|---|---|---|---|
| 5152TUP | LOA | Mouse H-2D1 α1 exon | CTCTGTCGGCTATGTGG | 16 |
| 5152TDP | Retention | Mouse H-2D1 cytoplasmic region | TGGTGGGTTGCTGGAA | 17 |

The HLA-B27/H2-D1 allele may be induced to be conditionally deleted by crossing to a Cre deletor mouse strain. For example, mice bearing the chimeric human/mouse MHC class I locus may be crossed to transgenic mice that express Ore recombinase in specific cell lineage in order to remove the "Loxed" human HLA-B27α3 and mouse H2-D1 transmembrane and cytoplasmic regions flanked by the 5' and 3' loxP sites in the targeting construct (See FIG. 11).

The selection cassette may be removed by methods known by a skilled artisan. For example, ES cells bearing the chimeric human/mouse MHC class I locus may be transfected with a construct that expresses FlpO in order to remove the "FRTed" hygromycin cassette introduced by the insertion of the targeting construct containing human HLA-B27 gene sequences (See FIG. 11). The hygromycin cassette may optionally be removed by breeding to mice that express FlpO recombinase. Optionally, the hygromycin cassette is retained in the mice.

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007), supra). VELOCIMICE® (F0 mice fully derived from the donor ES cell) independently bearing a chimeric MHC class I gene were identified by genotyping using a modification of allele assay (Valenzuela et al., supra) that detects the presence of the unique human HLA-B27 gene sequences.

Example 4.2: Expression of Chimeric HLA-B27/H-2D1 in Genetically Modified Mice

Blood from mice heterozygous for both humanized B2M and chimeric HLA-B27/H-2D1 and their wild type littermates was collected in microtainer tubes with EDTA (BD). Blood was stained with 1 mg/ml of primary antibody (W6/32-PE, pan HLA-Class I antibody. Abcam: or anti-human b2m antibody) for 25 min at 4° C. followed by washing with FACS buffer and incubation with 1:300 dilution of APC-labeled Anti-Human IgG secondary antibody (Jackson Immunoresearch) for 20 min at 4° C. Red blood cells were lysed with 1-step Fix/lyse solution (eBiosciences) and cells were fixed and resuspended in 1×BD Stabilizing Fixative. Cells were acquired on a FACS Canto machine and data was analyzed using FlowJo software.

Figure 12:
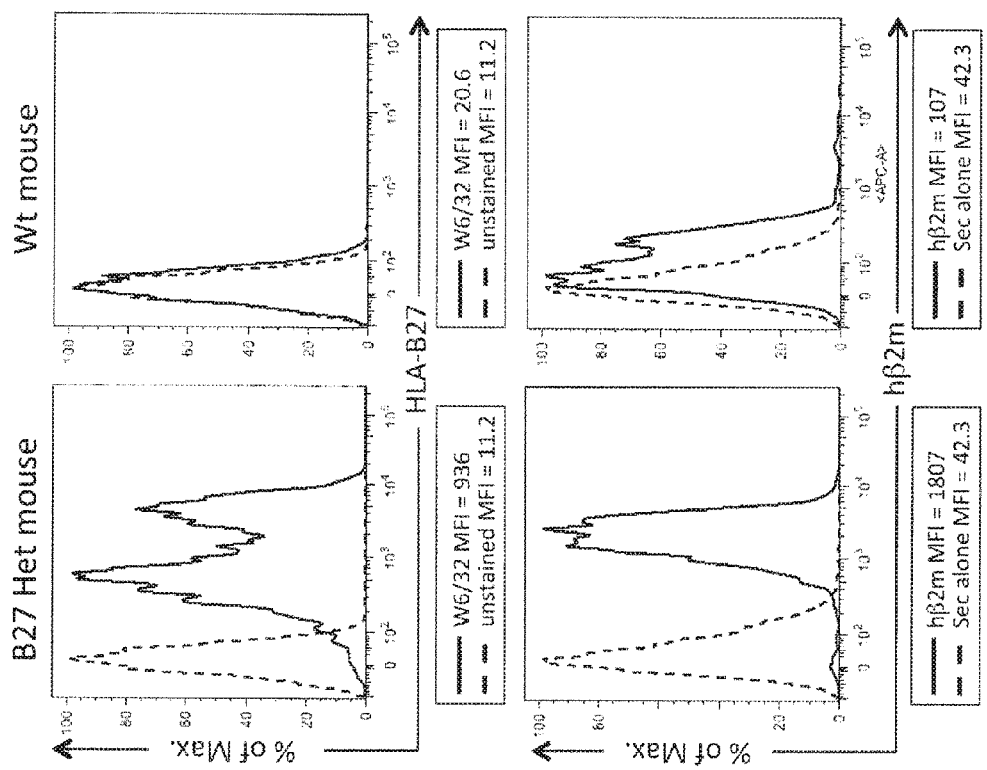
FIG. 12, top two graphs, shows representative histograms of human HLA class I expression on cells isolated from the blood of wild-type (WT; right top figure) or chimeric HLA-B27/H-2D heterozygous/humanized β2 microglobulin heterozygous (B27/hB2M Het/Het; left top figure) mice; bottom two graphs depict representative histograms of human β2 microglobulin expression on cells isolated from the blood of WT or B27/hB2M Het/Het mice. MFI=mean fluorescent intensity; sec alone=secondary antibody staining only.

As depicted in FIG. 12, chimeric HLA-B27/H-2D1 protein and humanized B2M were expressed on blood cells of genetically engineered animals (as evidenced by detection by antibodies raised against human HLA-B27 and human B-2M), while their expression was not detected in wild-type animals.

EQUIVALENTS

Those skilled in the art will recognize, or be able to ascertain using no more than routine experimentation, many equivalents of the specific embodiments of the invention described herein. Such equivalents are intended to be encompassed by the following claims.

Entire contents of all non-patent documents, patent applications and patents cited throughout this application are incorporated by reference herein in their entirety.

What is claimed is:

1. A mouse whose genome comprises
(i) at its endogenous H-2D locus a nucleotide sequence encoding a chimeric human/mouse HLA-B/H-2D polypeptide,
wherein the nucleotide sequence is in operable linkage with an endogenous mouse regulatory element and is operably linked to a MHC I polypeptide leader encoding sequence,
wherein the nucleotide sequence comprises from 5' to 3'
(a) a first nucleic acid sequence that encodes the α1, α2 and α3 domains of the human HLA-B polypeptide, which first nucleic acid sequence replaces a sequence encoding the α1, α2 and α3 domains of the mouse H-2D polypeptide at the endogenous H-2D locus, and
(b) a second nucleic acid sequence that encodes the transmembrane and cytoplasmic domains of the mouse H-2D polypeptide, and
(ii) at its endogenous mouse β2 microglobulin locus a nucleotide sequence encoding a human or humanized β2 microglobulin polypeptide, wherein the nucleotide sequence is operably linked to the endogenous mouse β2 microglobulin regulatory elements, wherein the nucleotide sequence encoding the human or humanized β2 microglobulin polypeptide comprises from 5' to 3': exon 2, exon 3 and exon 4 of a human β2 microglobulin gene, wherein the nucleotide sequence encoding the human β2 microglobulin gene replaces the endogenous mouse nucleotide sequence encoding exon 2, exon 3 and exon 4
wherein the mouse expresses at the surface of nucleated cells the chimeric HLA-B/H-2D polypeptide that comprises the α1, α2 and α3 domains of the human HLA-B polypeptide and transmembrane and cytoplasmic domains of the mouse H-2K polypeptide and the human or humanized β2 microglobulin polypeptide.

2. The animal of claim 1, wherein the animal does not express a functional endogenous mouse β2 microglobulin from its endogenous mouse β2 microglobulin locus.

3. The animal of claim 1, wherein the nucleotide sequence encoding the human or humanized β2 microglobulin polypeptide comprises a nucleotide sequence set forth in exon 2 to exon 4 of a human β2 microglobulin gene.

4. The mouse of claim 1, wherein the human HLA-B polypeptide is an HLA-B27 polypeptide.

5. The mouse of claim 4, wherein the HLA-B27 polypeptide is a polypeptide encoded by HLA-B27 allele subtypes B*2701-2759.

6. The mouse of claim 1, wherein the MHC I polypeptide leader encoding sequence is an endogenous mouse H-2D leader encoding sequence.

7. The mouse of claim 1, wherein the endogenous H-2D locus is an H-2D1 locus.

8. The mouse of claim 1, wherein the mouse is homozygous at the endogenous H 2D locus for the nucleotide sequence encoding the chimeric human/mouse HLA B/H-2D polypeptide and/or at the endogenous β2 microglobulin locus for the nucleotide sequence encoding the human or humanized β2 microglobulin polypeptide.

* * * * *

UNITED STATES PATENT AND TRADEMARK OFFICE
CERTIFICATE OF CORRECTION

PATENT NO. : 10,045,516 B2
APPLICATION NO. : 15/415544
DATED : August 14, 2018
INVENTOR(S) : Lynn Macdonald et al.

Page 1 of 1

It is certified that error appears in the above-identified patent and that said Letters Patent is hereby corrected as shown below:

In the Claims

Column 60, Lines 4-5 Claim 1:
"transmembrane and cytoplasmic domains of the mouse H-2K polypeptide"
Should read:
--transmembrane and cytoplasmic domains of the mouse H-2D polypeptide--.

Signed and Sealed this
Twenty-fifth Day of June, 2019

Andrei Iancu
*Director of the United States Patent and Trademark Office*

SEQUENCE LISTING

```
<160> NUMBER OF SEQ ID NOS: 17

<210> SEQ ID NO 1
<211> LENGTH: 200
<212> TYPE: DNA
<213> ORGANISM: Artificial
<220> FEATURE:
<223> OTHER INFORMATION: 5' homology arm of MHC I targeting construct

<400> SEQUENCE: 1
ggattcccca tctccacagt ttcacttctg cacctaacct gggtcaggtc cttctgtccg      60
gacactgttg acgcgcagtc agctcttacc cccattgggt ggcgcgatca cccaagaacc     120
aatcagtgtc gccgcggacg ctggatataa agtccacgca gcccgcagaa ctcagaagtc     180
gcgaatcgcc gacaggtgcg                                                 200

<210> SEQ ID NO 2
```

```
<211> LENGTH: 200
<212> TYPE: DNA
<213> ORGANISM: Artificial
<220> FEATURE:
<223> OTHER INFORMATION: 3' homology arm of MHC I targeting construct

<400> SEQUENCE: 2
gtaaggagag tgtgggtgca gagctggggt cagggaaagc tggagctttc tgcagaccct      60
gagctgctca gggctgagag ctggggtcat gaccctcacc ttcatttctt gtacctgtcc     120
ttcccagagc ctcctccatc cactgtctcc aacatggcga ccgttgctgt tctggttgtc     180
cttggagctg caatagtcac                                                 200

<210> SEQ ID NO 3
<211> LENGTH: 149
<212> TYPE: DNA
<213> ORGANISM: Artificial
<220> FEATURE:
<223> OTHER INFORMATION: Sequence of the chimeric human/mouse MHC I
      locus at the 5' junction of mouse/human sequences

<400> SEQUENCE: 3
agtgtcgccg cggacgctgg atataaagtc cacgcagccc gcagaactca gaagtcgcga      60
atcgccgaca ggtgcgatgg ccgtcatggc gccccgaacc ctcgtcctgc tactctcggg     120
ggctctggcc ctgacccaga cctgggcgg                                       149

<210> SEQ ID NO 4
<211> LENGTH: 159
<212> TYPE: DNA
<213> ORGANISM: Artificial
<220> FEATURE:
<223> OTHER INFORMATION: Sequence of the chimeric human/mouse MHC I
      locus at the 3' junction of human/mouse sequences

<400> SEQUENCE: 4
ggtggtgcct tctggacagg agcagagata cacctgccat gtgcagcatg agggtttgcc      60
caagcccctc accctgagat ggggtaagga gagtgtgggt gcagagctgg ggtcagggaa     120
agctggagct ttctgcagac cctgagctgc tcagggctg                            159

<210> SEQ ID NO 5
<211> LENGTH: 21
<212> TYPE: DNA
<213> ORGANISM: Artificial
<220> FEATURE:
<223> OTHER INFORMATION: Probe for detection of hygromycin cassette

<400> SEQUENCE: 5
acgagcgggt tcggcccatt c                                                21

<210> SEQ ID NO 6
<211> LENGTH: 27
<212> TYPE: DNA
<213> ORGANISM: Artificial
<220> FEATURE:
<223> OTHER INFORMATION: Probe for detection of human HLA-A2 alpha2-
      alpha3 intron

<400> SEQUENCE: 6
agtccttcag cctccactca ggtcagg                                          27

<210> SEQ ID NO 7
<211> LENGTH: 25
<212> TYPE: DNA
```

```
<213> ORGANISM: Artificial
<220> FEATURE:
<223> OTHER INFORMATION: Probe for detection of Human HLA-A2 alpha2 exon

<400> SEQUENCE: 7
taccaccagt acgcctacga cggca                                          25

<210> SEQ ID NO 8
<211> LENGTH: 18
<212> TYPE: DNA
<213> ORGANISM: Artificial
<220> FEATURE:
<223> OTHER INFORMATION: Probe for detection of human HLA-A2 alpha2-
      alpha3 intron

<400> SEQUENCE: 8
cactctctgg tacaggat                                                  18

<210> SEQ ID NO 9
<211> LENGTH: 199
<212> TYPE: DNA
<213> ORGANISM: Artificial
<220> FEATURE:
<223> OTHER INFORMATION: Sequence of the chimeric human/mouse MHC I
      locus at the 5' junction of mouse/human sequences

<400> SEQUENCE: 9
cccttctcca cctgagcccc gcgcccagat cccctcccgg cctgcgcagc cgcccggggt    60
ttggtgagga ggtcggggtc tcaccgcgcg ccgtccccag gctcccactc catgaggtat   120
ttccacacct ccgtgtcccg gcccggccgc ggggagcccc gcttcatcac cgtgggctac   180
gtggacgaca cgctgttcg                                                199

<210> SEQ ID NO 10
<211> LENGTH: 134
<212> TYPE: DNA
<213> ORGANISM: Artificial
<220> FEATURE:
<223> OTHER INFORMATION: Sequence of chimeric human/mouse MHC I locus
      surrounding 5' loxP site

<400> SEQUENCE: 10
tccctgttcc ccgctcagag actcgaactt tccaatgaat aggagattat cataacttcg    60
tataatgtat gctatacgaa gttatccagg tgcctgcgtc caggctggtg tctgggttct   120
gtgccccttc ccca                                                    134

<210> SEQ ID NO 11
<211> LENGTH: 200
<212> TYPE: DNA
<213> ORGANISM: Artificial
<220> FEATURE:
<223> OTHER INFORMATION: Sequence of chimeric human/mouse MHC I locus at
      the 3' junction of human/mouse sequences

<400> SEQUENCE: 11
agaagtgggc agctgtggtg gtgccttctg gagaagagca gagatacaca tgccatgtac    60
agcatgaggg gctgccgaag cccctcaccc tgagatgggg tgtgggtgca gagctggggt   120
cagggaaagc tggagccttc tgcagaccct gagctggtca gggatgagag ctggggtcat   180
aaccctcacc ttcatttcct                                              200

<210> SEQ ID NO 12
<211> LENGTH: 120
```

```
<212> TYPE: DNA
<213> ORGANISM: Artificial
<220> FEATURE:
<223> OTHER INFORMATION: Sequence at the 5' junction of of FRT-HYG-FRT
      insertion

<400> SEQUENCE: 12
agactcaact agggatcctt taatgtgctg ggtgtacaag acaattcacc catttcctct    60
gctcgagcga agttcctata ctttctagag aataggaact tcggaatagg aacttccgga   120

<210> SEQ ID NO 13
<211> LENGTH: 120
<212> TYPE: DNA
<213> ORGANISM: Artificial
<220> FEATURE:
<223> OTHER INFORMATION: Sequence at the 3' junction of the FRT-HYG-FRT
      insertion

<400> SEQUENCE: 13
ataggaactt ctcgagccca taacttcgta taatgtatgc tatacgaagt tatcccggtg    60
cacccatccc ttttagctac taatgatgct gtgttgaagc tgccctgggc tctccctgtc   120

<210> SEQ ID NO 14
<211> LENGTH: 21
<212> TYPE: DNA
<213> ORGANISM: Artificial
<220> FEATURE:
<223> OTHER INFORMATION: Detection probe

<400> SEQUENCE: 14
tgcaaggcca aggcacagac t                                              21

<210> SEQ ID NO 15
<211> LENGTH: 26
<212> TYPE: DNA
<213> ORGANISM: Artificial
<220> FEATURE:
<223> OTHER INFORMATION: Detection probe

<400> SEQUENCE: 15
tgcaaagcgc ctgaattttc tgactc                                         26

<210> SEQ ID NO 16
<211> LENGTH: 17
<212> TYPE: DNA
<213> ORGANISM: Artificial
<220> FEATURE:
<223> OTHER INFORMATION: Detection probe

<400> SEQUENCE: 16
ctctgtcggc tatgtgg                                                   17

<210> SEQ ID NO 17
<211> LENGTH: 16
<212> TYPE: DNA
<213> ORGANISM: Artificial
<220> FEATURE:
<223> OTHER INFORMATION: Detection probe

<400> SEQUENCE: 17
tggtgggttg ctggaa                                                    16
```